United States Patent
Greenberg et al.

(10) Patent No.: US 12,209,240 B2
(45) Date of Patent: Jan. 28, 2025

(54) ANTISENSE ANTIBACTERIAL COMPOUNDS AND METHODS

(71) Applicants: Board of Regents, The University of Texas System, Austin, TX (US); Oregon State University, Corvallis, OR (US)

(72) Inventors: David Greenberg, Coppell, TX (US); Bruce L. Geller, Corvallis, OR (US)

(73) Assignees: Board of Regents, The University of Texas System, Austin, TX (US); Oregon State University, Corvallis, OR (US)

( * ) Notice: Subject to any disclaimer, the term of this patent is extended or adjusted under 35 U.S.C. 154(b) by 73 days.

(21) Appl. No.: 17/498,880

(22) Filed: Oct. 12, 2021

(65) Prior Publication Data

US 2022/0135973 A1    May 5, 2022

Related U.S. Application Data

(62) Division of application No. 16/064,306, filed as application No. PCT/US2016/068376 on Dec. 22, 2016, now Pat. No. 11,142,764.

(60) Provisional application No. 62/387,178, filed on Dec. 23, 2015.

(51) Int. Cl.
| | |
|---|---|
| *C07H 21/04* | (2006.01) |
| *A61K 31/7115* | (2006.01) |
| *A61K 31/712* | (2006.01) |
| *A61K 47/42* | (2017.01) |
| *A61K 47/66* | (2017.01) |
| *C12N 15/113* | (2010.01) |

(52) U.S. Cl.
CPC ........ *C12N 15/113* (2013.01); *A61K 31/7115* (2013.01); *A61K 31/712* (2013.01); *A61K 47/42* (2013.01); *A61K 47/66* (2017.08); *C12N 2310/11* (2013.01); *C12N 2310/3233* (2013.01); *C12N 2310/3513* (2013.01)

(58) Field of Classification Search
None
See application file for complete search history.

(56) References Cited

U.S. PATENT DOCUMENTS

| | | | |
|---|---|---|---|
| 8,067,571 | B2 | 11/2011 | Weller et al. |
| 2010/0016215 | A1 | 1/2010 | Moulton et al. |
| 2013/0288369 | A1 | 10/2013 | Iverson |
| 2015/0141321 | A1 | 5/2015 | Kole et al. |
| 2015/0361425 | A1 | 12/2015 | Geller et al. |

FOREIGN PATENT DOCUMENTS

| | | |
|---|---|---|
| JP | 2003-516151 | 5/2003 |
| WO | WO 2001-042457 | 6/2001 |
| WO | WO 2004-097017 | 11/2004 |
| WO | WO 2007-009094 | 1/2007 |
| WO | WO 2009-005793 | 1/2009 |
| WO | WO 2012-150960 | 11/2012 |
| WO | WO 2015-175977 | 11/2015 |
| WO | WO 2015-179249 | 11/2015 |
| WO | WO 2016-108930 | 7/2016 |
| WO | WO 2017-112885 | 6/2017 |
| WO | WO 2019-083823 | 5/2019 |

OTHER PUBLICATIONS

Extended European Search Report issued in European Application No. 16880107.4, mailed on Nov. 25, 2019.
Greenberg et al., "Antisense phosphorodiamidate morpholino oligomers targeted to an essential gene inhibit *Burkholderia cepacia* complex," *The Journal of Infectious Diseases*, 201(12):1822-1830, 2010.
Mellbye et al., "Variations in amino acid composition of antisense peptide-phosphorodiamidate morpholino oligomer affect potency against *Escherichia coli* in vitro and in vivo," *Antimicrobial Agents and Chemotherapy*, 53(2):525-530, 2009.
Office Action issued in Australian Application No. 2016379402, mailed Apr. 4, 2022.
Office Action issued in European Application No. 16880107.4, mailed Dec. 18, 2020.
Office Action issued in Japanese Application No. 2018-553039, mailed Feb. 1, 2021, and English language translation thereof.
Office Action issued in Japanese Application No. 2018-553039, mailed Oct. 27, 2021, and English language translation thereof.
Office Action issued in Japanese Application No. 2018-553039, mailed Apr. 6, 2022, and English language translation thereof.
Office Action issued in U.S. Appl. No. 15/540,387, mailed Oct. 29, 2021.
Office Action issued in U.S. Appl. No. 16/064,306, mailed Feb. 12, 2020.
Office Action issued in U.S. Appl. No. 16/064,306, mailed Jun. 24, 2020.
PCT International Preliminary Report on Patentability issued in International Application No. PCT/US2016/068376, mailed Jun. 26, 2018.
PCT International Search Report and Written Opinion issued in International Application No. PCT/US2016/068376, mailed Mar. 13, 2017.
Deere et al., "Antisense phosphorodiamidate morpholine oligomer length and target position effects on gene-specific inhibition in *Escherichia coli*," *Antimicrobial Agents and Chemotherapy*, 49(1):249-255, 2005.
Office Action issued in European Application No. 16880107.4, mailed Apr. 26, 2024.

*Primary Examiner* — Kimberly Chong
(74) *Attorney, Agent, or Firm* — Parker Highlander PLLC

(57) ABSTRACT

Provided are antisense oligomers targeted against bacterial mRNAs and other macromolecules associated with a biochemical pathway and/or cellular process, and related compositions and methods of using the oligomers and compositions to treat an infected mammalian subject, for example, as primary antimicrobials or as adjunctive therapies with classic antimicrobials.

16 Claims, 6 Drawing Sheets
Specification includes a Sequence Listing.

A  B  C

D  E

P007 5' PPMO

AcHN R X R R X R R X R R X R X B

FIG. 2

| Species | Strain ID | Characteristics | PPMO#15 | PPMO#17 | PPMO#18 | PPMO#19 | Scrambled |
|---|---|---|---|---|---|---|---|
| Klebsiella pneumoniae | BAA 2146 | NDM-1, MDR | 8 | 16 | >32 | >32 | >32 |
| Klebsiella pneumoniae | 3190 | Mer$^R$, Cef$^R$, Pip/Taz$^R$, Cip$^R$ | 8 | 4 | >32 | >32 | 128 |
| Klebsiella pneumoniae | Hm 751 | human sputum | 2 | 4 | 8 | >32 | 64 |
| Klebsiella pneumoniae | NDM1-A | MDR, NDM-1 | 2 | 16 | 16 | 32 | >128 |
| Klebsiella pneumoniae | NDM1-C | MDR, NDM-1 | 2 | 32 | >32 | >32 | >128 |
| Klebsiella pneumoniae | 15410 | KPC | 2 | 2 | 32 | >32 | >128 |
| Klebsiella pneumoniae | 15412 | KPC | 1 | 4 | 16 | >32 | >32 |
| Klebsiella pneumoniae | Hm748 | stool | 1 | 4 | 8 | >32 | 64 |
| Klebsiella pneumoniae | OR-1 | KPC, MDR | 0.5 | 2 | 8 | >32 | >32 |
| Klebsiella pneumoniae | OR-5 | urine, MDR | 2 | 8 | >32 | >32 | >32 |
| Klebsiella pneumoniae | OR-10 | sputum | 1 | 8 | 16 | >32 | >32 |
| Klebsiella pneumoniae | OR-13 | KPC, urine | 8 | 16 | >16 | >32 | 128 |
| Klebsiella pneumoniae | OR-15 | urine, MDR | 0.5 | 2 | 4 | >32 | >32 |
| Klebsiella pneumoniae | OR-20 | clinical isolate | 1 | 16 | 16 | >32 | >32 |
| IC75 | | | 2 | 16 | >32 | >32 | >32 |
| | | | | | | | |
| Pseudomonas aeruginosa | PAO1 | wound | 2 | 8 | 1 | 64 | >128 |
| Pseudomonas aeruginosa | PA14 | cystic fibrosis, high virulence | 1 | 4 | 1 | 32 | >128 |
| Pseudomonas aeruginosa | 020507-1.4 | cystic fibrosis | 1 | 2 | 0.5 | 4 | >128 |
| Pseudomonas aeruginosa | 120406-8.20 | cystic fibrosis | 8 | 4 | 8 | 64 | >128 |
| Pseudomonas aeruginosa | 121206-7.7 | cystic fibrosis | 4 | 2 | 1 | 64 | >128 |
| Pseudomonas aeruginosa | 030507-2.9 | cystic fibrosis | 1 | 2 | 1 | 16 | >128 |
| Pseudomonas aeruginosa | ZK-2870 | cystic fibrosis | 2 | 2 | 1 | 32 | >128 |
| IC75 | | | 4 | 4 | 1 | 64 | >128 |
| | | | | | | | |
| Acinetobacter baumannii | AYE | MDR, human blood | 32 | >32 | 4 | 8 | 128 |
| Acinetobacter baumannii | AYE (pNDM-1) | MDR, transconjgate | >32 | >32 | 8 | 8 | 128 |
| Acinetobacter baumannii | AB0057 | MDR | >32 | >32 | 4 | 8 | 128 |
| Acinetobacter baumannii | 17978 | MDR, meningitis | >32 | >32 | 8 | 8 | >128 |
| Acinetobacter baumannii | M281188 | MDR | 32 | >32 | 8 | 8 | 64 |
| Acinetobacter haemolyticus | 17906 | MDR, sputum | 32 | >32 | 4 | 8 | >128 |
| Acinetobacter baumannii | 9 | MDR | 32 | 16 | 2 | 8 | 128 |
| Acinetobacter baumannii | BCT-B-028 | NDM-1, MDR | 32 | >32 | 4 | 8 | 128 |
| Acinetobacter baumannii | 28180 | MDR | >32 | >32 | 8 | 8 | 128 |
| Acinetobacter baumannii | F-1299 | MDR | >32 | >32 | 16 | 16 | >128 |
| Acinetobacter baumannii | M22351 | MDR | >32 | >32 | >32 | 32 | >128 |
| Acinetobacter baumannii | S-18946 | MDR | 32 | >32 | 8 | 8 | >128 |
| Acinetobacter baumannii | S-39424 | MDR | >32 | >32 | 8 | 8 | >128 |
| Acinetobacter baumannii | X-60546 | MDR | >32 | >32 | 8 | 8 | 128 |
| Acinetobacter baumannii | 19606 | MDR, urine | >32 | 4 | 1 | 4 | 128 |
| Acinetobacter indicus | 17976 | meningitis | 8 | 16 | 8* | 8* | 128 |
| IC75 | | | >32 | >32 | 8 | 8 | >128 |
| | | | | | | | |
| | | * Measured in MH II medium | | | | | |

SEQUENCE LISTING

```
<160> NUMBER OF SEQ ID NOS: 35

<210> SEQ ID NO 1
<211> LENGTH: 11
<212> TYPE: DNA
<213> ORGANISM: Pseudomonas aeruginosa
<220> FEATURE:
<221> NAME/KEY: misc_feature
<222> LOCATION: (2)..(2)
<223> OTHER INFORMATION: n may be thymidine or uracil
<220> FEATURE:
<221> NAME/KEY: misc_feature
<222> LOCATION: (5)..(5)
<223> OTHER INFORMATION: n may be thymidine or uracil
<220> FEATURE:
<221> NAME/KEY: misc_feature
<222> LOCATION: (9)..(10)
<223> OTHER INFORMATION: n may be thymidine or uracil
```

<400> SEQUENCE: 1
cncanaccnn g          11

<210> SEQ ID NO 2
<211> LENGTH: 11
<212> TYPE: DNA
<213> ORGANISM: Klebsiella pneumoniae
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (4)..(4)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
<220> FEATURE:
<221> NAME/KEY: misc_feature
<222> LOCATION: (10)..(10)
<223> OTHER INFORMATION: n may be thymidine or uracil

<400> SEQUENCE: 2
ngcncanacn c          11

<210> SEQ ID NO 3
<211> LENGTH: 11
<212> TYPE: DNA
<213> ORGANISM: Pseudomonas aeruginosa
<220> FEATURE:
<221> NAME/KEY: misc_feature
<222> LOCATION: (3)..(5)
<223> OTHER INFORMATION: n may be thymidine or uracil
<220> FEATURE:
<221> NAME/KEY: misc_feature
<222> LOCATION: (8)..(9)
<223> OTHER INFORMATION: n may be thymidine or uracil

<400> SEQUENCE: 3
cgnnncanna a          11

<210> SEQ ID NO 4
<211> LENGTH: 11
<212> TYPE: DNA
<213> ORGANISM: Pseudomonas aeruginosa
<220> FEATURE:
<221> NAME/KEY: misc_feature
<222> LOCATION: (1)..(3)
<223> OTHER INFORMATION: n may be thymidine or uracil
<220> FEATURE:
<221> NAME/KEY: misc_feature
<222> LOCATION: (5)..(5)
<223> OTHER INFORMATION: n may be thymidine or uracil
<220> FEATURE:
<221> NAME/KEY: misc_feature
<222> LOCATION: (9)..(10)
<223> OTHER INFORMATION: n may be thymidine or uracil

<400> SEQUENCE: 4
nnnanccann g          11

<210> SEQ ID NO 5
<211> LENGTH: 11
<212> TYPE: DNA
<213> ORGANISM: Pseudomonas aeruginosa
<220> FEATURE:
<221> NAME/KEY: misc_feature
<222> LOCATION: (4)..(6)

```
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 5
gcannngacc n                                                              11

<210> SEQ ID NO 6
<211> LENGTH: 11
<212> TYPE: DNA
<213> ORGANISM: Klebsiella pneumoniae
<220> FEATURE:
<221> NAME/KEY: misc_feature
<222> LOCATION: (2)..(2)
<223> OTHER INFORMATION: n may be thymidine or uracil
<220> FEATURE:
<221> NAME/KEY: misc_feature
<222> LOCATION: (4)..(4)
<223> OTHER INFORMATION: n may be thymidine or uracil
<220> FEATURE:
<221> NAME/KEY: misc_feature
<222> LOCATION: (6)..(7)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil

<400> SEQUENCE: 6
gncnanncnc c                                                              11

<210> SEQ ID NO 7
<211> LENGTH: 11
<212> TYPE: DNA
<213> ORGANISM: Pseudomonas aeruginosa
<220> FEATURE:
<221> NAME/KEY: misc_feature
<222> LOCATION: (5)..(5)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 7
gacangncna n                                                              11

<210> SEQ ID NO 8
<211> LENGTH: 11
<212> TYPE: DNA
<213> ORGANISM: Pseudomonas aeruginosa
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (4)..(5)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
```

-continued

<220> FEATURE:
<221> NAME/KEY: misc_feature
<222> LOCATION: (11)..(11)
<223> OTHER INFORMATION: n may be thymidine or uracil

<400> SEQUENCE: 8
nggnncngca n                                                              11

<210> SEQ ID NO 9
<211> LENGTH: 11
<212> TYPE: DNA
<213> ORGANISM: Pseudomonas aeruginosa
<220> FEATURE:
<221> NAME/KEY: misc_feature
<222> LOCATION: (3)..(5)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil

<400> SEQUENCE: 9
agnnncncnc c                                                              11

<210> SEQ ID NO 10
<211> LENGTH: 11
<212> TYPE: DNA
<213> ORGANISM: Pseudomonas aeruginosa
<220> FEATURE:
<221> NAME/KEY: misc_feature
<222> LOCATION: (2)..(3)
<223> OTHER INFORMATION: n may be thymidine or uracil
<220> FEATURE:
<221> NAME/KEY: misc_feature
<222> LOCATION: (10)..(10)
<223> OTHER INFORMATION: n may be thymidine or uracil

<400> SEQUENCE: 10
gnncaaacan a                                                              11

<210> SEQ ID NO 11
<211> LENGTH: 11
<212> TYPE: DNA
<213> ORGANISM: Pseudomonas aeruginosa
<220> FEATURE:
<221> NAME/KEY: misc_feature
<222> LOCATION: (4)..(4)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil

<400> SEQUENCE: 11
cgcncancna a                                                              11

<210> SEQ ID NO 12
<211> LENGTH: 11
<212> TYPE: DNA
<213> ORGANISM: Pseudomonas aeruginosa
<220> FEATURE:
<221> NAME/KEY: misc_feature
<222> LOCATION: (1)..(2)

```
<223> OTHER INFORMATION: n may be thymidine or uracil
<220> FEATURE:
<221> NAME/KEY: misc_feature
<222> LOCATION: (5)..(5)
<223> OTHER INFORMATION: n may be thymidine or uracil
<220> FEATURE:
<221> NAME/KEY: misc_feature
<222> LOCATION: (10)..(10)
<223> OTHER INFORMATION: n may be thymidine or uracil

<400> SEQUENCE: 12
nnccngccan a                                                              11

<210> SEQ ID NO 13
<211> LENGTH: 11
<212> TYPE: DNA
<213> ORGANISM: Pseudomonas aeruginosa
<220> FEATURE:
<221> NAME/KEY: misc_feature
<222> LOCATION: (1)..(3)
<223> OTHER INFORMATION: n may be thymidine or uracil
<220> FEATURE:
<221> NAME/KEY: misc_feature
<222> LOCATION: (6)..(6)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil

<400> SEQUENCE: 13
nnngancanc g                                                              11

<210> SEQ ID NO 14
<211> LENGTH: 11
<212> TYPE: DNA
<213> ORGANISM: Artificial Sequence
<220> FEATURE:
<223> OTHER INFORMATION: bacterial 23S rRNA
<220> FEATURE:
<221> NAME/KEY: misc_feature
<222> LOCATION: (3)..(3)
<223> OTHER INFORMATION: n may be thymidine or uracil
<220> FEATURE:
<221> NAME/KEY: misc_feature
<222> LOCATION: (6)..(6)
<223> OTHER INFORMATION: n may be thymidine or uracil
<220> FEATURE:
<221> NAME/KEY: misc_feature
<222> LOCATION: (8)..(8)
<223> OTHER INFORMATION: n may be thymidine or uracil

<400> SEQUENCE: 14
agngcncnac c                                                              11

<210> SEQ ID NO 15
<211> LENGTH: 11
<212> TYPE: DNA
<213> ORGANISM: Artificial Sequence
<220> FEATURE:
<223> OTHER INFORMATION: bacterial 23S rRNA
<220> FEATURE:
<221> NAME/KEY: misc_feature
<222> LOCATION: (4)..(4)
<223> OTHER INFORMATION: n may be thymidine or uracil
<220> FEATURE:
<221> NAME/KEY: misc_feature
<222> LOCATION: (6)..(7)
<223> OTHER INFORMATION: n may be thymidine or uracil
<220> FEATURE:
<221> NAME/KEY: misc_feature
<222> LOCATION: (9)..(9)
<223> OTHER INFORMATION: n may be thymidine or uracil
```

```
<400> SEQUENCE: 15
gccngnnanc c                                                          11

<210> SEQ ID NO 16
<211> LENGTH: 11
<212> TYPE: DNA
<213> ORGANISM: Artificial Sequence
<220> FEATURE:
<223> OTHER INFORMATION: bacterial 16S rRNA
<220> FEATURE:
<221> NAME/KEY: misc_feature
<222> LOCATION: (4)..(4)
<223> OTHER INFORMATION: n may be thymidine or uracil

<400> SEQUENCE: 16
ccangcagca c                                                          11

<210> SEQ ID NO 17
<211> LENGTH: 11
<212> TYPE: DNA
<213> ORGANISM: Artificial Sequence
<220> FEATURE:
<223> OTHER INFORMATION: bacterial 16S rRNA
<220> FEATURE:
<221> NAME/KEY: misc_feature
<222> LOCATION: (1)..(2)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil
<220> FEATURE:
<221> NAME/KEY: misc_feature
<222> LOCATION: (10)..(11)
<223> OTHER INFORMATION: n may be thymidine or uracil

<400> SEQUENCE: 17
nngcgcncgn n                                                          11

<210> SEQ ID NO 18
<211> LENGTH: 11
<212> TYPE: DNA
<213> ORGANISM: Artificial Sequence
<220> FEATURE:
<223> OTHER INFORMATION: bacterial 16S rRNA
<220> FEATURE:
<221> NAME/KEY: misc_feature
<222> LOCATION: (4)..(4)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil

<400> SEQUENCE: 18
ggcngcnggc a                                                          11

<210> SEQ ID NO 19
<211> LENGTH: 11
<212> TYPE: DNA
<213> ORGANISM: Acinetobacter baumannii
<220> FEATURE:
<221> NAME/KEY: misc_feature
<222> LOCATION: (1)..(1)
<223> OTHER INFORMATION: n may be thymidine or uracil
<220> FEATURE:
<221> NAME/KEY: misc_feature
<222> LOCATION: (4)..(4)
<223> OTHER INFORMATION: n may be thymidine or uracil
<220> FEATURE:
```

```
<221> NAME/KEY: misc_feature
<222> LOCATION: (6)..(8)
<223> OTHER INFORMATION: n may be thymidine or uracil
<220> FEATURE:
<221> NAME/KEY: misc_feature
<222> LOCATION: (11)..(11)
<223> OTHER INFORMATION: n may be thymidine or uracil

<400> SEQUENCE: 19
ncancnnngc n                                                          11

<210> SEQ ID NO 20
<211> LENGTH: 11
<212> TYPE: DNA
<213> ORGANISM: Pseudomonas aeruginosa
<220> FEATURE:
<221> NAME/KEY: misc_feature
<222> LOCATION: (3)..(3)
<223> OTHER INFORMATION: n may be thymidine or uracil
<220> FEATURE:
<221> NAME/KEY: misc_feature
<222> LOCATION: (7)..(7)
<223> OTHER INFORMATION: n may be thymidine or uracil

<400> SEQUENCE: 20
agnaacncca c                                                          11

<210> SEQ ID NO 21
<211> LENGTH: 12
<212> TYPE: PRT
<213> ORGANISM: Artificial Sequence
<220> FEATURE:
<223> OTHER INFORMATION: (RXR)4 cell penetrating peptide
<220> FEATURE:
<221> NAME/KEY: misc_feature
<222> LOCATION: (2)..(2)
<223> OTHER INFORMATION: Xaa may be 6-aminohexanoic acid
<220> FEATURE:
<221> NAME/KEY: misc_feature
<222> LOCATION: (5)..(5)
<223> OTHER INFORMATION: Xaa may be 6-aminohexanoic acid
<220> FEATURE:
<221> NAME/KEY: misc_feature
<222> LOCATION: (8)..(8)
<223> OTHER INFORMATION: Xaa may be 6-aminohexanoic acid
<220> FEATURE:
<221> NAME/KEY: misc_feature
<222> LOCATION: (11)..(11)
<223> OTHER INFORMATION: Xaa may be 6-aminohexanoic acid

<400> SEQUENCE: 21

Arg Xaa Arg Arg Xaa Arg Arg Xaa Arg Arg Xaa Arg
1               5                   10

<210> SEQ ID NO 22
<211> LENGTH: 10
<212> TYPE: PRT
<213> ORGANISM: Artificial Sequence
<220> FEATURE:
<223> OTHER INFORMATION: (RFF)3R cell penetrating peptide

<400> SEQUENCE: 22

Arg Phe Phe Arg Phe Phe Arg Phe Phe Arg
1               5                   10

<210> SEQ ID NO 23
<211> LENGTH: 14
<212> TYPE: PRT
<213> ORGANISM: Artificial Sequence
<220> FEATURE:
<223> OTHER INFORMATION: (RXR)4XB cell penetrating peptide
```

```
<220> FEATURE:
<221> NAME/KEY: misc_feature
<222> LOCATION: (2)..(2)
<223> OTHER INFORMATION: Xaa may be 6-aminohexanoic acid
<220> FEATURE:
<221> NAME/KEY: misc_feature
<222> LOCATION: (5)..(5)
<223> OTHER INFORMATION: Xaa may be 6-aminohexanoic acid
<220> FEATURE:
<221> NAME/KEY: misc_feature
<222> LOCATION: (8)..(8)
<223> OTHER INFORMATION: Xaa may be 6-aminohexanoic acid
<220> FEATURE:
<221> NAME/KEY: misc_feature
<222> LOCATION: (11)..(11)
<223> OTHER INFORMATION: Xaa may be 6-aminohexanoic acid
<220> FEATURE:
<221> NAME/KEY: misc_feature
<222> LOCATION: (13)..(13)
<223> OTHER INFORMATION: Xaa may be 6-aminohexanoic acid
<220> FEATURE:
<221> NAME/KEY: misc_feature
<222> LOCATION: (14)..(14)
<223> OTHER INFORMATION: Xaa may be beta-alanine

<400> SEQUENCE: 23

Arg Xaa Arg Arg Xaa Arg Arg Xaa Arg Arg Xaa Arg Xaa Xaa
1               5                   10

<210> SEQ ID NO 24
<211> LENGTH: 12
<212> TYPE: PRT
<213> ORGANISM: Artificial Sequence
<220> FEATURE:
<223> OTHER INFORMATION: (RFF)3RXB cell penetrating peptide
<220> FEATURE:
<221> NAME/KEY: misc_feature
<222> LOCATION: (11)..(11)
<223> OTHER INFORMATION: Xaa may be 6-aminohexanoic acid
<220> FEATURE:
<221> NAME/KEY: misc_feature
<222> LOCATION: (12)..(12)
<223> OTHER INFORMATION: Xaa may be beta-alanine

<400> SEQUENCE: 24

Arg Phe Phe Arg Phe Phe Arg Phe Phe Arg Xaa Xaa
1               5                   10

<210> SEQ ID NO 25
<211> LENGTH: 12
<212> TYPE: PRT
<213> ORGANISM: Artificial Sequence
<220> FEATURE:
<223> OTHER INFORMATION: (RFR)4 cell penetrating peptide

<400> SEQUENCE: 25

Arg Phe Arg Arg Phe Arg Arg Phe Arg Arg Phe Arg
1               5                   10

<210> SEQ ID NO 26
<211> LENGTH: 12
<212> TYPE: PRT
<213> ORGANISM: Artificial Sequence
<220> FEATURE:
<223> OTHER INFORMATION: (RYR)4 cell penetrating peptide

<400> SEQUENCE: 26

Arg Tyr Arg Arg Tyr Arg Arg Tyr Arg Arg Tyr Arg
1               5                   10

<210> SEQ ID NO 27
```

```
<211> LENGTH: 12
<212> TYPE: PRT
<213> ORGANISM: Artificial Sequence
<220> FEATURE:
<223> OTHER INFORMATION: (RGR)4 cell penetrating peptide

<400> SEQUENCE: 27

Arg Gly Arg Arg Gly Arg Arg Gly Arg Arg Gly Arg
1               5                   10

<210> SEQ ID NO 28
<211> LENGTH: 14
<212> TYPE: PRT
<213> ORGANISM: Artificial Sequence
<220> FEATURE:
<223> OTHER INFORMATION: (RFR)4XB cell penetrating peptide
<220> FEATURE:
<221> NAME/KEY: misc_feature
<222> LOCATION: (13)..(13)
<223> OTHER INFORMATION: Xaa may be 6-aminohexanoic acid
<220> FEATURE:
<221> NAME/KEY: misc_feature
<222> LOCATION: (14)..(14)
<223> OTHER INFORMATION: Xaa may be beta-alanine

<400> SEQUENCE: 28

Arg Phe Arg Arg Phe Arg Arg Phe Arg Arg Phe Arg Xaa Xaa
1               5                   10

<210> SEQ ID NO 29
<211> LENGTH: 14
<212> TYPE: PRT
<213> ORGANISM: Artificial Sequence
<220> FEATURE:
<223> OTHER INFORMATION: (RYR)4XB cell penetrating peptide
<220> FEATURE:
<221> NAME/KEY: misc_feature
<222> LOCATION: (13)..(13)
<223> OTHER INFORMATION: Xaa may be 6-aminohexanoic acid
<220> FEATURE:
<221> NAME/KEY: misc_feature
<222> LOCATION: (14)..(14)
<223> OTHER INFORMATION: Xaa may be beta-alanine

<400> SEQUENCE: 29

Arg Tyr Arg Arg Tyr Arg Arg Tyr Arg Arg Tyr Arg Xaa Xaa
1               5                   10

<210> SEQ ID NO 30
<211> LENGTH: 14
<212> TYPE: PRT
<213> ORGANISM: Artificial Sequence
<220> FEATURE:
<223> OTHER INFORMATION: (RGR)4XB cell penetrating peptide
<220> FEATURE:
<221> NAME/KEY: misc_feature
<222> LOCATION: (13)..(13)
<223> OTHER INFORMATION: Xaa may be 6-aminohexanoic acid
<220> FEATURE:
<221> NAME/KEY: misc_feature
<222> LOCATION: (14)..(14)
<223> OTHER INFORMATION: Xaa may be beta-alanine

<400> SEQUENCE: 30

Arg Gly Arg Arg Gly Arg Arg Gly Arg Arg Gly Arg Xaa Xaa
1               5                   10

<210> SEQ ID NO 31
<211> LENGTH: 12
<212> TYPE: PRT
<213> ORGANISM: Artificial Sequence
```

```
<220> FEATURE:
<223> OTHER INFORMATION: (RFF)3RXB cell penetrating peptide
<220> FEATURE:
<221> NAME/KEY: misc_feature
<222> LOCATION: (11)..(11)
<223> OTHER INFORMATION: Xaa may be 6-aminohexanoic acid
<220> FEATURE:
<221> NAME/KEY: misc_feature
<222> LOCATION: (12)..(12)
<223> OTHER INFORMATION: Xaa may be beta-alanine

<400> SEQUENCE: 31

Arg Phe Phe Arg Phe Phe Arg Phe Phe Arg Xaa Xaa
1               5                   10

<210> SEQ ID NO 32
<211> LENGTH: 11
<212> TYPE: PRT
<213> ORGANISM: Artificial Sequence
<220> FEATURE:
<223> OTHER INFORMATION: (RFF)3RG cell penetrating peptide

<400> SEQUENCE: 32

Arg Phe Phe Arg Phe Phe Arg Phe Phe Arg Gly
1               5                   10

<210> SEQ ID NO 33
<211> LENGTH: 7
<212> TYPE: PRT
<213> ORGANISM: Artificial Sequence
<220> FEATURE:
<223> OTHER INFORMATION: (R)6G cell penetrating peptide

<400> SEQUENCE: 33

Arg Arg Arg Arg Arg Arg Gly
1               5

<210> SEQ ID NO 34
<211> LENGTH: 13
<212> TYPE: PRT
<213> ORGANISM: Artificial Sequence
<220> FEATURE:
<223> OTHER INFORMATION: (RXR)4G cell penetrating peptide
<220> FEATURE:
<221> NAME/KEY: misc_feature
<222> LOCATION: (2)..(2)
<223> OTHER INFORMATION: Xaa may be 6-aminohexanoic acid
<220> FEATURE:
<221> NAME/KEY: misc_feature
<222> LOCATION: (5)..(5)
<223> OTHER INFORMATION: Xaa may be 6-aminohexanoic acid
<220> FEATURE:
<221> NAME/KEY: misc_feature
<222> LOCATION: (8)..(8)
<223> OTHER INFORMATION: Xaa may be 6-aminohexanoic acid
<220> FEATURE:
<221> NAME/KEY: misc_feature
<222> LOCATION: (11)..(11)
<223> OTHER INFORMATION: Xaa may be 6-aminohexanoic acid

<400> SEQUENCE: 34

Arg Xaa Arg Arg Xaa Arg Arg Xaa Arg Arg Xaa Arg Gly
1               5                   10
```

```
<210> SEQ ID NO 35
<211> LENGTH: 6
<212> TYPE: PRT
<213> ORGANISM: Artificial Sequence
<220> FEATURE:
<223> OTHER INFORMATION: R6 cell penetrating peptide

<400> SEQUENCE: 35

Arg Arg Arg Arg Arg Arg
1               5
```

ANTISENSE ANTIBACTERIAL COMPOUNDS AND METHODS

CROSS-REFERENCE TO RELATED APPLICATIONS

This application is a divisional of U.S. application Ser. No. 16/064,306, filed Jun. 20, 2018, which is a national phase application under 35 U.S.C. § 371 of International Application No. PCT/US2016/068376, filed Dec. 22, 2016, which claims the benefit of priority to U.S. Provisional Application No. 62/387,178, filed Dec. 23, 2015, each of which is herein incorporated by reference in its entirety.

GOVERNMENT SUPPORT CLAUSE

This invention was made with government support under grant number AI111753 awarded by The National Institutes of Health. The government has certain rights in the invention.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is UTSDP2967USD1.txt. The text file is about 14 KB, was created on Oct. 10, 2021, and is being submitted electronically via EFS-Web.

BACKGROUND

Technical Field

The present disclosure includes antisense oligomers targeted against bacterial mRNAs and other macromolecules involved in a biochemical pathway and/or cellular process, and related compositions and methods of using the oligomers and compositions to treat an infected mammalian subject, for example, as primary antimicrobials or as adjunctive therapies with classic antimicrobials.

Description of the Related Art

Currently, there are several types of antibiotic compounds in use against bacterial pathogens and these compounds act through a variety of anti-bacterial mechanisms. For example, beta-lactam antibiotics, such as penicillin and cephalosporin, act to inhibit the final step in peptidoglycan synthesis. Glycopeptide antibiotics, including vancomycin and teichoplanin, inhibit both transglycosylation and transpeptidation of muramyl-pentapeptide, again interfering with peptidoglycan synthesis. Other well-known antibiotics include the quinolones, which inhibit bacterial DNA replication, inhibitors of bacterial RNA polymerase, such as rifampin, and inhibitors of enzymes in the pathway for production of tetrahydrofolate, including the sulfonamides.

Some classes of antibiotics act at the level of protein synthesis. Notable among these are the aminoglycosides, such as kanamycin and gentamicin. This class of compounds targets the bacterial 30S ribosome subunit, preventing the association with the 50S subunit to form functional ribosomes. Tetracyclines, another important class of antibiotics, also target the 30S ribosome subunit, acting by preventing alignment of aminoacylated tRNAs with the corresponding mRNA codon. Macrolides and lincosamides, another class of antibiotics, inhibit bacterial synthesis by binding to the 50S ribosome subunit, and inhibiting peptide elongation or preventing ribosome translocation.

Despite impressive successes in controlling or eliminating bacterial infections by antibiotics, the widespread use of antibiotics both in human medicine and as a feed supplement in poultry and livestock production has led to drug resistance in many pathogenic bacteria. Antibiotic resistance mechanisms can take a variety of forms. One of the major mechanisms of resistance to beta lactams, particularly in Gram-negative bacteria, is the enzyme beta-lactamase, which renders the antibiotic inactive by cleaving the lactam ring. Likewise, resistance to aminoglycosides often involves an enzyme capable of inactivating the antibiotic, in this case by adding a phosphoryl, adenyl, or acetyl group. Active efflux of antibiotics is another way that many bacteria develop resistance. Genes encoding efflux proteins, such as the tetA, tetG, tetL, and tetK genes for tetracycline efflux, have been identified. A bacterial target may develop resistance by altering the target of the drug. For example, the so-called penicillin binding proteins (PBPs) in many beta-lactam resistant bacteria are altered to inhibit the critical antibiotic binding to the target protein. Resistance to tetracycline may involve, in addition to enhanced efflux, the appearance of cytoplasmic proteins capable of competing with ribosomes for binding to the antibiotic. For those antibiotics that act by inhibiting a bacterial enzyme, such as for sulfonamides, point mutations in the target enzyme may confer resistance.

*Klebsiella pneumoniae* is found in the normal flora of the mouth, skin and intestines. However, it can cause severe lung problems if aspirated, and is a significant cause of hospital-acquired infections. *Klebsiella* can also cause infections in the urinary tract, lower biliary tract, and surgical wound sites, among other sides. The range of clinical diseases includes pneumonia, thrombophlebitis, urinary tract infection, cholecystitis, diarrhea, upper respiratory tract infection, wound infection, osteomyelitis, meningitis, and bacteremia, and septicemia. *Klebsiella* species are often resistant to multiple antibiotics. In fact, the spread of carbapenem-resistant Enterobacteriaceae (CRE) (including *K. pneumoniae*) has happened worldwide, including in the U.S. where carbapenemase-producing CRE has now been reported in most states.

*Pseudomonas aeruginosa* is a common Gram-negative bacterium that is found in soil, water, skin flora, and most man-made environments throughout the world. But it can cause serious disease in humans. For example, if *Pseudomonas* infections occur in critical body organs, such as the lungs, the urinary tract, and kidneys, the results can be fatal. It is also the major pathogen associated with lung infections in cystic fibrosis. CF patients typically become infected with strains of *Pseudomonas aeruginosa* from the environment, after which they evolve in the CF lung. Eighty percent of CF patients are infected with *Pseudomonas aeruginosa* by adulthood and chronic lung infections with this pathogen are the primary cause of morbidity and mortality. In the CF patient, complete eradication of *Pseudomonas aeruginosa* is rarely achieved. *Pseudomonas aeruginosa* is naturally resistant to many antibiotics and is becoming increasingly resistant to previously effective antibiotics. Multi-drug resistant isolates of *Pseudomonas aeruginosa* are now common in both CF and non-CF patients, leaving virtually no therapeutic options.

*Acinetobacter baumannii* is a ubiquitous organism that has emerged over the years to be a significant cause of hospital-acquired infections. This change in epidemiology is especially concerning given that *A. baumannii* has become one of the most antibiotic-resistant Gram-negative pathogens that the medical community faces world-wide. The rapid increase in multi-drug resistance in *A. baumannii* has left few therapeutic choices for the treating physician. Drugs such as colistin are now frequently used, although colistin-resistant strains have appeared. *Acinetobacter baumannii* can cause a variety of clinical infections, with pneumonia being one of the most frequent.

*Escherichia coli* normally inhabits the large intestine of humans as a commensal organism. However, it can also cause a variety of clinical infections, and is a leading cause of bacteremia. There has been an alarming increase in the number of antibiotic-resistant strains of *E. coli* isolated from patients with nosocomial and community-acquired bacteremia. It is not uncommon for strains to be resistant to multiple antibiotics.

The appearance of antibiotic resistance in many pathogenic bacteria, including cases involving multi-drug resistance (MDR), raises the fear of a post-antibiotic era in which many bacterial pathogens were simply untreatable by medical intervention. Thus, there is a need for antimicrobial agents that (i) are not subject to the principal types of antibiotic resistance currently hampering antibiotic treatment of bacterial infection, (ii) can be developed rapidly and with some reasonable degree of predictability as to target-bacteria specificity, (iii) are effective at low doses, and (iv) show few side effects.

BRIEF SUMMARY

Embodiments of the present disclosure relate, in part, to the discovery that the antisense targeting of bacterial genes associated with biochemical pathways, cellular processes, and/or antibiotic resistance can increase the antibiotic susceptibility of otherwise antibiotic-resistant pathogenic bacteria, and reduce the ability of certain pathogenic bacteria to grow. For example, the antisense targeting of genes associated with murein biosynthesis, cell division, global gene regulatory mechanisms, fatty acid biosynthesis, ribosomal proteins, ribosomal RNA (rRNA), DNA replication, transcription, translation initiation, lipopolysaccharide biosynthesis, nucleic acid biosynthesis, intermediary metabolism, RNA biosynthesis, protein biosynthesis, peptidoglycan biosynthesis, cellular energy homeostasis, aromatic compound biosynthesis, and antibiotic resistance have been shown to be bactericidal at clinically-relevant concentrations. The antisense oligomers described herein could thus find utility in the treatment of such bacteria, for instance, in combination with antibiotics or as standalone therapies.

Embodiments of the present disclosure therefore include a substantially uncharged antisense morpholino oligomer, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence of sufficient length and complementarity to specifically hybridize to a bacterial mRNA target sequence that encodes a protein associated with a biochemical pathway and/or cellular process, or a ribosomal RNA target sequence, as described herein. In some instances, the oligomer is conjugated to a cell-penetrating peptide (CPP).

In certain embodiments, the targeting sequence is selected from Tables 1A-B. In some embodiments, the oligomer is about 10-15 or about 11-12 nucleotide bases in length and has a targeting sequence selected from Tables 1A-B.

In certain embodiments, an antisense oligomer of the disclosure is of formula (I):

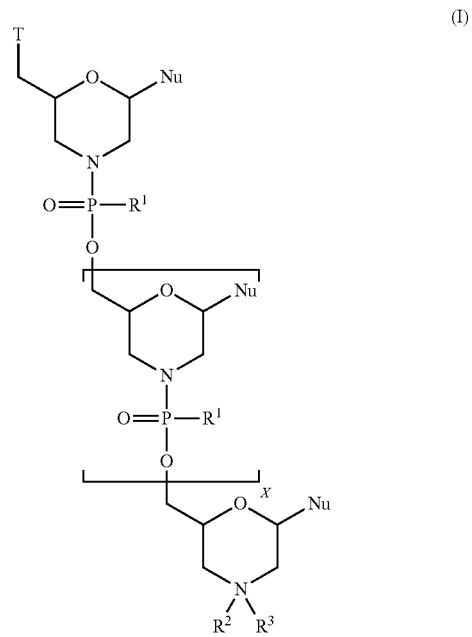

or a pharmaceutically acceptable salt thereof,
where each Nu is a nucleobase which taken together forms a targeting sequence;
X is an integer from 9 to 38;
T is selected from OH and a moiety of the formula:

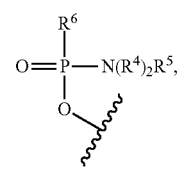

where each $R^4$ is independently $C_1$-$C_6$ alkyl, and $R^5$ is selected from an electron pair and H, and $R^6$ is selected from OH, —N($R^7$)$CH_2$C(O)$NH_2$, and a moiety of the formula:

where:
$R^7$ is selected from H and $C_1$-$C_6$ alkyl, and
$R^5$ is selected from G, —C(O)—$R^9$OH, acyl, trityl, and 4-methoxytrityl, where:
$R^9$ is of the formula —(O-alkyl)$_y$— wherein y is an integer from 3 to 10 and each of the y alkyl groups is independently selected from $C_2$-$C_5$ alkyl;
each instance of $R^5$ is —N($R^{10}$)$_2$$R^{11}$ wherein each $R^{10}$ is independently $C_1$-$C_6$ alkyl, and $R^{11}$ is selected from an electron pair and H;
$R^2$ is selected from H, G, acyl, trityl, 4-methoxytrityl, benzoyl, stearoyl, and a moiety of

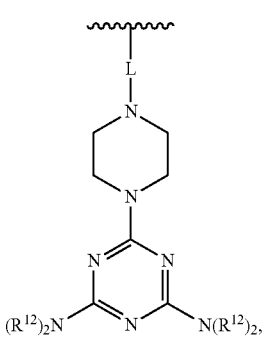

where L is selected from —C(O)(CH$_2$)$_6$C(O)— and —C(O)(CH$_2$)$_2$S$_2$(CH$_2$)$_2$C(O)—, and each R$^{12}$ is of the formula —(CH$_2$)$_2$OC(O)N(R$^{14}$)$_2$ wherein each R$^{14}$ is of the formula —(CH$_2$)$_6$NHC(=NH)NH$_2$; and R$^3$ is selected from an electron pair, H, and C$_1$-C$_6$ alkyl, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

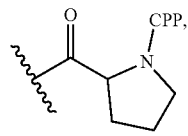

wherein the CPP is attached to the linker moiety by an amide bond at the CPP carboxy terminus, with the proviso that only one instance of G is present, wherein the targeting sequence specifically hybridizes to a bacterial mRNA target sequence that encodes a protein associated with a biochemical pathway and/or cellular process, or a ribosomal RNA target sequence, or a protein associated with antibiotic resistance, as described herein.

In some embodiments, the target sequence comprises a translational start codon of the bacterial mRNA and/or a sequence within about 30 bases upstream or downstream of the translational start codon of the bacterial mRNA.

In some embodiments, the protein associated with a biochemical pathway and/or cellular process is a fatty acid biosynthesis protein. In certain embodiments, the fatty acid biosynthesis protein is an acyl carrier protein. In certain embodiments, the acyl carrier protein is encoded by acpP. In some embodiments, the fatty acid biosynthesis protein is an acyl carrier protein synthase. In some embodiments, the acyl carrier protein synthase is encoded by fabB. In certain embodiments, the targeting sequence is set forth in SEQ ID NOS:1-3, comprises a fragment of at least 10 contiguous nucleotides of SEQ ID NOS: 1-3, or comprises a variant having at least 80% sequence identity to SEQ ID NOS: 1-3, where thymine bases (T) are optionally uracil bases (U).

In some embodiments, the protein associated with a biochemical pathway and/or cellular process is a peptidoglycan biosynthesis protein. In certain embodiments, the peptidoglycan biosynthesis protein is a UDP-N-acetylglucosamine 1-carboxyvinyltransferase. In particular embodiments, the UDP-N-acetylglucosamine 1-carboxyvinyltransferase is encoded by murA.

In certain embodiments, the protein associated with a biochemical pathway and/or cellular process is a ribosomal protein. In some embodiments, the ribosomal protein is a 50S ribosomal protein L28. In certain embodiments, the 50S ribosomal protein L28 is encoded by rpmB. In some embodiments, the ribosomal protein is a 30S ribosomal protein. In some embodiments, the 30S ribosomal protein is encoded by rpsJ.

In some embodiments, the protein associated with a biochemical pathway and/or cellular process is a ribosomal RNA (rRNA). In particular embodiments, rRNA is selected from a 16S rRNA and a 23S rRNA.

In certain embodiments, the protein associated with a biochemical pathway and/or cellular process is a cell division protein. In particular embodiments, the cell division protein is a protein that assembles into a ring at the future site of the septum of bacterial cell division. In some embodiments, the protein that assembles into a ring at the future site of the septum of bacterial cell division is encoded by ftsZ.

In certain embodiments, the protein associated with a biochemical pathway and/or cellular process is a DNA or chromosomal replication protein. In some embodiments, DNA or chromosomal replication protein is a topoisomerase. In specific embodiments, the topoisomerase is encoded by gyrA. In some embodiments, DNA or chromosomal replication protein is a helicase. In some embodiments, the helicase is encoded by dnaB. In some embodiments, DNA or chromosomal replication protein is a DNA polymerase. In some embodiments, the DNA polymerase is encoded by polB.

In specific embodiments, the targeting sequence is set forth in SEQ ID NOS:4-20, comprises a fragment of at least 10 contiguous nucleotides of SEQ ID NOS: 4-20, or comprises a variant having at least 80% sequence identity to SEQ ID NOS: 4-20, where thymine bases (T) are optionally uracil bases (U).

Also included are pharmaceutical compositions, comprising a pharmaceutically acceptable carrier and an antisense oligomer described herein. Some pharmaceutical compositions further comprising an antimicrobial agent as described herein. Illustrative examples of antimicrobial agents include tobramycin, meropenem, and colistin, and combinations thereof.

Some embodiments include methods of reducing expression and activity of a protein associated with a biochemical pathway and/or cellular process in a bacterium, comprising contacting the bacterium with an antisense oligomer and/or a pharmaceutical composition described herein.

In certain embodiments, the bacterium is in a subject, and the method comprises administering the antisense oligomer to the subject. In some embodiments, the bacterium is selected from the genera *Klebsiella, Pseudomonas, Acinetobacter*, and *Escherichia*. In particular embodiments, the bacterium is an antibiotic-resistant strain of *Klebsiella, Pseudomonas, Acinetobacter*, or *Escherichia*. In some embodiments, the bacterium is a multi-drug resistant (MDR) strain of *Klebsiella, Pseudomonas, Acinetobacter*, or *Escherichia*. In specific embodiments, the bacterium is *Klebsiella pneumonia, Pseudomonas aeruginosa, Acinetobacter baumannii*, or *Escherichia coli*.

Some methods comprise administering the oligomer separately or concurrently with an antimicrobial agent, optionally where administration of the oligomer increases susceptibility of the bacterium to the antimicrobial agent.

In certain embodiments, the antimicrobial agent is selected from one or more of a @3-lactam antibiotic, an aminoglycoside antibiotic, and a polymyxin.

In some embodiments, the @-lactam antibiotic is selected from at least one of carbapenems, penicillin derivatives (penams), cephalosporins (cephems), and monobactams.

In particular embodiments, the carbapenem is selected from one or more of meropenem, imipenem, ertapenem, doripenem, panipenem, biapenem, razupenem, tebipenem, lenapenem, and tomopenem. In specific embodiments, the carbapenem is meropenem.

In certain embodiments, the aminoglycoside antibiotic is selected from one or more of tobramycin, gentamicin, kanamycin a, amikacin, dibekacin, sisomicin, netilmicin, neomycin B, neomycin C, neomycin E (paromomycin), and streptomycin. In specific embodiments, the aminoglycoside antibiotic is tobramycin.

In certain embodiments, the polymyxin is selected from one or more of colistin (polymyxin E), polysporin, neosporin, or polymyxin B. In specific embodiments, the polymyxin is colistin.

In some embodiments, the pi-lactam antibiotic is selected from at least one of meropenem, imipenem, ertapenem, doripenem, panipenem, biapenem, razupenem, tebipenem, lenapenem, tomopenem, cephalosporins (cephems), penicillin, penicillin derivatives (penams) and ampicillin.

In certain embodiments, the aminoglycoside antibiotic is selected from at least one of tobramycin, gentamicin, kanamycin a, amikacin, dibekacin, sisomicin, netilmicin, neomycin B, neomycin C, neomycin E (paromomycin), and streptomycin.

In some embodiments, the tetracycline antibiotic is selected from at least one of tetracycline, chlortetracycline, oxytetracycline, demeclocycline, lymecycline, meclocycline, methacycline, minocycline, rolitetracycline, and doxycyline.

In particular embodiments, the β-lactam antibiotic is selected from at least one of carbapenems, penicillin derivatives (penams), cephalosporins (cephems), and monobactams.

In some embodiments, the oligomer reduces the minimum inhibitory concentration (MIC) of the antimicrobial agent against the bacterium by at least about 10% relative to the antimicrobial agent alone.

In some embodiments, the oligomer increases the susceptibility of the bacterium to the antimicrobial agent by at least about 10% relative to the antimicrobial agent alone.

In certain embodiments, the combination of oligomer and the antimicrobial agent synergistically increases the susceptibility of the bacterium to the antibiotic relative to the oligomer and/or the microbial agent alone.

In certain embodiments, the antimicrobial agent and the antisense oligomer are administered separately. In various embodiments, the antimicrobial agent and the antisense oligomer are administered sequentially. In some embodiments, the antimicrobial agent and the antisense oligomer are administered concurrently.

BRIEF DESCRIPTION OF THE FIGURES

FIG. 1A shows an exemplary morpholino oligomer structure with a phosphorodiamidate linkage. FIGS. 1B-E show the repeating subunit segment of exemplary morpholino oligomers, designated B through E. FIGS. 1F-H show exemplary peptide PMO conjugates structures used in the exemplary PPMOs.

FIG. 2 shows a minimal inhibitory concentration (MIC) heatmap of PPMOs targeted against essential genes from *Klebsiella* pneumoniae.

FIG. 3 shows a MIC heatmap of PPMOs targeted against ribosomal RNA from *Klebsiella pneumoniae, Pseudomonas aeruginosa,* and *Acinetobacter baumannii.*

DETAILED DESCRIPTION

1. Definitions

Figure 1A:
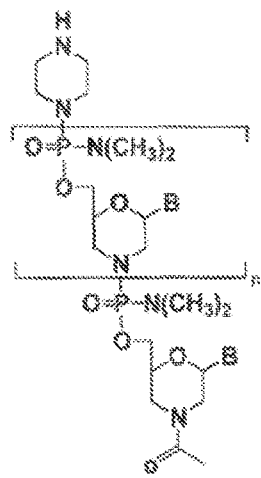
FIGS. 1A-H.
Figure 1B:
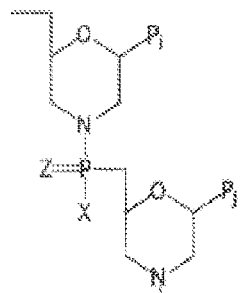
Figure 1C:
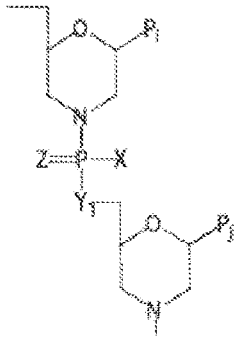
Figure 1D:
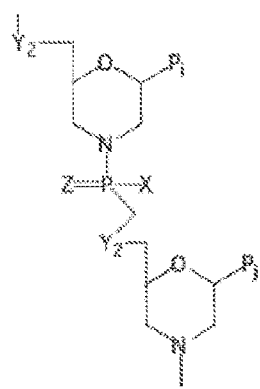
Figure 1E:
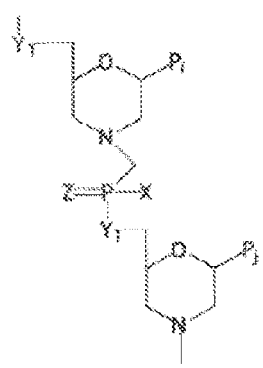

Unless defined otherwise, all technical and scientific terms used herein have the same meaning as commonly understood by those of ordinary skill in the art. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight, or length.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the terms "contacting a cell", "introducing" or "delivering" include delivery of the oligomers described herein into a cell by methods routine in the art, e.g., transfection (e.g., liposome, calcium-phosphate, polyethyleneimine), electroporation (e.g., nucleofection), microinjection), transformation, and administration.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". In some aspects, the peptides have the capability of inducing cell penetration within about or at least about 30%, 40%, 50%, 60%, 70%, 80%, 90%, or 100% of cells of a given population and/or allow macromolecular translocation to or within multiple tissues in vivo upon systemic administration. Particular examples of CPPs include "arginine-rich peptides." CPPs are well-known in the art and are disclosed, for example, in U.S. Application No. 2010/0016215 and International Patent Application Publication Nos. WO 2004/097017, WO 2009/005793, and WO 2012/150960, all of which are incorporated by reference in their entirety.

"An electron pair" refers to a valence pair of electrons that are not bonded or shared with other atoms.

"Homology" refers to the percentage number of amino acids that are identical or constitute conservative substitutions. Homology may be determined using sequence comparison programs such as GAP (Deveraux et al., 1984, Nucleic Acids Research 12, 387-395) or BLAST. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated polynucleotide" or "isolated oligomer," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

The term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or antisense compounds or compositions to produce or cause a greater physiological response (i.e., downstream effects) in a cell or a subject relative to the response caused by either no antisense compound or a control compound. Relevant physiological or cellular responses (in vivo or in vitro) will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and ranges between and above 1), e.g., 1.5, 1.6, 1.7, 1.8) the amount produced by no antisense compound (the absence of an agent) or a control compound. The term "reduce" or "inhibit" may relate generally to the ability of one or more antisense compounds or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in bacterial cell growth, reductions in the minimum inhibitory concentration (MIC) of an antimicrobial agent, and others. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers and ranges in between.

As used herein, an "antisense oligomer," "oligomer," or "oligomer" refers to a linear sequence of nucleotides, or nucleotide analogs, which allows the nucleobase to hybridize to a target sequence in an RNA by Watson-Crick base pairing, to form an oligomer:RNA heteroduplex within the target sequence. The terms "antisense oligomer," "antisense oligomer," "oligomer," and "compound" may be used interchangeably to refer to an oligomer. The cyclic subunits may be based on ribose or another pentose sugar or, in certain embodiments, a morpholino group (see description of morpholino oligomers below).

The term "oligomer," "oligomer," or "antisense oligomer" also encompasses an oligomer having one or more additional moieties conjugated to the oligomer, e.g., at its 3'- or 5'-end, such as a polyethylene glycol moiety or other hydrophilic polymer, e.g., one having 10-100 monomeric subunits, which may be useful in enhancing solubility, or a moiety such as a lipid or peptide moiety that is effective to enhance the uptake of the compound into target bacterial cells and/or enhance the activity of the compound within the cell, e.g., enhance its binding to a target polynucleotide.

A "nuclease-resistant" oligomers refers to one whose backbone is substantially resistant to nuclease cleavage, in non-hybridized or hybridized form; by common extracellular and intracellular nucleases in the body or in a bacterial cell (for example, by exonucleases such as 3'-exonucleases, endonucleases, RNase H); that is, the oligomer shows little or no nuclease cleavage under normal nuclease conditions to which the oligomer is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligomer and the complementary portion of a target RNA.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligomer. Exemplary analogs include hypoxanthine (the base component of the nucleoside inosine); 2,6-diaminopurine; 5-methyl cytosine; C5-propynyl-modified pyrimidines; 9-(aminoethoxy)phenoxazine (G-clamp) and the like.

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligomer.

An oligomer "specifically hybridizes" to a target sequence if the oligomer hybridizes to the target under physiological conditions, with a Tm substantially greater than 40° C. or 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

As used herein, "sufficient length" includes an antisense oligomer that is complementary to at least about 8, more typically about 8-10, 8-11, 8-12, 8-13, 8-14, 8-15, 8-16, 8-17, 8-18, 8-19, 8-20, 8-30, 8-40, or 10-11, 10-12, 10-13, 10-14, 10-15, 10-16, 10-17, 10-18, 10-19, 10-20, 10-30, 10-40 (including all integers and ranges in between) contiguous or non-contiguous nucleobases in a region of a bacterial mRNA target sequence or a bacterial rRNA target sequence. An antisense oligomer of sufficient length has at least a minimal number of nucleotides to be capable of specifically hybridizing to a region of the bacterial mRNA or rRNA target. Preferably an oligomer of sufficient length is from 8 to 30 nucleotides in length, for example, about 10-20 nucleotides in length.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, 1) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

A "subject" or a "subject in need thereof" includes a mammalian subject such as a human subject.

The terms "TEG," "EG3," or "triethylene glycol tail" refer to triethylene glycol moieties conjugated to the oligomer, e.g., at its 3'- or 5'-end. For example, in some embodiments, "TEG" includes, for example, wherein T of the compound of formula (I), (II), or (III) is of the formula:

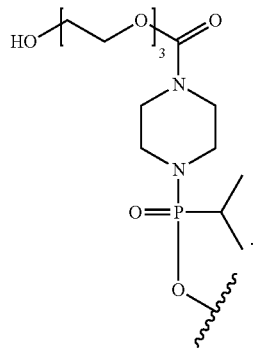

The term "pip-PDA" refers to a 5' terminal piperazine-phosphorodiamidate moiety that connects a G group, where the G group comprises a cell-penetrating peptide (CPP) and linker moiety further discussed below, to the 5'end of the oligomer by way of an amide bond between the G group linker and the piperazinyl nitrogen. For example, in some embodiments, "pip-PDA" includes wherein T of the compound of formula (I) or (II) is of the formula:

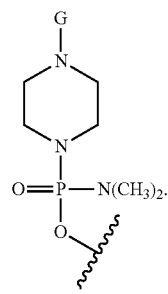

The term "target sequence" refers to a portion of the target RNA, for example, a bacterial mRNA or rRNA, against which the antisense oligomer is directed, that is, the sequence to which the oligomer will hybridize by Watson-Crick base pairing of a complementary sequence. In certain embodiments, the target sequence may be a contiguous region of the translation initiation region of a bacterial mRNA or a ribosomal RNA.

The term "targeting sequence" or "antisense targeting sequence" refers to the sequence in an oligomer that is complementary or substantially complementary to the target sequence in the RNA, e.g., the bacterial mRNA, the bacterial rRNA. The entire sequence, or only a portion, of the antisense compound may be complementary to the target sequence. For example, in an oligomer of about 10-30 bases, about 6, 7, 8, 9, 10, 11, 12, 13, 14, 15, 16, 17, 18, 19, 20, 21, 22, 23, 24, 25, 26, 27, 28, or 29 of the bases may be targeting sequences that are complementary to the target region. Typically, the targeting sequence is formed of contiguous bases, but may alternatively be formed of non-contiguous sequences that when placed together, e.g., from opposite ends of the oligomer, constitute sequence that spans the target sequence.

A "targeting sequence" may have "near" or "substantial" complementarity to the target sequence and still function for the purpose of the present disclosure, that is, still be "complementary." Preferably, the oligomer analog compounds employed in the present disclosure have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

As used herein, the term "quantifying", "quantification" or other related words refer to determining the quantity, mass, or concentration in a unit volume, of a nucleic acid, polynucleotide, oligomer, peptide, polypeptide, or protein.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

II. Bacterial Targeting Sequences

Certain embodiments relate to antisense oligomers, and related compositions and methods, which are of sufficient length and complementarity to specifically hybridize to a bacterial mRNA target sequence that encodes a gene in a biochemical pathway and/or cellular process, or a ribosomal RNA target sequence. General examples include: murein biosynthesis, cell division, global gene regulatory mechanisms, fatty acid biosynthesis, ribosomal proteins, ribosomal RNA (rRNA), DNA/chromosomal replication, transcription, translation initiation, lipopolysaccharide biosynthesis, nucleic acid biosynthesis, intermediary metabolism, RNA biosynthesis, protein biosynthesis, peptidoglycan biosynthesis, cellular energy homeostasis, aromatic compound biosynthesis, and antibiotic resistance. Particular examples of genes in biochemical pathways and cellular processes include: rpsJ and rpmB (ribosomal proteins); lpxC, waaC, waaG, waaA, waaF, lpxA, and lpxB (lipopolysaccharide biosynthesis); murA (formerly known as murZ), mraY, murC, murB, murE, murF, and murG (peptidoglycan biosynthesis); fabG, acpP, accA, fabB, accB, and fabZ (fatty acid biosynthesis); adk (cellular energy homeostasis); infA (transcription antitermination and/or protein synthesis); ftsZ (cell division); rpoD (RNA synthesis); aroC (aromatic compound biosynthesis); gyrA, dnaB, pol B (chromosomal and DNA replication). Examples of antibiotic resistance genes include blaT, cml, and adeA. In some embodiments, the rRNA target sequence or mRNA target sequence that encodes the gene is from *Klebsiella*, e.g., *Klebsiella pneumoniae*. In some embodiments, the rRNA target sequence or the mRNA target sequence that encodes the gene is from *Pseudomonas*, e.g., *Pseudomonas aeruginosa*. In some embodiments, the rRNA target sequence or the mRNA target sequence that encodes the gene is from *Acinetobacter*, e.g., *Acinetobacter baumannii*. In some embodiments, the rRNA target sequence or the mRNA target sequence that encodes the gene is from *Escherichia*, e.g., *E. coli*.

In some embodiments, the bacterial target is a gene or protein that is associated with biosynthesis of fatty acids. General examples of proteins associated with fatty acid biosynthesis include: acyl carrier protein (ACP), such as AcpP, that plays an essential role in stabilizing and shuttling the intermediate fatty acid chain to each of the enzymes in the fatty acid synthase complex; acyl carrier protein synthase (AcpS), an enzyme that transfers the 4'-phosphopantetheine prosthetic group to apo-ACP to form the functional holo-ACP; acetyl-CoA carboxylase, an enzyme composed of four proteins that catalyzes the conversion of acetyl-CoA to malonyl-CoA in the first committed step of fatty acid biosynthesis: AccA (carboxyltransferase alpha subunit catalyzing the transfer of the carboxyl group from biotin to acetyl-CoA to form malonyl-CoA), AccB (biotin carboxyl carrier protein, BCCP, carrying the biotin prosthetic group covalently attached to a lysine residue proximal to the carboxyl terminus), AccC (biotin carboxylase catalyzing the carboxylation of protein bound biotin with bicarbonate), AccD (carboxyltransferase beta subunit catalyzing the transfer of the carboxyl group from biotin to acetyl-CoA to form malonyl-CoA); fatty acid biosynthesis (Fab) enzymes, such as FabA, FabB, FabI, FabF, FabD, FabH, FabG and FabZ, that each catalyze either elongation or tailoring steps on the growing fatty acid chain. Particular examples of genes associated with fatty acid biosynthesis include acpP, the carboxyltransferase alpha subunit accA, and the acyl carrier protein synthasefabB.

Specific embodiment therefore relate to antisense oligomers, and related compositions and methods, which are of sufficient length and complementarity to specifically hybridize to an mRNA target sequence of a bacterial acpP gene, which encodes an acyl carrier protein (ACP). In some embodiments, the acpP gene is from *Klebsiella*, e.g., *Klebsiella pneumoniae*. In some embodiments, the acpP gene is from *Pseudomonas*, e.g., *Pseudomonas aeruginosa*. In some embodiments, the acpP gene is from *Acinetobacter*, e.g., *Acinetobacter baumannii*. In some embodiments, the acpP gene is from *Escherichia*, e.g., *E. coli*.

Certain embodiment relate to antisense oligomers, and related compositions and methods, which are of sufficient length and complementarity to specifically hybridize to an mRNA target sequence of a bacterial fabB gene. In some embodiments, the fabB gene is from *Klebsiella*, e.g., *Klebsiella pneumoniae*. In some embodiments, the fabB gene is from *Pseudomonas*, e.g., *Pseudomonas aeruginosa*. In some embodiments, the fabB gene is from *Acinetobacter*, e.g., *Acinetobacter baumannii*. In some embodiments, the fabB gene is from *Escherichia*, e.g., *E. coli*.

The bacterial cell wall peptidoglycan is an essential cellular component involved in the maintenance of shape and protection from osmotic shock lysis. Typically, peptidoglycan is assembled from a basic building block composed of N-acetylglucosamine (GlcNAc) and N-acetylmuramic acid with an attached pentapeptide. In some embodiments, the bacterial target is a gene or protein that is associated with peptidoglycan biosynthesis. A particular example of a gene associated with peptidoglycan biosynthesis include murA (formerly known as murZ), which encodes a UDP-N-acetylglucosamine 1-carboxyvinyltransferase, which catalyzes the first committed step of peptidoglycan biosynthesis. The enzyme catalyzes the transfer of enolpyruvate from phosphoenolpyruvate to the 3-OH of UDP-N-acetylglucosamine. In some embodiments, the murA gene is from *Klebsiella*, e.g., *Klebsiella pneumoniae*. In some embodiments, the murA gene is from *Pseudomonas*, e.g., *Pseudomonas aeruginosa*. In some embodiments, the murA gene is from *Acinetobacter*, e.g., *Acinetobacter baumanii*. In some embodiments, the murA gene is from *Escherichia*, e.g., *E. coli*.

The ribosome is crucial for translation of mRNA molecules into proteins. In some embodiments, the bacterial target is a gene or protein that is associated with ribosomal proteins. A particular example of a gene associated with ribosomal proteins is rpmB, a 50S ribosomal protein L28 essential for ribosome assembly and translation. Another example of a gene associated with ribosomal proteins is rpsJ, a 30S ribosomal protein. In some embodiments, the rpmB or rpsJ gene is from *Klebsiella*, e.g., *Klebsiella pneumoniae*. In some embodiments, the rpmB or rpsJ gene is from *Pseudomonas*, e.g., *Pseudomonas aeruginosa*. In some embodiments, the rpmB or rpsJ gene is from *Acinetobacter*, e.g., *Acinetobacter baumanii*. In some embodiments, the rpmB or rpsJ gene is from *Escherichia*, e.g., *E. coli*.

In some embodiments, the bacterial target is a ribosomal RNA (rRNA). Examples of rRNA include 5S, 16S, and 23S rRNA. In some embodiments, the rRNA (e.g., 5S, 16S, 23S) is from *Klebsiella*, e.g., *Klebsiella pneumoniae*. In some embodiments, the rRNA (e.g., 5S, 16S, 23S) is from *Pseudomonas*, e.g., *Pseudomonas aeruginosa*. In some embodiments, the rRNA (e.g., 5S, 16S, 23S) is from *Acinetobacter*, e.g., *Acinetobacter baumanii*. In some embodiments, the rRNA (e.g., 5S, 16S, 23S) is from *Escherichia*, e.g., *E. coli*.

In some embodiments, the bacterial target is a gene or protein that is associated with cellular energy homeostasis. A particular example of a gene associated with cellular energy homeostasis includes an adenylate kinase (adk) gene, which encodes a phosphotransferase enzyme that catalyzes the interconversion of adenine nucleotides.

In some embodiments, the bacterial target is a gene or protein that is associated with transcription antitermination and/or protein biosynthesis. A particular example of a gene associated with transcription antitermination and/or protein biosynthesis includes translation initiation factor IF1. IF1, encoded by infA, is a protein containing an S1-like domain that may play a role in binding and melting nucleic acid secondary structure and transcription antitermination. Other functions may also include increasing the rate of 70S ribosome dissociation and subunit association and involvement in the fidelity of translation initiation through stimulation of other translation initiation factor activities, such as IF2 and IF3.

In some embodiments, the bacterial target is a gene or protein that is associated with cell division. A particular example of a gene associated with cell division includes aftsZ gene, which encodes a protein that assembles into a ring at the future site of the septum of bacterial cell division. This is a prokaryotic homologue to the eukaryotic protein tubulin. In some embodiments, the ftsZ gene is from *Klebsiella*, e.g., *Klebsiella pneumoniae*. In some embodiments, the ftsZ gene is from *Pseudomonas*, e.g., *Pseudomonas aeruginosa*. In some embodiments, the ftsZ gene is from *Acinetobacter*, e.g., *Acinetobacter baumanii*. In some embodiments, the ftsZ gene is from *Escherichia*, e.g., *E. coli*.

In some embodiments, the bacterial target is a gene or protein that is associated with DNA or chromosomal replication. One example of a gene associated with DNA or chromosomal replication is gyrA, which encodes a topoisomerase. Another example of a gene associated with DNA or chromosomal replication is dnaB, which encodes a helicase. Another example of a gene associated with DNA or chromosomal replication is polB, which encodes a DNA polymerase. In some embodiments, the gyrA or dnaB or polB gene is from *Klebsiella*, e.g., *Klebsiella pneumoniae*. In some embodiments, the gyrA or dnaB or polB gene is from *Pseudomonas*, e.g., *Pseudomonas aeruginosa*. In some embodiments, the gyrA or dnaB or polB gene is from *Acinetobacter*, e.g., *Acinetobacter baumanii*. In some embodiments, the gyrA or dnaB or polB gene is from *Escherichia*, e.g., *E. coli*.

In some embodiments, the bacterial target is a gene or protein that is associated with lipopolysaccharide biosynthesis. One example of a gene associated with lipopolysaccharide biosynthesis is IpxC, which encodes an N-acetylglucosamine deacetylase. In some embodiments, the IpxC, gene is from *Klebsiella*, e.g., *Klebsiella pneumoniae*. In some embodiments, the IpxC gene is from *Pseudomonas*, e.g., *Pseudomonas aeruginosa*. In some embodiments, the IpxC gene is from *Acinetobacter*, e.g., *Acinetobacter baumanii*. In some embodiments, the IpxC gene is from *Escherichia*, e.g., *E. coli*.

In some embodiments, the bacterial target is a gene or protein that is associated with RNA synthesis. A particular example of a gene associated with RNA synthesis includes an rpoD gene, which encodes a sigma D (sigma 70) factor of RNA polymerase that allows binding of the polymerase to gene promoters and is important for transcribing most genes in growing cells. Genes recognized by this sigma factor have promoter consensus sequences centered at 10 and 35 nucleotides before the start of transcription. In some embodiments, the rpoD gene is from *Klebsiella*, e.g., *Klebsiella pneumoniae*. In some embodiments, the rpoD gene is from *Pseudomonas*, e.g., *Pseudomonas aeruginosa*. In some embodiments, the rpoD gene is from *Acinetobacter*, e.g., *Acinetobacter baumanii*. In some embodiments, the rpoD gene is from *Escherichia*, e.g., *E. coli*.

The biosynthesis of aromatic compounds is important for the growth and survival of bacterial cells. The shikimate pathway is a biosynthetic route in microorganisms that lead to the synthesis of chorismic acid, a central precursor for other aromatic compounds. In some embodiments, the bacterial target is a gene or protein that is associated with aromatic compound biosynthesis. A particular example of a gene associated with aromatic compound biosynthesis includes an aroCgene, which encodes chorismate synthase (5-enolpyruvylshikimate-3-phosphate phospholyase), the final enzyme in the shikimate pathway that catalyzes the conversion of 5-enolpyruvylshikimate-3-phosphate to chorismic acid.

In some embodiments, the gene or protein is associated with resistance of the bacteria to at least one antimicrobial agent, i.e., an antibiotic resistance gene. General examples of antibiotic resistance genes include beta-lactamases, which can enzymatically deactivate certain antimicrobial agents, and proteins that increase the permeability or active efflux (pumping-out) of an antimicrobial agent. Particular examples of antibiotic resistance genes include TEM beta-lactamase (blaT), chloramphenicol resistance gene (cml), and resistance-nodulation-cell division (RND)-type multi-drug efflux pump subunit AdeA (adeA).

In certain embodiments, the target sequence contains all or a portion (e.g., 1 or 2 nucleotides) of a translational start codon of the bacterial mRNA. In some embodiments, the target sequence contains a sequence that is about or within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 bases upstream or downstream of a translational start codon of the bacterial mRNA target sequence, including common and alternative start codons (e.g., AUG, GUG, UUG, AUU, CUG). For example, in particular embodiments, the 5'-end of the target sequence is the adenine, uracil, or guanine nucleotide (respectively) in an AUG start codon of the bacterial mRNA. In some embodiments, the 5'-end of the target sequence is the guanine, uracil, or guanine nucleotide (respectively) in a GUG start codon of the bacterial mRNA. In some embodiments, the 5'-end of the target sequence is the uracil, uracil, or guanine nucleotide (respectively) in a UUG start codon of the bacterial mRNA. In some embodiments, the 5'-end or 3-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 downstream of the last (third) nucleotide of a translational start codon of the bacterial mRNA. In some embodiments, the 5'-end or 3-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 upstream of the first nucleotide of a translational start codon of the bacterial mRNA.

Thus, in certain embodiments, antisense targeting sequences are designed to hybridize to a region of one or more of the target genes described herein. Selected antisense targeting sequences can be made shorter, e.g., about 8, 9, 10, 11, 12, 13, 14, or 15 bases, or longer, e.g., about 20, 30, or 40 bases, and include a small number of mismatches, as long as the sequence is sufficiently complementary to reduce transcription or translation upon hybridization to the target sequence, and optionally forms with the RNA a heteroduplex having a Tm of 45° C. or greater.

In certain embodiments, the degree of complementarity between the target sequence and antisense targeting sequence is sufficient to form a stable duplex. The region of complementarity of the antisense oligomers with the target RNA sequence may be as short as 8-9 bases, 8-10 bases, 8-11 bases, 8-12 bases, 10-11 bases, 10-12 bases, but can be 12-15 bases or more, e.g., 10-40 bases, 12-30 bases, 12-25 bases, 15-25 bases, 12-20 bases, or 15-20 bases, including all integers in between these ranges. An antisense oligomer of about 10-15 bases is generally long enough to have a unique complementary sequence. In certain embodiments, a minimum length of complementary bases may be required to achieve the requisite binding Tm, as discussed herein.

In certain embodiments, oligomers as long as 40 bases may be suitable, where at least a minimum number of bases, e.g., 10-12 bases, are complementary to the target sequence. In general, however, facilitated or active uptake in cells is optimized at oligomer lengths of less than about 30 or less than about 20 bases. Included are antisense oligomers that consist of about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to a target gene described herein.

In certain embodiments, antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo, and reduce expression of the targeted mRNA. Hence, certain oligomers may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligomer and the target sequence. Oligomer backbones that are less susceptible to cleavage by nucleases are discussed herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, for example, such that translation of the target RNA is reduced.

The stability of the duplex formed between an oligomer and a target sequence is a function of the binding Tm and the susceptibility of the duplex to cellular enzymatic cleavage. The Tm of an oligomer with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding Tm, with respect to a complementary-sequence RNA, of greater than body temperature and preferably greater than about 45° C. or 50° C. Tm's in the range 60-80° C. or greater are also included. According to well-known principles, the Tm of an oligomer, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer.

Tables 1A-B below show exemplary targeting sequences (in a 5'-to-3' orientation) of the antisense oligomers described herein.

TABLE 1A

Exemplary Fatty Acid Biosynthesis-Associated Targeting Sequences

| Target Gene | Targeting Sequence (TS)* | SEQ ID NO: |
| --- | --- | --- |
| acpP | CTC ATA CCT TG | 1 |
| acpP | TGC TCA TAC TC | 2 |
| fabB | CGT TTC ATT AA | 3 |

TABLE 1B

Exemplary targeting sequences associated with other biochemical pathways and/or cellular processes

| Target Gene | Targeting Sequence (TS)* | SEQ ID NO: |
| --- | --- | --- |
| murA | TTT ATC CAT TG | 4 |
| rpsJ | GCA TTT GAC CT | 5 |
| rpmB | GTC TAT TCT CC | 6 |
| rpmB | GAC ATG TCT AT | 7 |
| rpsJ | TGG TTC TGC AT | 8 |
| ftsZ | AGT TTC TCT CC | 9 |
| ftsZ | GTT CAA ACA TA | 10 |
| gyrA | CGC TCA TCT AA | 11 |
| dnaB | TTC CTG CCA TA | 12 |
| lpxC | TTT GAT CAT CG | 13 |
| 23S rRNA | AGT GCT CTA CC | 14 |
| 23S rRNA | GCC TGT TAT CC | 15 |
| 16S rRNA | CCA TGC AGC AC | 16 |
| 16S rRNA | TTG CGC TCG TT | 17 |
| 16S rRNA | GGC TGC TGG CA | 18 |
| rpoD | TCA TCT TTG CT | 19 |
| polB | AGT AAC TCC AC | 20 |

Certain antisense oligomers thus comprise, consist, or consist essentially of a targeting sequence in Tables 1A-B (e.g., SEQ ID NOS: 1-20) or a variant or contiguous or non-contiguous portion(s) thereof. For instance, certain antisense oligomers comprise about or at least about 6, 7, 8, 9, 10, 11, 12, 13, 14, 15, 16, 17, 18, 19, 20, 21, 22, 23, 24, 25, 26, or 27 contiguous or non-contiguous nucleotides of any of the targeting sequences in Tables 1A-B (e.g., SEQ ID NOS:1-20). For non-contiguous portions, intervening nucleotides can be deleted or substituted with a different nucleotide, or intervening nucleotides can be added. Additional examples of variants include oligomers having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of the targeting sequences in Tables 1A-B (e.g., SEQ ID NOS: 1-20).

The activity of antisense oligomers and variants thereof can be assayed according to routine techniques in the art (see, e.g., the Examples).

III. Antisense Oligomer Compounds

The antisense oligomers typically comprises a base sequence of sufficient length and complementarity to specifically hybridize to a bacterial mRNA target sequence that encodes a protein associated with a biochemical pathway and/or cellular process and thereby reduce expression (e.g., translation) of the protein, or a ribosomal RNA target sequence and thereby inhibit its interaction with other macromolecules. This requirement is optionally met when the oligomer compound has the ability to be actively taken up by bacterial cells, and once taken up, form a stable duplex (or heteroduplex) with the target mRNA or target rRNA, optionally with a Tm greater than about 40° C. or 45° C.

A. Antisense Oligomer Chemical Features

In certain embodiments, the backbone of the antisense oligomer is substantially uncharged, and is optionally recognized as a substrate for active or facilitated transport across a cell wall and/or cell membrane. The ability of the oligomer to form a stable duplex with the target RNA may also relate to other features of the backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell. Exemplary antisense oligomer targeting sequences are listed in Tables 1A-B (supra).

In certain embodiments, the antisense oligomer is a morpholino-based oligomer, for example, a phosphorodiamidate morpholino oligomer (PMO). Morpholino-based oligomers refer to an oligomer comprising morpholino subunits supporting a nucleobase and, instead of a ribose, contains a morpholine ring. Exemplary internucleoside linkages include, for example, phosphoramidate or phosphorodiamidate internucleoside linkages joining the morpholine ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligomer.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic internucleoside linkages of the morpholino-based oligomers described herein, one nitrogen is always pendant to the linkage chain. The second nitrogen, in a phosphorodiamidate linkage, is typically the ring nitrogen in a morpholine ring structure.

In particular embodiments, the morpholino subunits are joined by phosphorous-containing intersubunit linkages in accordance with the structure:

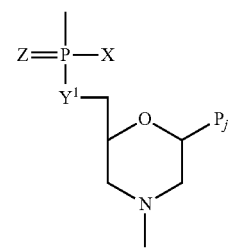

where $Y_1$=oxygen (O) or sulfur, nitrogen, or carbon; Z=oxygen or sulfur, preferably oxygen; Pj is a purine or pyrimidine base-pairing moiety effective to bind, by base-specific hydrogen bonding, to a base in a polynucleotide, and X is —NRR' where R and R' are the same or different and are either H or alkyl. In particular embodiments, X is —NRR', where R and R' are the same or different and are either H or methyl.

Also included are antisense oligomer that comprise a sequence of nucleotides of the formula in FIGS. 1A-1E. In FIG. 1A, B is a purine or pyrimidine base-pairing moiety effective to bind, by base-specific hydrogen bonding, to a base in a polynucleotide. $Y_1$ or $Y_2$ may be oxygen, sulfur, nitrogen, or carbon, preferably oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy include 1-6 carbon atoms. The Z moieties may be sulfur or oxygen, and are preferably oxygen.

Accordingly, various embodiments of the disclosure include a substantially uncharged antisense morpholino oligomer, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence of sufficient length and complementarity to specifically hybridize to a bacterial mRNA target sequence that encodes a protein associated with a biochemical pathway and/or cellular process, or a ribosomal RNA target sequence, as described herein. In some instances, the oligomer is conjugated to a cell-penetrating peptide (CPP).

In various aspects, an antisense oligomer of the disclosure includes a compound of formula (I):

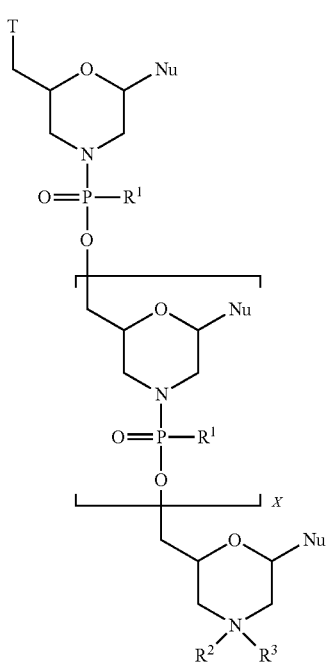

(I)

or a pharmaceutically acceptable salt thereof,
where each Nu is a nucleobase which taken together forms a targeting sequence;
X is an integer from 9 to 38;
T is selected from OH and a moiety of the formula:

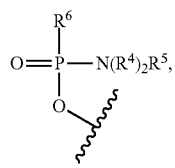

where each $R^4$ is independently $C_1$-$C_6$ alkyl, and $R^5$ is selected from an electron pair and H, and $R^6$ is selected from OH, —N($R^7$)CH$_2$C(O)NH$_2$, and a moiety of the formula:

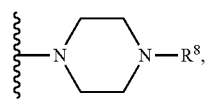

where:
  $R^7$ is selected from H and $C_1$-$C_6$ alkyl, and
  $R^8$ is selected from G, —C(O)—$R^9$OH, acyl, trityl, and 4-methoxytrityl, where:
    $R^9$ is of the formula —(O-alkyl)$_y$- wherein y is an integer from 3 to 10 and each of the y alkyl groups is independently selected from $C_2$-$C_5$ alkyl;
  each instance of $R^1$ is —N($R^{10}$)$_2$$R^{11}$ wherein each $R^{10}$ is independently $C_1$-$C_6$ alkyl, and $R^{11}$ is selected from an electron pair and H;
  $R^2$ is selected from H, G, acyl, trityl, 4-methoxytrityl, benzoyl, stearoyl, and a moiety of the formula:

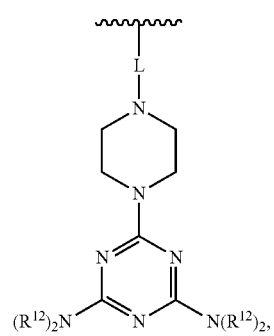

where L is selected from —C(O)(CH$_2$)$_6$C(O)— and —C(O)(CH$_2$)$_2$S$_2$(CH$_2$)$_2$C(O)—, and each $R^{12}$ is of the formula —(CH$_2$)$_2$OC(O)N($R^{14}$)$_2$ wherein each $R^{14}$ is of the formula —(CH$_2$)$_6$NHC(=NH)NH$_2$; and $R^3$ is selected from an electron pair, H, and $C_1$-$C_6$ alkyl, wherein G is a cell penetrating peptide ("CPP") and linker moiety selected from
—C(O)(CH$_2$)$_5$NH—CPP,    —C(O)(CH$_2$)$_2$NH—CPP,
—C(O)(CH$_2$)$_2$NHC(O)(CH$_2$)$_5$NH—CPP, and —C(O)CH$_2$NH—CPP, or G is of the formula:

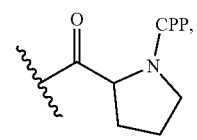

wherein the CPP is attached to the linker moiety by an amide bond at the CPP carboxy terminus, with the proviso that only one instance of G is present, wherein the targeting sequence specifically hybridizes to a bacterial mRNA target sequence that encodes a protein associated with a biochemical pathway and/or cellular process, or a rRNA target sequence.

In some embodiments, X is from 9 to 18. In certain embodiments, X is 9, 10, 11, 12, 13, 14, 15, 16, 17, 18, 19, 20, 21, 22, 23, 24, 25, 26, 27, 28, 29 or 30.

In certain embodiments, T is selected from:

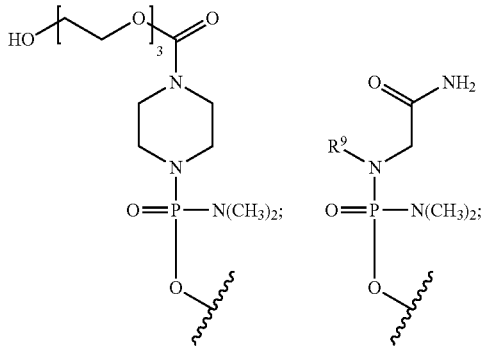

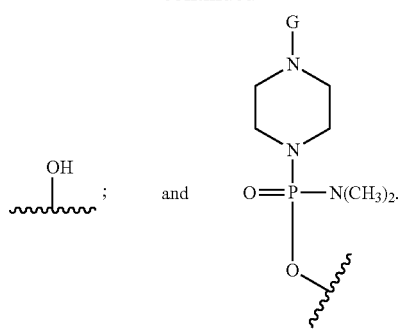

In some embodiments, R² is selected from H, G, acyl, trityl, 4-methoxytrityl, benzoyl, and stearoyl.

In various embodiments, T is selected from:

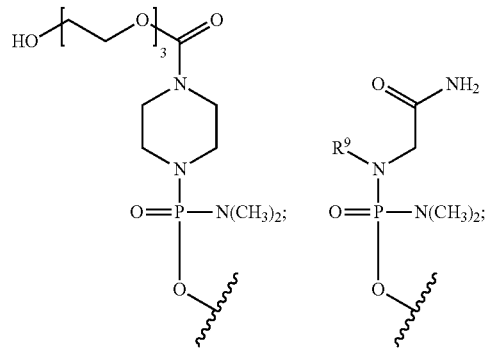

and, and R² is G.

In some embodiments, T is of the formula:

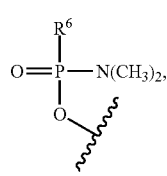

R⁶ is of the formula:

and R² is G.

In certain embodiments, T is of the formula:

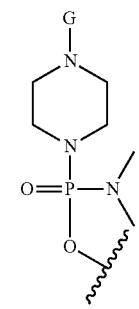

and R² is G.

In certain embodiments, T is of the formula:

and R² is G.

In some embodiments, R² is G or T is of the formula:

In some embodiments, R² is selected from H, acyl, trityl, 4-methoxytrityl, benzoyl, and stearoyl.

In various embodiments, R² is selected from H or G, and R³ is selected from an electron pair or H. In a particular embodiment, R² is G. In some embodiments, R² is H or acyl. In some embodiments, each R¹ is —N(CH₃)₂. In some embodiments, at least one instance of R¹ is —N(CH₃)₂. In certain embodiments, each instance of R¹ is —N(CH₃)₂.

In various embodiments of the disclosure, an antisense oligomer of the disclosure includes a compound of formula (II):

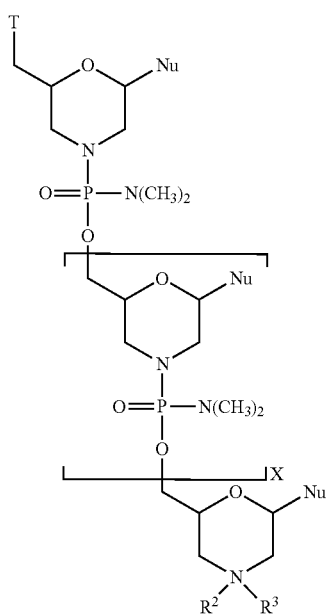
(II)

or a pharmaceutically acceptable salt thereof, where each Nu is a nucleobase which taken together forms a targeting sequence;

X is an integer from 9 to 28;

T is selected from:

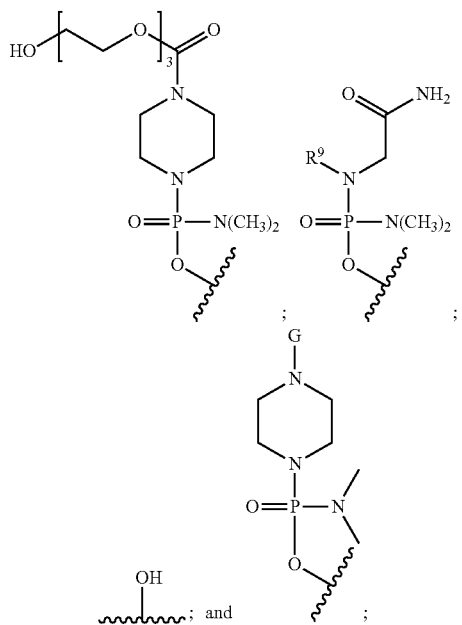

$R^2$ is selected from H, G, acyl, trityl, 4-methoxytrityl, benzoyl, and stearoyl; and $R^3$ is selected from an electron pair, H, and $C_1$-$C_6$ alkyl, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

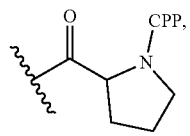

wherein the CPP is attached to the linker moiety by an amide bond at the CPP carboxy terminus, with the proviso that only one instance of G is present. In some embodiments, T is TEG as defined above, $R^2$ is G, and $R^3$ is an electron pair or H. In certain embodiments, $R^2$ is selected from H, acyl, trityl, 4-methoxytrityl, benzoyl, and stearoyl and T is of the formula:

In some embodiments, $R^2$ is G or T is of the formula:

In various aspects, an antisense oligomer of the disclosure includes a compound of formula (III):

(III)

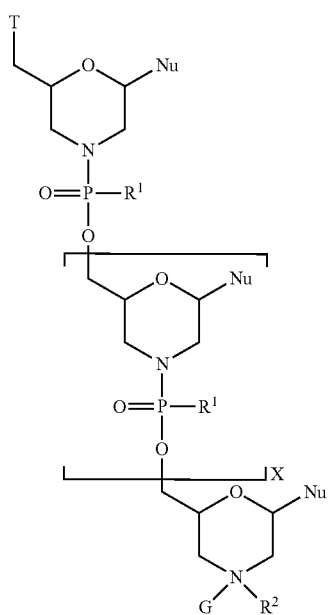

or a pharmaceutically acceptable salt thereof,
where each Nu is a nucleobase which taken together forms a targeting sequence;
X is an integer from 9 to 28;
T is selected from:

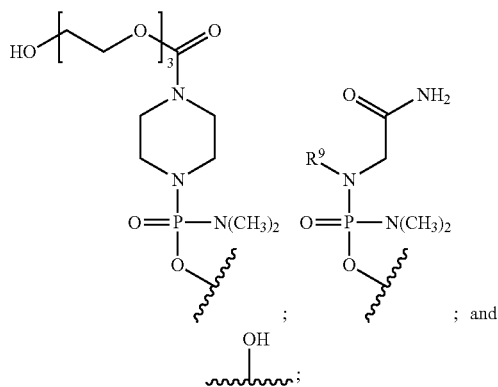

each instance of $R^1$ is —N($R^{10}$)$_2$$R^{11}$ wherein each $R^{10}$ is independently $C_1$-$C_6$ alkyl, and $R^{11}$ is selected from an electron pair and H;
$R^2$ is selected from an electron pair, H, and $C_1$-$C_6$ alkyl; and
G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

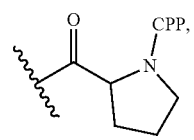

wherein the CPP is attached to the linker moiety by an amide bond at the CPP carboxy terminus. In some embodiments, at least one instance of $R^1$ is —N(CH$_3$)$_2$. In certain embodiments, each instance of $R^1$ is —N(CH$_3$)$_2$.

In various aspects, an antisense oligomer of the disclosure includes a compound of formula (IV):

(IV)

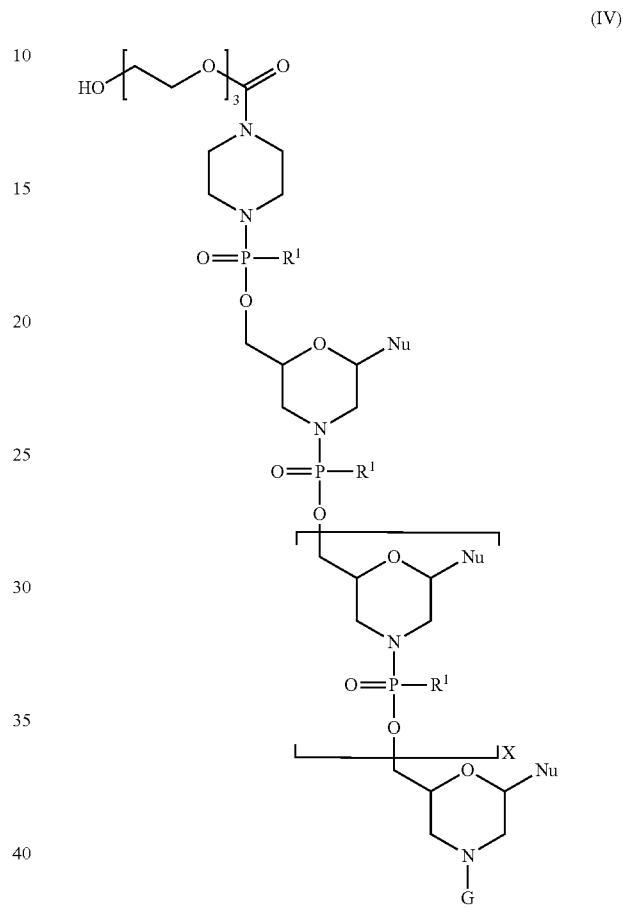

or a pharmaceutically acceptable salt thereof, wherein:
X is an integer from 9 to 28;
each Nu is a nucleobase which taken together forms a targeting sequence;
each instance of $R^1$ is —N($R^{10}$)$_2$$R^{11}$ wherein each $R^{10}$ is independently $C_1$-$C_6$ alkyl, and $R^{11}$ is selected from an electron pair and H; and
G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

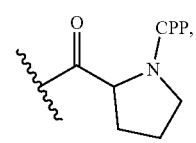

wherein the CPP is attached to the linker moiety by an amide bond at the CPP carboxy terminus. In some embodiments, at least one instance of $R^1$ is —N(CH$_3$)$_2$. In certain embodiments, each instance of $R^1$ is —N(CH$_3$)$_2$.

In various aspects, an antisense oligomer of the disclosure can be a compound of formula (V):

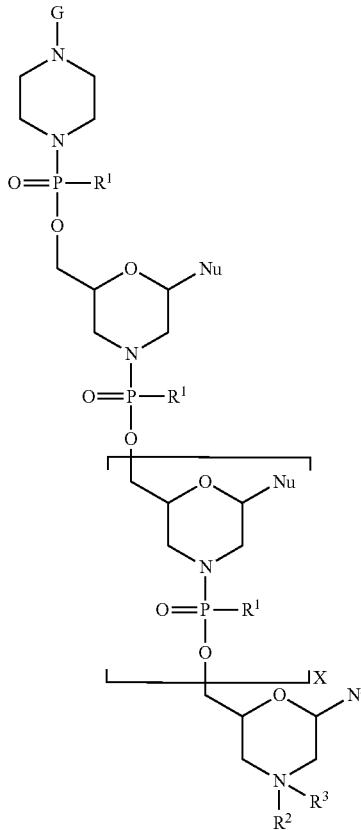

(V)

wherein:
X is an integer from 9 to 18;
each Nu is a nucleobase which taken together forms a targeting sequence;
each instance of $R^1$ is —N($R^{10}$)$_2$$R^{11}$ wherein each $R^{10}$ is independently $C_1$-$C_6$ alkyl, and $R^{11}$ is selected from an electron pair and H;
$R^2$ is selected from H, trityl, 4-methoxytrityl, acyl, benzoyl, and stearoyl; and
$R^3$ is selected from an electron pair, H, and $C_1$-$C_6$ alkyl,
wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP,
and —C(O)CH$_2$NH—CPP, or G is of the formula:

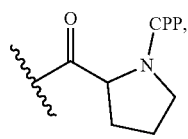

wherein the CPP is attached to the linker moiety by an amide bond at the CPP carboxy terminus. In some embodiments, at least one instance of $R^1$ is —N(CH$_3$)$_2$. In certain embodiments, each instance of $R^1$ is —N(CH$_3$)$_2$.

In various aspects, an antisense oligomer of the disclosure includes a compound of formula (VI):

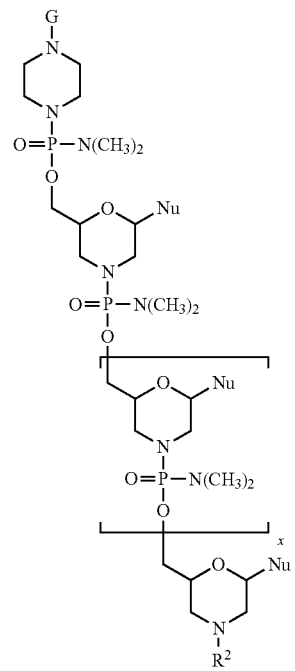

(VI)

or a pharmaceutically acceptable salt thereof, wherein:
X is an integer from 9 to 28;
each Nu is a nucleobase which taken together forms a targeting sequence;
$R^2$ is selected from H or acyl; and
G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP,
and —C(O)CH$_2$NH—CPP, or G is of the formula:

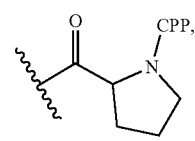

wherein the CPP is attached to the linker moiety by an amide bond at the CPP carboxy terminus.

The antisense oligomers can be prepared by stepwise solid-phase synthesis, employing methods known in the art and described in the references cited herein.

B. Cell-Penetrating Peptides

Figure 1F:
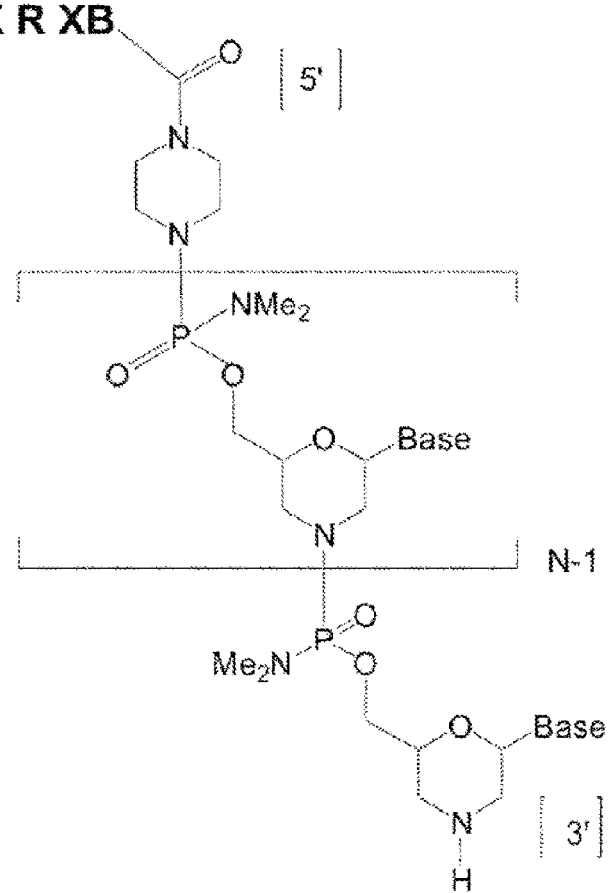
Figure 1G:
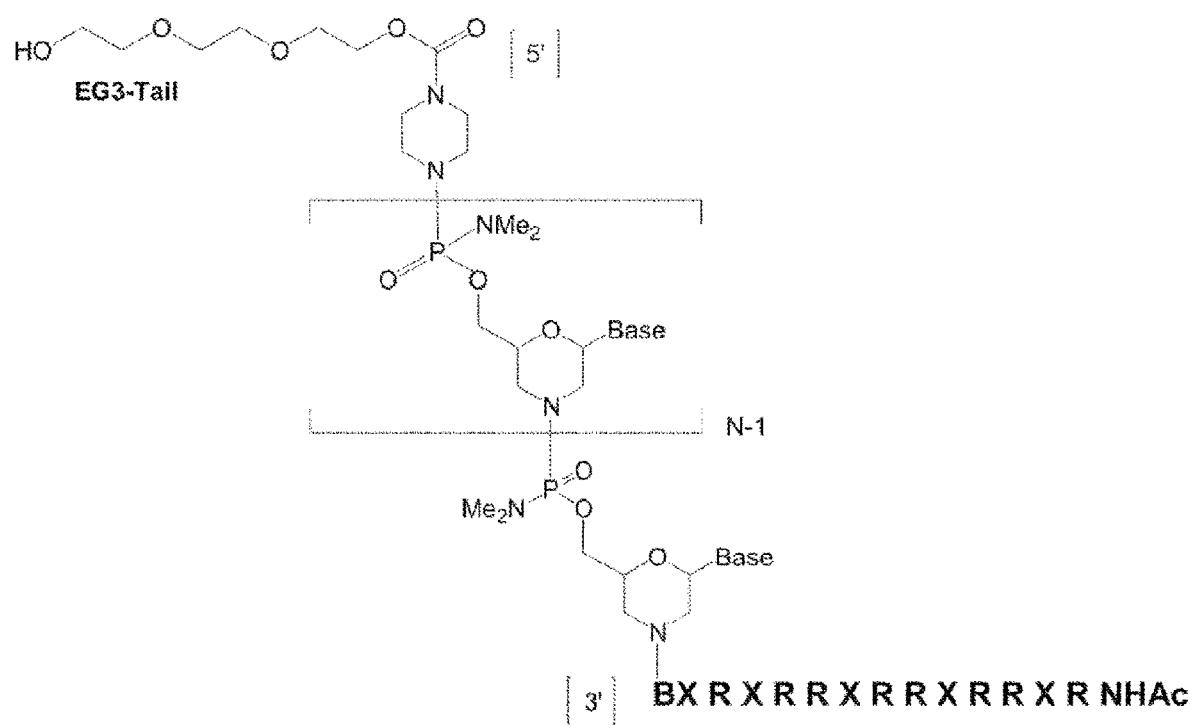
Figure 1H:
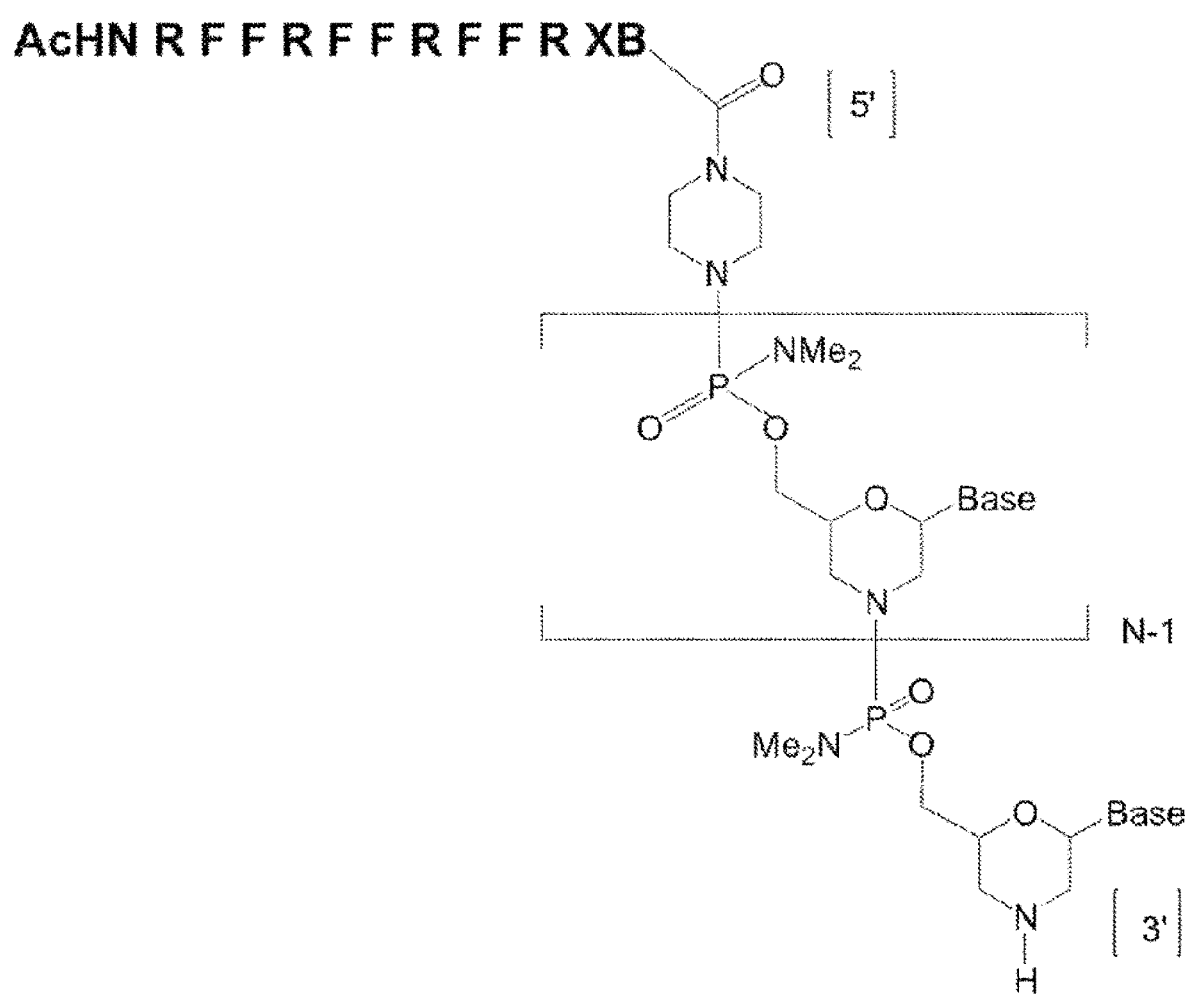

In certain embodiments, the antisense oligomer is conjugated to a cell-penetrating peptide (CPP). In some embodiments, the CPP is an arginine-rich peptide. By "arginine-rich carrier peptide" is meant that the CPP has at least 2, and preferably 2, 3, 4, 5, 6, 7, or 8 arginine residues, each optionally separated by one or more uncharged, hydrophobic residues, and optionally containing about 6-14 amino acid residues. FIGS. 1F-1H show exemplary chemical structures of CPP-PMO conjugates used in the Examples, including 5' and 3' PMO conjugates.

Exemplary CPPs are provided in Table C1 (SEQ ID NOS:21-35).

TABLE C1

Exemplary Cell-Penetrating Peptides

| Name | Sequence | SEQ ID NO: |
|---|---|---|
| (RXR)$_4$ | RXRRXRRXRRXR | 21 |
| (RFF)$_3$R | RFFRFFRFFR | 22 |
| (RXR)$_4$XB | RXRRXRRXRRXRXB | 23 |
| (RFF)$_3$RXB | RFFRFFRFFRXB | 24 |
| (RFR)$_4$ | RFRRFRRFRRFR | 25 |
| (RYR)$_4$ | RYRRYRRYRRYR | 26 |
| (RGR)$_4$ | RGRRGRRGRRGR | 27 |
| (RFR)$_4$XB | RFRRFRRFRRFRXB | 28 |
| (RYR)$_4$XB | RYRRYRRYRRYRXB | 29 |
| (RGR)$_4$XB | RGRRGRRGRRGRXB | 30 |
| (RFF)$_3$RXB | RFFRFFRFFRXB | 31 |
| (RFF)$_3$RG | RFFRFFRFFRG | 32 |
| (R)$_6$G | RRRRRRG | 33 |
| (RXR)$_4$G | RXRRXRRXRRXRG | 34 |
| (R)$_6$ | RRRRRR | 35 |

X is 6-aminohexanoic acid;
B is β-alanine;
F is phenylalanine;
Y is tyrosine;
G is glycine;
R is arginine In some embodiments, the CPP is linked at its C-terminus to the 3'-end or the 5'-end of the oligomer via a 1, 2, 3, 4, or 5 amino acid linker.

CPPs, their synthesis, and methods of conjugating a CPP to an oligomer are detailed, for example, in International Patent Application Publication Nos. WO 2004/097017, WO 2009/005793, and WO 2012/150960, which are all incorporated by reference in their entirety.

In some embodiments, the CPP is linked at its C-terminus to the 3'-end or the 5'-end of the oligomer via a 1, 2, 3, 4, or 5 amino acid linker. In particular embodiments, including antisense oligomer compounds of formula (I)—(VI), the linkers can include: —C(O)(CH$_2$)$_5$NH—CPP (X linker), —C(O)(CH$_2$)$_2$NH—CPP (B linker), —C(O)(CH$_2$)$_2$NHC(O) (CH$_2$)$_5$NH—CPP (XB peptide linker), and —C(O) CH$_2$NH—CPP (G linker), or formula:

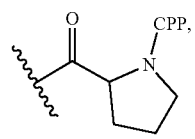

wherein the CPP is attached to the linker moiety by an amide bond at the CPP carboxy terminus. In some embodiments of the disclosure, including antisense oligomer compounds of formula (I)—(VI), G is selected from SEQ ID NOS: 23-24 and 28-34. In various embodiments, including antisense oligomer compounds of formula (I)—(VI), the CPP is selected from SEQ ID NO: 21, 22, 25-27, and 35.

In some embodiments, including antisense oligomer compounds of formula (I)—(VI), the CPP is selected from:

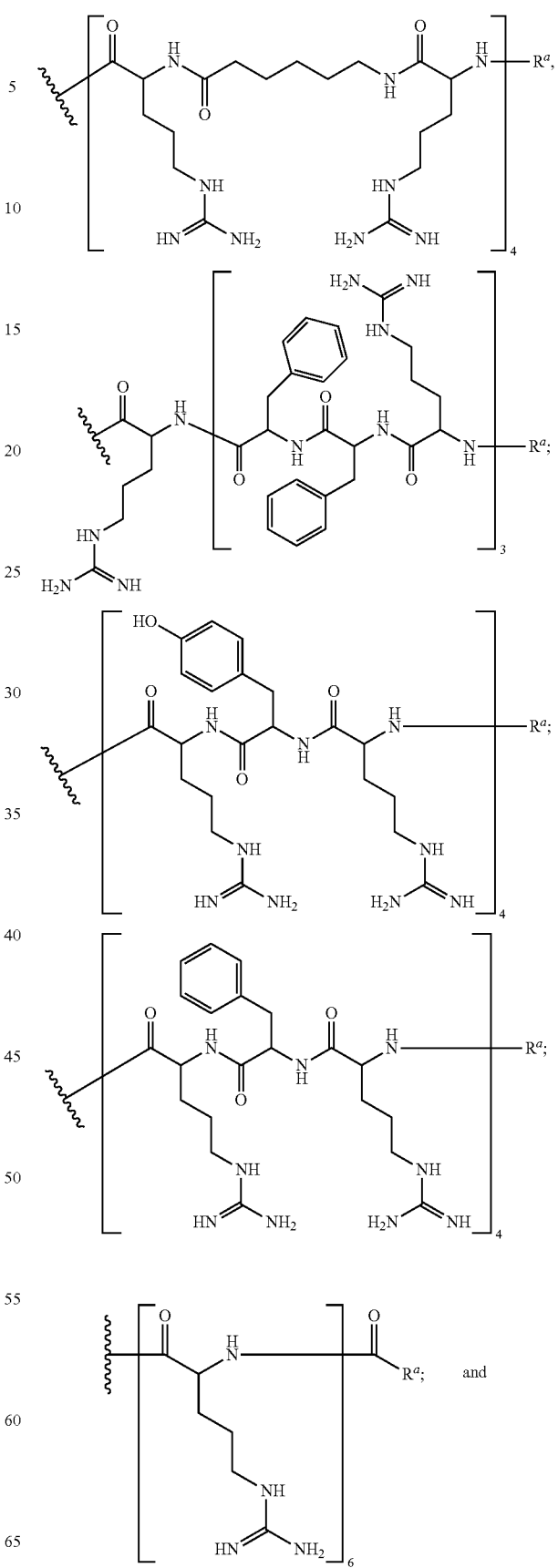

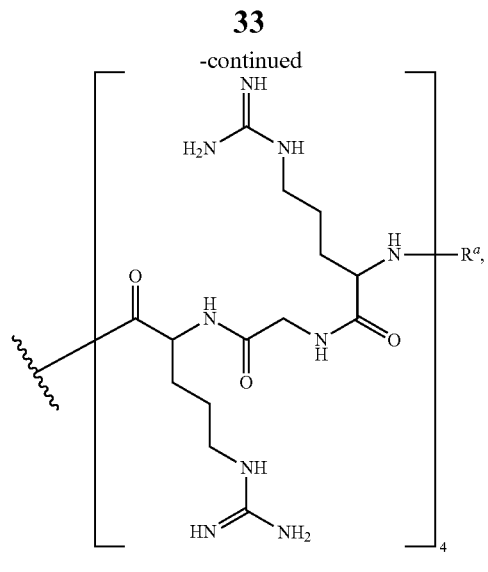
wherein $R^a$ is selected from H, acetyl, benzoyl, and stearoyl.
In some embodiments, including antisense oligomer compounds of formula (I)—(VI), G is selected from:
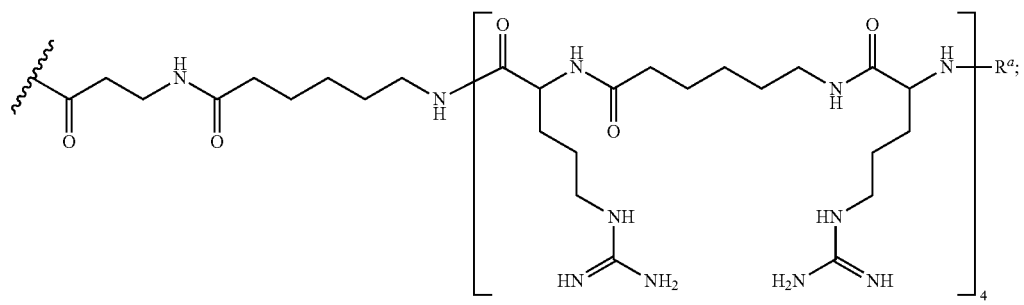
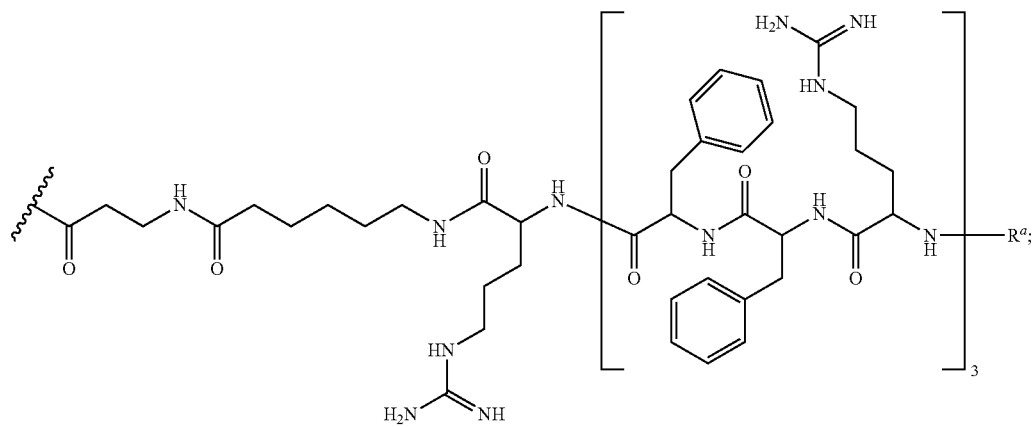

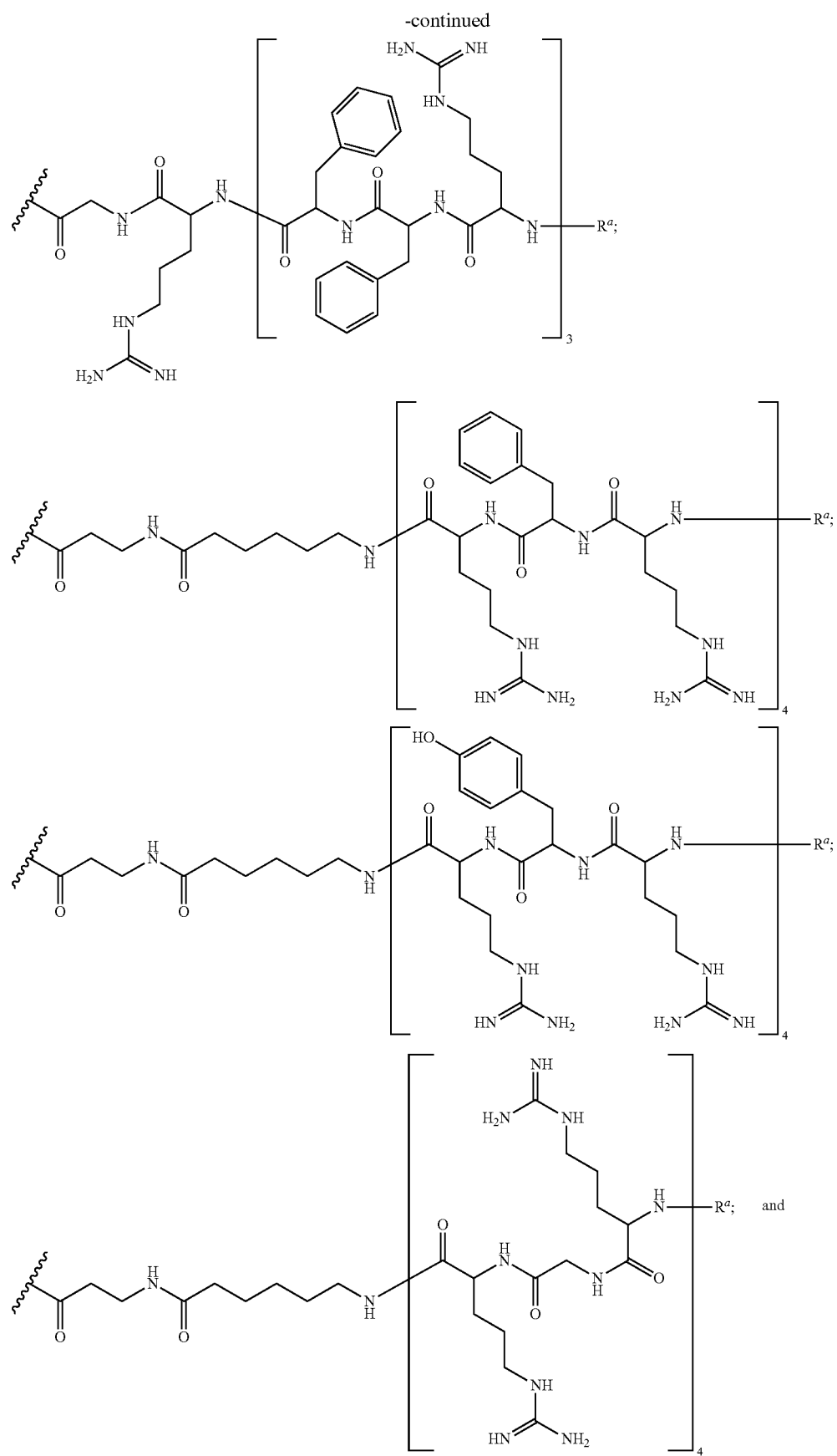

-continued
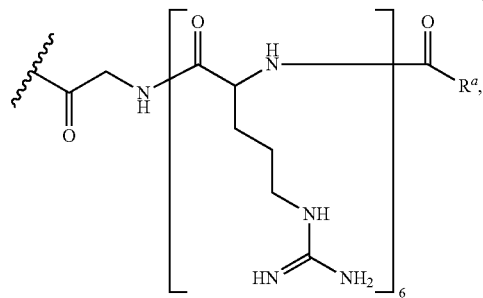
wherein $R^a$ is selected from H, acetyl, benzoyl, and stearoyl.
In various aspects, an antisense oligomer of the disclosure, or a pharmaceutically acceptable salt thereof, includes an antisense oligomer of the formula (VII) selected from:

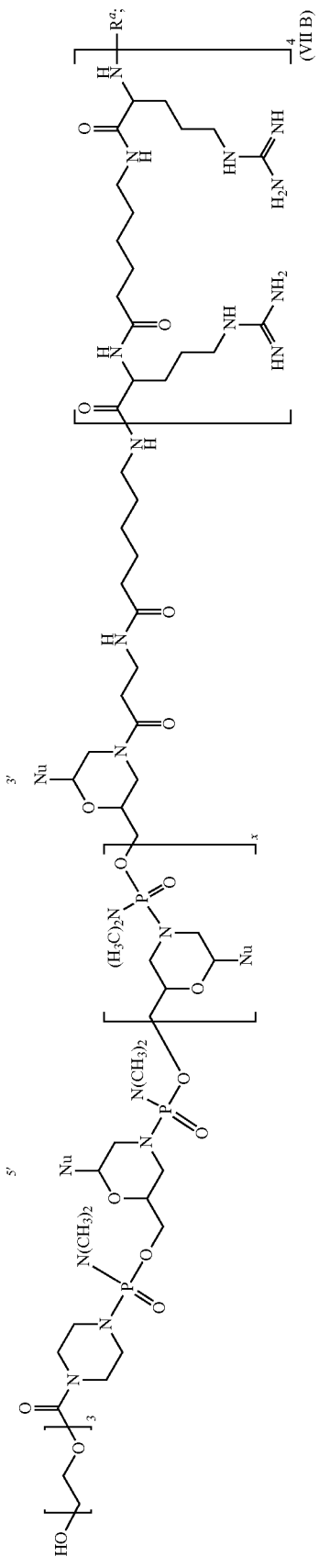
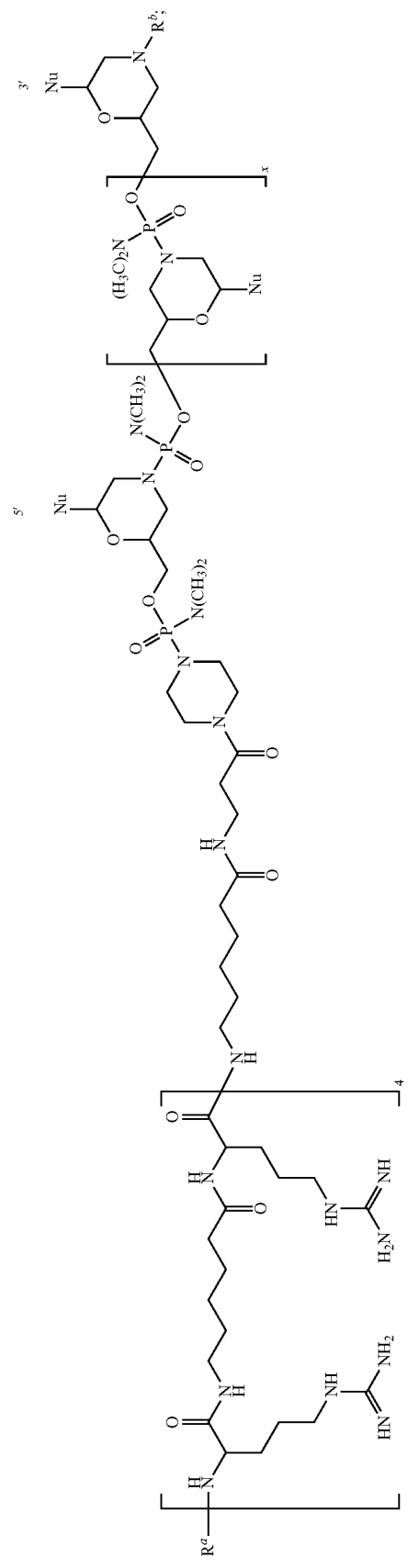

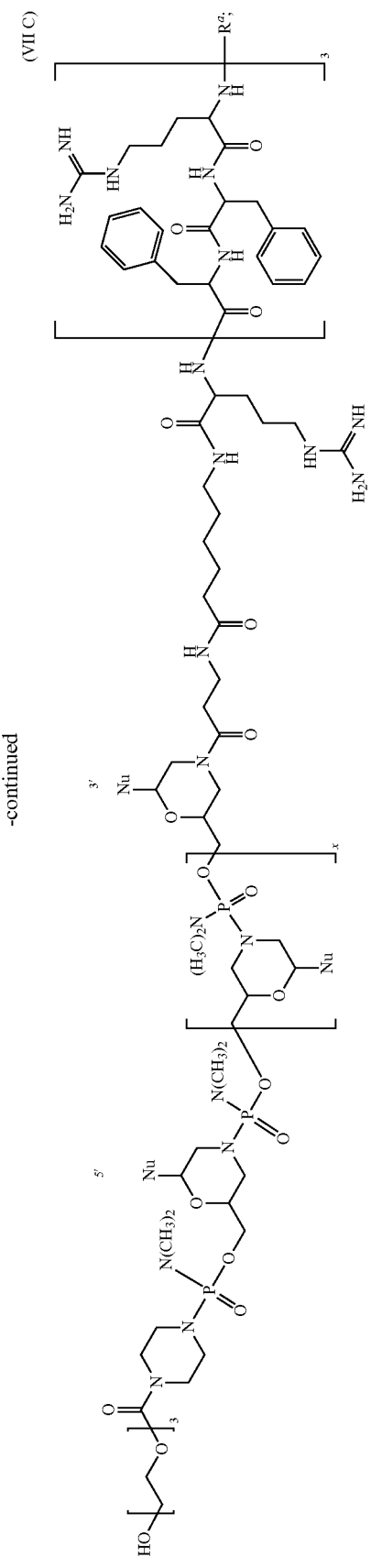
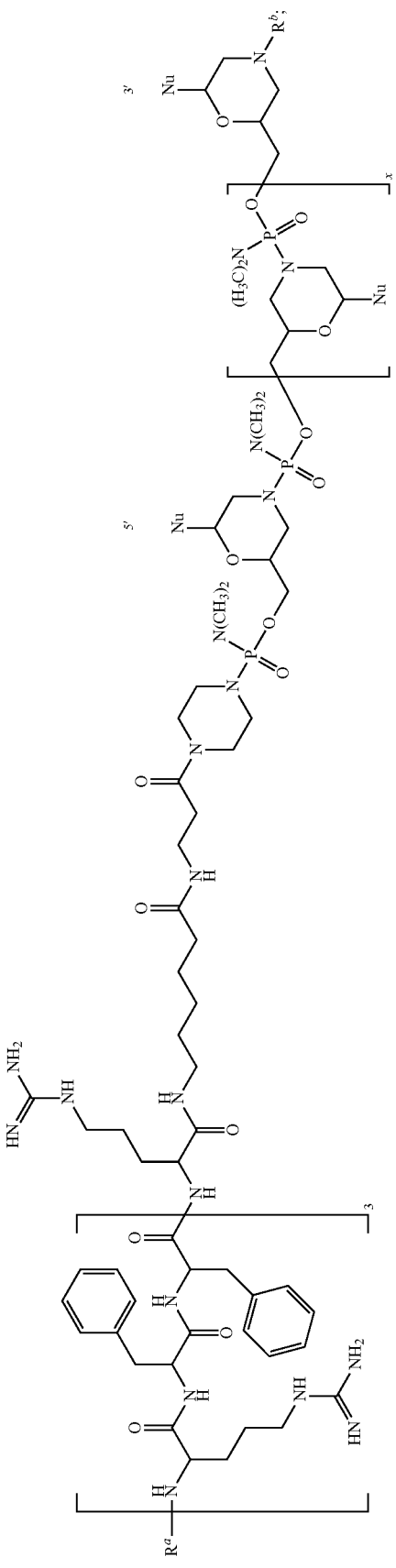

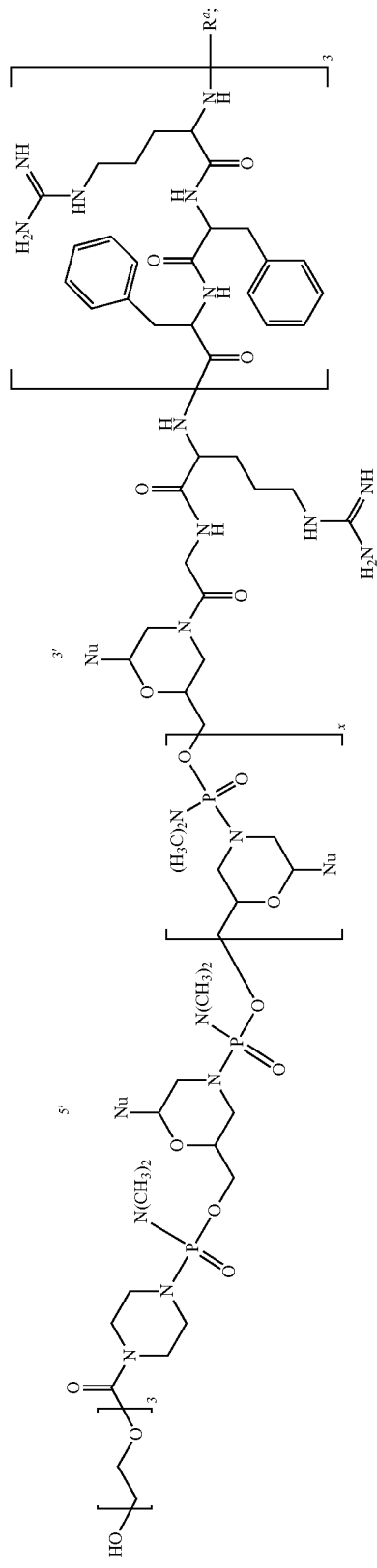
(VIIE)
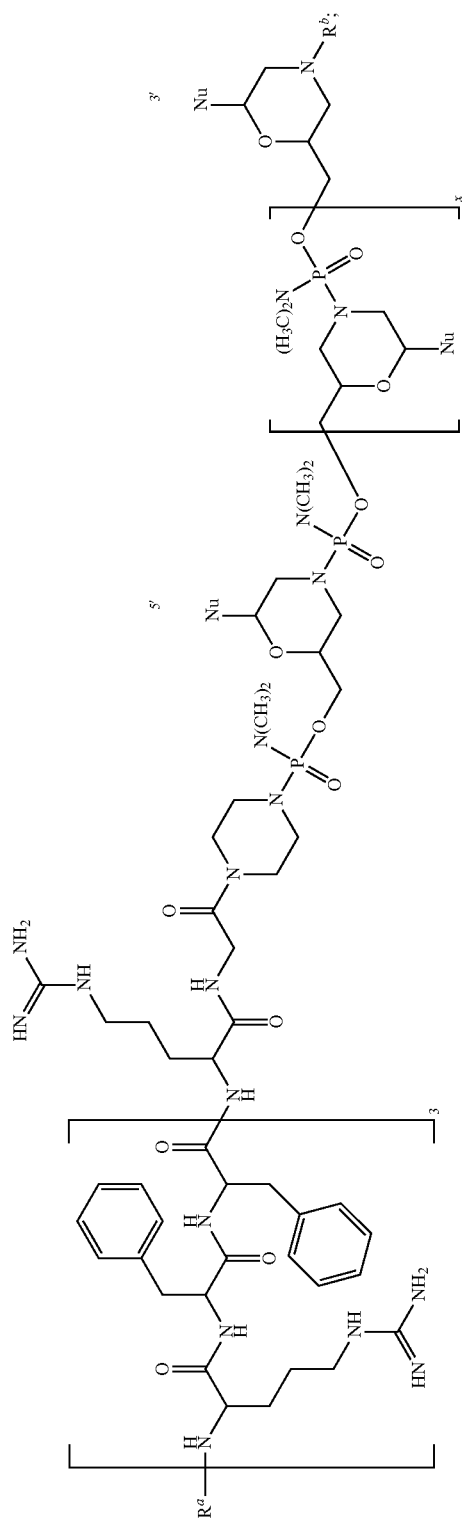
(VIIF)

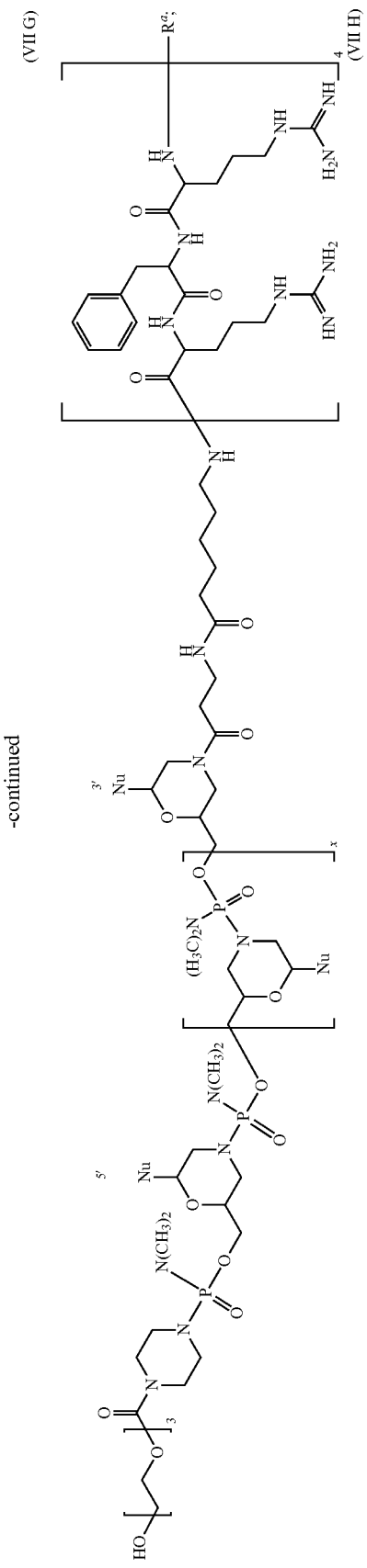
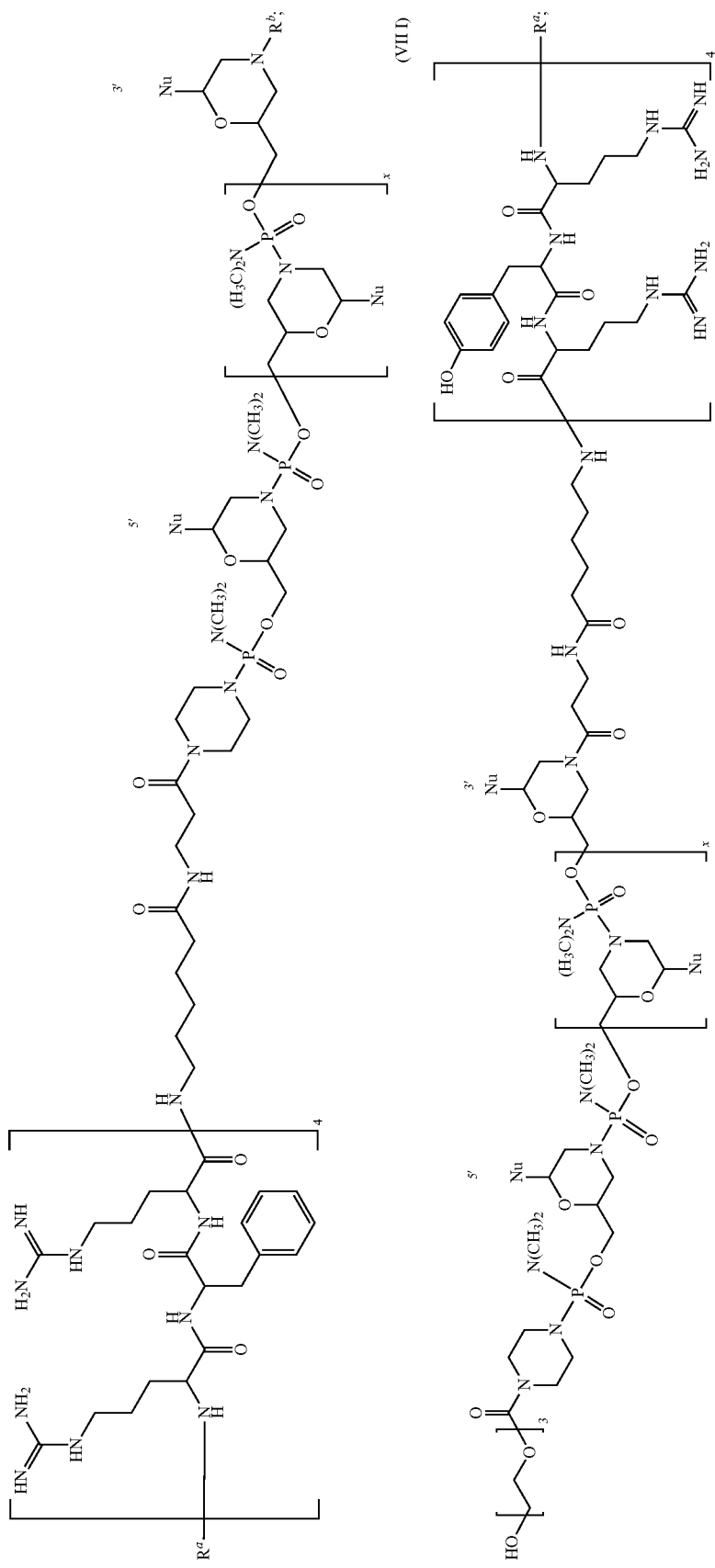

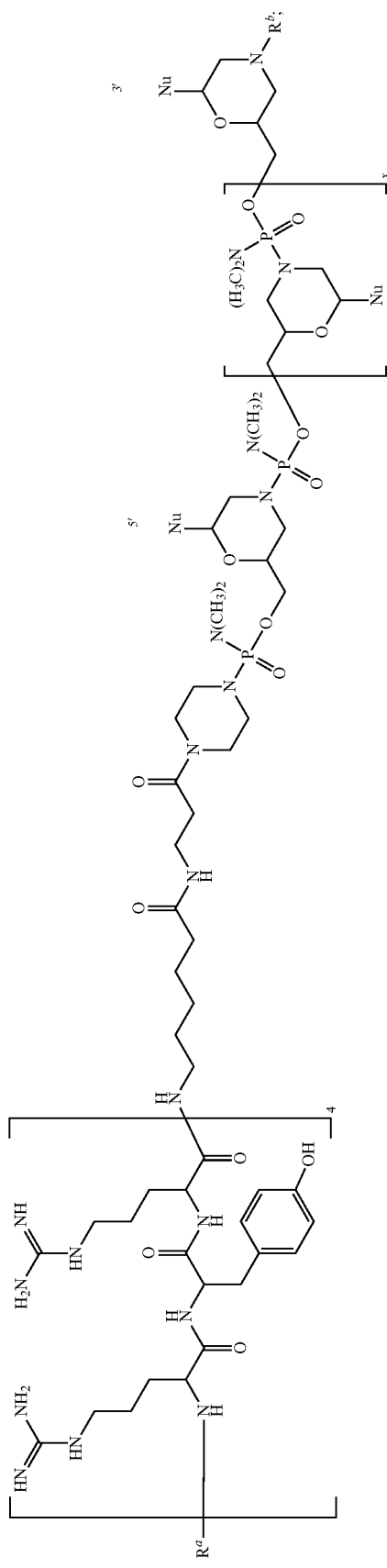
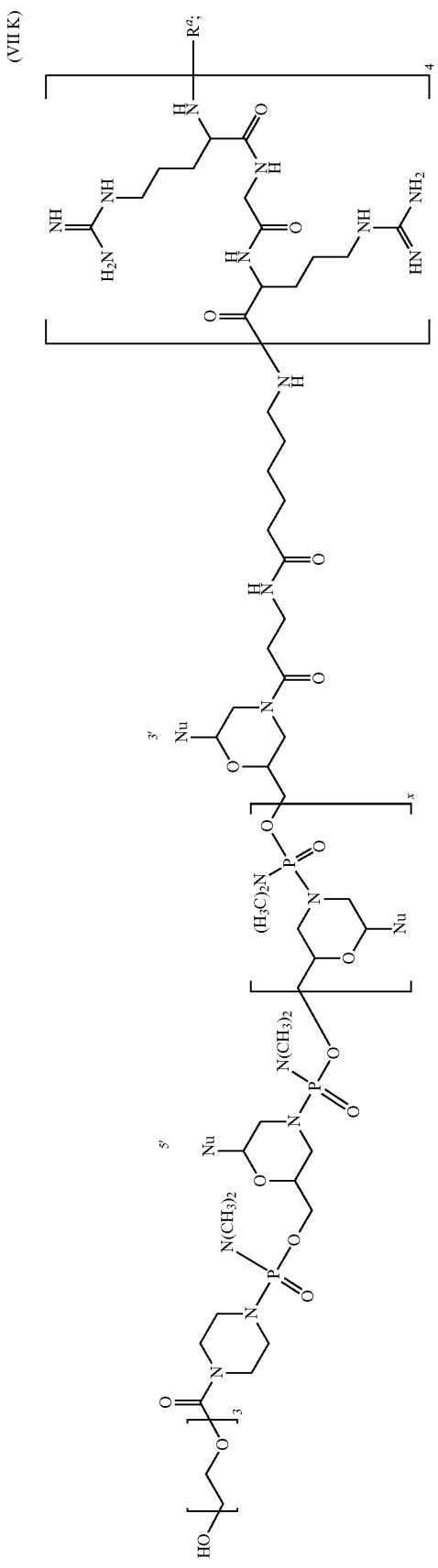

-continued
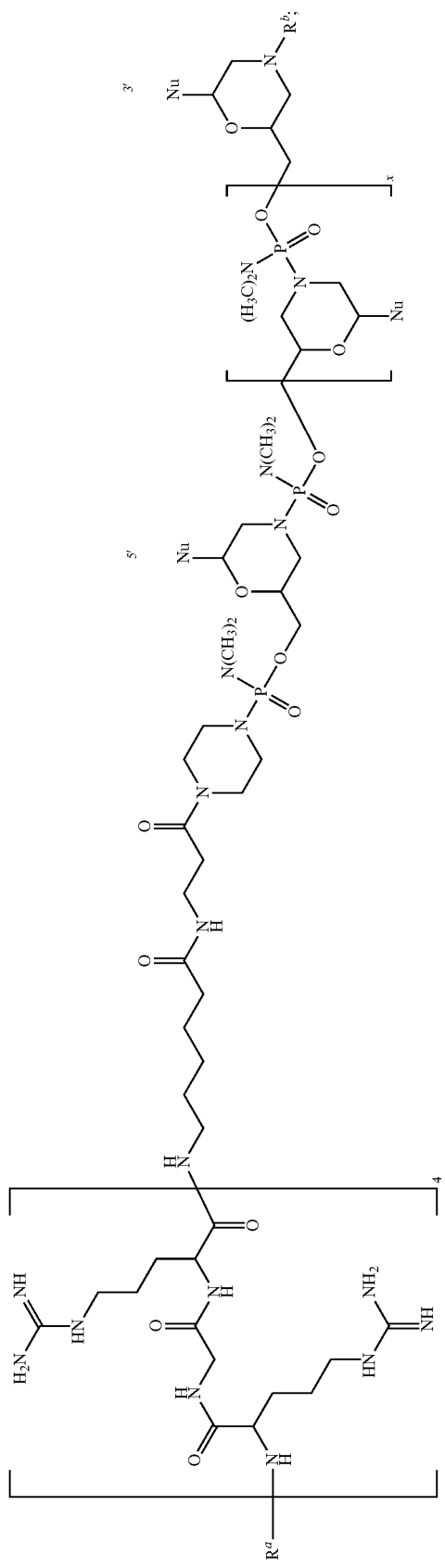
(VII L)
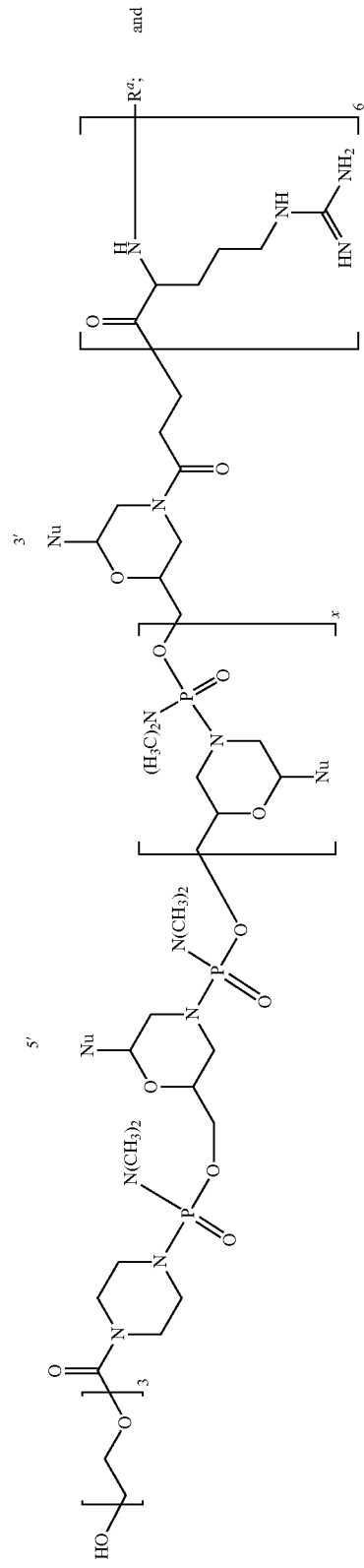
(VII M)
and (VII N)
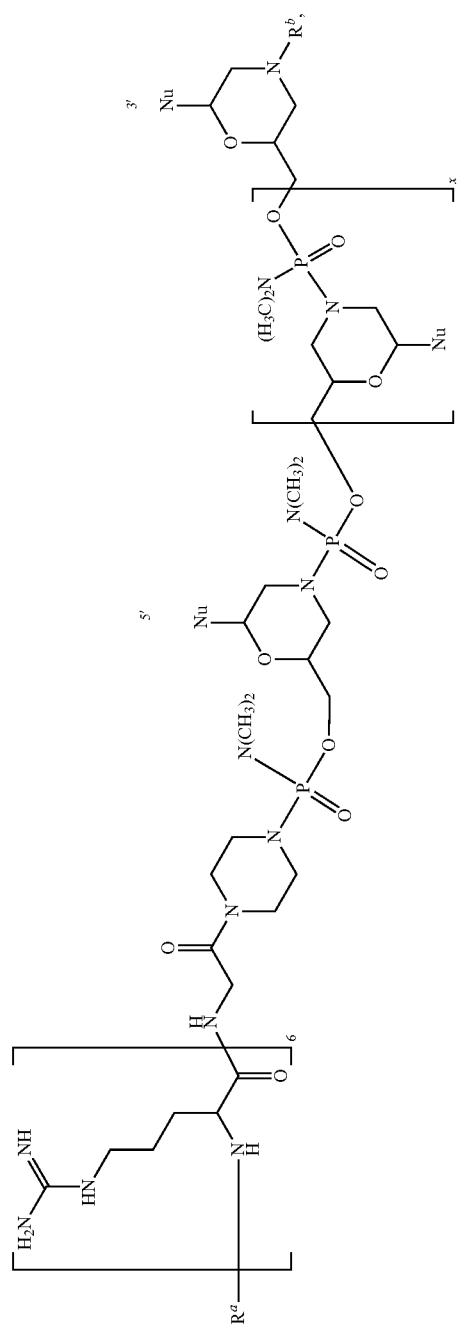

wherein X is an integer from 9 to 38, $R^a$ is selected from H, acetyl, benzoyl, and stearoyl, $R^b$ is selected from H, acetyl, benzoyl, stearoyl, trityl, and 4-methoxytrityl, and each Nu is a purine or pyrimidine base-pairing moiety which taken together form a targeting sequence described above.

C. Antisense Oligomer Targeting Sequences

In various embodiments of the antisense oligomers of the disclosure, including the antisense oligomer compounds of formulas (I)—(VII), the targeting sequence can specifically hybridizes to a bacterial mRNA target sequence that encodes a protein associated with a biochemical pathway and/or cellular process, or a rRNA target sequence. In some embodiments, the target sequence comprises a translational start codon of the bacterial mRNA and/or a sequence within about 30 bases upstream or downstream of the translational start codon of the bacterial mRNA.

In various embodiments, the protein associated with a biochemical pathway and/or cellular process may be a fatty acid biosynthesis protein. In some embodiments, the fatty acid biosynthesis protein can be an acyl carrier protein. In certain embodiments, the acyl carrier protein may be AcpP. In some embodiments, the fatty acid biosynthesis protein may be an acyl carrier protein synthase. In certain embodiments, the acyl carrier protein synthase may be FabB. In some embodiments, the fatty acid biosynthesis protein may be a carboxyltransferase alpha subunit of an acetyl Coenzyme A carboxylase. In certain embodiments, the carboxyltransferase alpha subunit of an acetyl Coenzyme A carboxylase may be AccA. In some embodiments, the target sequence may be SEQ ID NOs:1-3, wherein thymine bases (T) are optionally uracil bases (U). In certain embodiments, the targeting sequence comprises or consists of at least one of the targeting sequences in Table 1A (e.g., SEQ ID NOS:1-3), comprises or consists of a fragment of at least 10 contiguous nucleotides of a targeting sequence in Table 1A (e.g., SEQ ID NOS:1-3), or comprises or consists of a variant having at least 80% sequence identity to a targeting sequence in Table 1A (e.g., SEQ ID NOS:1-3), wherein thymine bases (T) are optionally uracil bases (U).

In some embodiments, the protein associated with a biochemical pathway and/or cellular process may be a peptidoglycan biosynthesis protein. In certain embodiments, the peptidoglycan biosynthesis protein can be a UDP-N-acetylglucosamine 1-carboxyvinyltransferase. In some embodiments, the UDP-N-acetylglucosamine 1-carboxyvinyltransferase may be MurA.

In some embodiments, the protein associated with a biochemical pathway and/or cellular process is a ribosomal protein. In certain embodiments, the ribosomal protein is a 50S ribosomal protein L28. In some embodiments, the 50S ribosomal protein L28 is RpmB. In certain embodiments, the ribosomal protein is a 30S ribosomal protein. In some embodiments, the 30S ribosomal protein is RpsJ.

In some embodiments, the protein associated with a biochemical pathway and/or cellular process is a ribosomal RNA (rRNA). Examples of rRNA include 5S, 16S, and 23S rRNA. In some embodiments, the rRNA is a 16S rRNA. In certain embodiments, the rRNA is a 23S rRNA.

In some embodiments, the protein associated with a biochemical pathway and/or cellular process is a DNA or chromosomal replication protein. In certain embodiments, the DNA or chromosomal replication protein is a topoisomerase. In some embodiments, the topoisomerase is GyrA. In certain embodiments, the DNA or chromosomal replication protein is a helicase. In some embodiments, the helicase is DnaB. In some embodiments, the DNA or chromosomal replication protein is a DNA polymerase. In some embodiments, the DNA polymerase is PolB.

In certain embodiments, the protein associated with a biochemical pathway and/or cellular process is a lipopolysaccharide biosynthesis protein. In some embodiments, the lipopolysaccharide biosynthesis protein is a N-acetylglucosamine deacetylase. In some embodiments, the N-acetylglucosamine deacetylase is LpxC.

In various embodiments, the protein associated with a biochemical pathway and/or cellular process is a cellular energy homeostasis protein. In some embodiments, the cellular energy homeostasis protein is an adenylate kinase. In certain embodiments, the adenylate kinase is Adk.

In some embodiments, the protein associated with a biochemical pathway and/or cellular process is a protein biosynthesis protein. In certain embodiments, the protein biosynthesis protein is a translation initiation factor. In various embodiments, the translation initiation factor is InfA.

In some embodiments, the protein associated with a biochemical pathway and/or cellular process is a cell division protein. In certain embodiments, the cell division protein is a protein that assembles into a ring at the future site of the septum of bacterial cell division. For example, in some embodiments, the protein that assembles into a ring at the future site of the septum of bacterial cell division is FtsZ.

In certain embodiments, the protein associated with a biochemical pathway and/or cellular process is an RNA synthesis protein. In some embodiments, the RNA synthesis protein is a sigma D factor of RNA polymerase. For example, in certain embodiments, the sigma D factor of RNA polymerase is RpoD.

In some embodiments, the protein associated with a biochemical pathway and/or cellular process is an aromatic compound biosynthesis protein. In certain embodiments, the aromatic compound biosynthesis protein is a chorismate synthase (5-enolpyruvylshikimate-3-phosphate phospholyase). For example, in some embodiments, the chorismate synthase (5-enolpyruvylshikimate-3-phosphate phospholyase) is AroC.

In some embodiments, the protein associated with antibiotic resistance is selected from one or more of BlaT, CmI, and AdeA.

In some embodiments where the protein associated with a biochemical pathway and/or cellular process may be a murein biosynthesis protein, cell division protein, global gene regulatory protein, fatty acid biosynthesis protein, ribosomal protein, ribosomal RNA (rRNA), DNA/chromosomal replication protein, transcription protein, translation initiation protein, lipopolysaccharide biosynthesis protein, nucleic acid biosynthesis protein, intermediary metabolism protein, RNA biosynthesis protein, protein biosynthesis protein, peptidoglycan biosynthesis protein, cellular energy homeostasis protein, aromatic compound biosynthesis protein, and antibiotic resistance protein, or other protein described herein, the targeting sequence comprises or consists of at least one of the targeting sequences set forth in Table 1B (e.g., SEQ ID NOS:4-20), comprises or consists of a fragment of at least 10 contiguous nucleotides of a targeting sequence in Table 1B (e.g., SEQ ID NOS:4-20), or comprises or consists of a variant having at least 80% sequence identity to a targeting sequence in Table 1B (e.g., SEQ ID NOS:4-20), wherein thymine bases (T) are optionally uracil bases (U).

In certain embodiments, including the antisense oligomer compounds of formulas (I)—(VII), the targeting sequence is selected from:

a) (CTC ATA CCT TG); SEQ ID NO: 1 b) (TGC TCA TAC TC); SEQ ID NO: 2 c) (CGT TTC ATT AA); SEQ ID NO: 3 wherein X is 9, wherein thymine bases (T) may be uracil bases (U).

In some embodiments, including the antisense oligomer compounds of formulas (I)—(VII), the targeting sequence is selected from:

a) (TTT ATC CAT TG); SEQ ID NO: 4 b) (GCA TTT GAC CT); SEQ ID NO: 5 c) (GTC TAT TCT CC); SEQ ID NO: 6 d) (GAC ATG TCT AT); SEQ ID NO: 7 e) (TGG TTC TGC AT); SEQ ID NO: 8 f) (AGT TTC TCT CC); SEQ ID NO: 9 g) (GTT CAA ACA TA); SEQ ID NO: 10 h) (CGC TCA TCT AA); SEQ ID NO: 11 i) (TTC CTG CCA TA); SEQ ID NO: 12 j) (TTT GAT CAT CG); SEQ ID NO: 13 k) (AGT GCT CTA CC); SEQ ID NO: 14 l) (GCC TGT TAT CC); SEQ ID NO: 15 m) (CCA TGC AGC AC); SEQ ID NO: 16 n) (TTG CGC TCG TT); SEQ ID NO: 17 o) (GGC TGC TGG CA); SEQ ID NO: 18 p) (TCA TCT TTG CT); SEQ ID NO: 19 q) (AGT AAC TCC AC); SEQ ID NO: 20 wherein X is 9, and wherein thymine bases (T) may be uracil bases (U).

D. Exemplary Antisense Oligomers

Exemplary antisense oligomers (AONs) of the disclosure include those described in Tables 2A-B below.

TABLE 2A

Exemplary Fatty Acid Biosynthesis-Associated Targeting Sequences AONs

| PPMO Name | Target Gene | Targeting Sequence (TS)* | TS SEQ ID NO: | 5' Attachment*** | 3' Attachment** | CPP SEQ ID NO. |
|---|---|---|---|---|---|---|
| PPMO#1 | acpP | CTC ATA CCT TG | 1 | (R)$_6$G | | 31 |
| PPMO#2 | acpP | TGC TCA TAC TC | 2 | (RXR)$_4$XB | | 21 |
| PPMO#3 | fabB | CGT TTC ATT AA | 3 | (RXR)$_4$XB | | 21 |

TABLE 2B

Exemplary AONS targeting other biochemical pathways, cellular processes, and/or antibiotic resistance

| PPMO Name | Target Gene | Targeting Sequence (TS)* | TS SEQ ID NO: | 5' Attachment*** | 3' Attachment** | CPP SEQ ID NO. |
|---|---|---|---|---|---|---|
| PPMO#4 | murA | TTT ATC CAT TG | 4 | (RXR)$_4$XB | | 23 |
| PPMO#5 | rpsJ | GCA TTT GAC CT | 5 | (RXR)$_4$XB | | 23 |
| PPMO#6 | rpmB | GTC TAT TCT CC | 6 | (RXR)$_4$XB | | 23 |
| PPMO#7 | rpmB | GAC ATG TCT AT | 7 | (RXR)$_4$XB | | 23 |

TABLE 2B-continued

Exemplary AONS targeting other biochemical pathways, cellular processes, and/or antibiotic resistance

| PPMO Name | Target Gene | Targeting Sequence (TS)* | TS SEQ ID NO: | 5' Attachment*** | 3' Attachment** | CPP SEQ ID NO. |
|---|---|---|---|---|---|---|
| PPMO#8 | rpsJ | TGG TTC TGC AT | 8 | (RXR)$_4$XB | | 23 |
| PPMO#9 | ftsZ | AGT TTC TCT CC | 9 | (RXR)$_4$XB | | 23 |
| PPMO#10 | ftsZ | GTT CAA ACA TA | 10 | (RXR)$_4$XB | | 23 |
| PPMO#11 | gyrA | CGC TCA TCT AA | 11 | (RFR)$_4$XB | | 28 |
| PPMO#12 | gyrA | CGC TCA TCT AA | 11 | (RGR)$_4$XB | | 30 |
| PPMO#13 | dnaB | TTC CTG CCA TA | 12 | (RXR)$_4$XB | | 23 |
| PPMO#14 | lpxC | TTT GAT CAT CG | 13 | (RXR)$_4$XB | | 23 |
| PPMO#15 | 23S rRNA | AGT GCT CTA CC | 14 | (RXR)$_4$XB | | 23 |
| PPMO#16 | 23S rRNA | GCC TGT TAT CC | 15 | (RXR)$_4$XB | | 23 |
| PPMO#17 | 16S rRNA | CCA TGC AGC AC | 16 | (RXR)$_4$XB | | 23 |
| PPMO#18 | 16S rRNA | TTG CGC TCG TT | 17 | (RXR)$_4$XB | | 23 |
| PPMO#19 | 16S rRNA | GGC TGC TGG CA | 18 | (RFF)$_3$RXB | | 31 |
| PPMO#20 | rpoD | TCA TCT TTG CT | 19 | | (RXR)$_4$XB | 23 |
| PPMO#21 | polB | AGT AAC TCC AC | 20 | (RXR)$_4$XB | | 23 |

IV. Methods of Use and Formulations

Embodiments of the present disclosure include methods of using the antisense oligomers described herein to reduce the expression and activity of one or more bacterial proteins associated with biochemical pathways, cellular processes, and/or antibiotic resistance. Certain embodiments include methods of using the antisense oligomers to reduce replication, proliferation, or growth of a bacteria, for example, to treat a bacterial infection in a subject, either alone or in combination with one or more additional antimicrobial agents. In some instances, the antisense oligomers increase the susceptibility of the bacterium to one or more antimicrobial agents.

Also included are pharmaceutical compositions comprising the antisense oligomers, typically in combination with a pharmaceutically-acceptable carrier. Certain pharmaceutical compositions can further comprise one or more antimicrobial agents. The methods provided herein can be practiced in vitro or in vivo.

For example, certain embodiments include methods of treating a bacterial infection in a subject, comprising administering to a subject in need thereof (e.g., subject having or at risk for having a bacterial infection) an antisense oligomer or pharmaceutical composition described herein. Also included are methods of reducing replication of a bacteria, comprising contacting the bacterium with an antisense oligomer described herein.

In some embodiments, the bacterium is selected from the genus *Klebsiella, Pseudomonas, Acinetobacter*, and *Escherichia*.

*Klebsiella* is a genus of a Gram-negative, nonmotile, encapsulated, lactose-fermenting, facultative anaerobic, rod-shaped bacterium that includes the species *Klebsiella pneumoniae*, which is responsible for the vast majority of *Klebsiella*-related pathogenesis.

*Pseudomonas* is a genus of Gram-negative, aerobic rod-shaped bacterium that commonly found in skin, soil, and water. The genus includes the species *Pseudomonas aeruginosa*, an opportunistic pathogen that is responsible for the vast majority of *Pseudomonas*-related infections.

It causes urinary tract infections, respiratory system infections, dermatitis, soft tissue infections, bacteremia, bone and joint infections, gastrointestinal infections and a variety of systemic infections, particularly in patients with severe burns and in cancer and AIDS patients who are immunosuppressed. *Pseudomonas aeruginosa* infections are a serious problem in patients hospitalized with cancer, cystic fibrosis, and burns.

*Acinetobacter* is a genus of Gram-negative bacteria belonging to the class of Gammaproteobacteria. Examples of clinically-relevant *Acinetobacter* complexes include the *Acinetobacter calcoaceticus-baumannii* complex (glucose-oxidizing nonhemolytic), *Acinetobacter lwoffii* (glucose-negative nonhemolytic), and *Acinetobacter haemolyticus* (hemolytic). Specific examples include *Acinetobacter baumannii*.

*Escherichia* is a genus of Gram-negative, non-spore forming, facultatively anaerobic, rod-shaped bacteria from the family Enterobacteriaceae, and includes the species *Escherichia coli*, which is responsible for the vast majority of *Escherichia*-related pathogenesis.

Thus, in some embodiments, the bacterium is any of the foregoing members of the genera *Klebsiella, Pseudomonas, Acinetobacter* or *Escherichia*. In specific embodiments, the bacterium is *Klebsiella pneumoniae, Pseudomonas aeruginosa, Acinetobacter baumannii*, or *Escherichia coli*. In some embodiments, the bacterium is selected from one or more of the strains in Table E1.

In certain embodiments, the bacterium is a multi-drug resistance (MDR) strain of bacteria. Multiple drug resistance (MDR), multi-drug resistance or multiresistance is a condition enabling disease-causing microorganisms (bacteria, viruses, fungi or parasites) to resist distinct antimicrobials such as antibiotics, antifungal drugs, antiviral medications, antiparasitic drugs, and others. In particular embodiments, the bacterium is extensively-drug resistant (XDR) or pan-drug resistant (PDR). In some embodiments, the bacterium is an extended-spectrum S-lactamase (ESBLs) producing Gram-negative bacteria, or a multi-drug-resistant gram negative rod (MDR GNR) MDRGN bacteria. In specific embodiments, the bacterium is MDR *Klebsiella*, for example, MDR *Klebsiella pneumoniae*, or MDR *Pseudomonas*, for example, MDR *Pseudomonas aeruginosa*. In some embodiments, the bacterium is MDR *Escherichia*, for example, MDR *Escherichia coli*, or MDR *Acinetobacter*, for example, MDR *Acinetobacter baumannii*.

Examples of genes associated with biochemical pathways and/or cellular processes include fatty acid biosynthesis genes (and their related proteins) such as acpP, accA, acpS, and/orfab genes, for example, fabB. In particular embodiments, the bacterium comprises or expresses the acpP gene, which encodes an acyl carrier protein. In particular embodiments, the bacterium comprises or expresses the accA gene, which encodes a carboxyltransferase alpha subunit of an acetyl Coenzyme A carboxylase. In some embodiments, the bacterium comprises or expresses the fabB gene, which encodes an carrier protein synthase.

In some embodiments, the bacterium that comprises or expresses one or more genes associated with fatty acid biosynthesis (e.g., acpP, fabB) is a *Klebsiella* species, for example, *Klebsiella pneumoniae*. In some embodiments, the bacterium that comprises or expresses one or more genes associated with fatty acid biosynthesis (e.g., acpP, fabB) is a *Pseudomonas* species, for example, *Pseudomonas aeruginosa*. In some embodiments, the bacterium that comprises or expresses one or more genes associated with fatty acid biosynthesis (e.g., acpP, fabB) is an *Acinetobacter* species, for example, *Acinetobacter baumannii*. In specific embodiments, the bacterium that comprises or expresses one or more genes associated with fatty acid biosynthesis (e.g., acpP,fabB) is an *Escherichia* species, for example, *Escherichia coli*. In some of these and related embodiments, the subject in need thereof is immunocompromised. In certain embodiments, the subject in need thereof is immunocompromised and has an underlying lung disease, such as pneumonia, cystic fibrosis (CF), or chronic granulomatous disease (CGD).

Examples of genes associated with biochemical pathways and/or cellular processes include peptidoglycan biosynthesis genes (and their related proteins). In particular embodiments, the bacterium comprises or expresses the murA gene, which encodes a UDP-N-acetylglucosamine 1-carboxyvinyltransferase. In some embodiments, the bacterium that comprises or expresses one or more peptidoglycan biosynthesis genes (e.g., murA) is a *Klebsiella* species, for example, *Klebsiella pneumoniae*. In some embodiments, the bacterium that comprises or expresses one or more peptidoglycan biosynthesis genes (e.g., murA) is a *Pseudomonas* species, for example, *Pseudomonas aeruginosa*. In some embodiments, the bacterium that comprises or expresses one or more peptidoglycan biosynthesis genes (e.g., murA) is an *Acinetobacter* species, for example, *Acinetobacter baumannii*. In specific embodiments, the bacterium that comprises or expresses one or more peptidoglycan biosynthesis genes (e.g., murA) is an *Escherichia* species, for example, *Escherichia coli*.

Examples of genes associated with biochemical pathways and/or cellular processes include ribosomal protein genes (and their related proteins). In particular embodiments, the bacterium comprises or expresses the rpmB gene, which encodes a 50S ribosomal protein L28. In particular embodiments, the bacterium comprises or expresses the rpsJ gene, which encodes a 30S ribosomal protein. In some embodiments, the bacterium that comprises or expresses one or more ribosomal protein genes (e.g., rpmB, rpsJ) is a *Klebsiella* species, for example, *Klebsiella pneumoniae*. In some embodiments, the bacterium that comprises or expresses one or more ribosomal protein genes (e.g., rpmB, rpsi) is a *Pseudomonas* species, for example, *Pseudomonas aeruginosa*. In some embodiments, the bacterium that comprises or expresses one or more ribosomal protein genes (e.g., rpmB, rpsi) is an *Acinetobacter* species, for example, *Acinetobacter baumannii*. In specific embodiments, the bacterium that comprises or expresses one or more ribosomal protein genes (e.g., rpmB, rpsJ) is an *Escherichia* species, for example, *Escherichia coli*.

Examples of genes associated with biochemical pathways and/or cellular processes include cellular homeostasis genes (and their related proteins). In particular embodiments, the bacterium comprises or expresses the adk gene, which encodes an adenylate kinase. Examples of genes associated with biochemical pathways and/or cellular processes include protein biosynthesis genes (and their related proteins). In particular embodiments, the bacterium comprises or expresses the infA gene, which encodes a translation initiation factor.

Examples of genes associated with biochemical pathways and/or cellular processes include cell division genes (and their related proteins). In particular embodiments, the bacterium comprises or expresses the ftsZ gene, which encodes a protein that assembles into a ring at the future site of the septum of bacterial cell division. In specific embodiments, the bacterium that comprises or expresses one or more genes associated with cell division (e.g., ftsZ) is a *Klebsiella* species, for example, *Klebsiella pneumoniae*. In some embodiments, the bacterium that comprises or expresses one or more genes associated with cell division (e.g., ftsZ) is a *Pseudomonas* species, for example, *Pseudomonas aeruginosa*. In some embodiments, the bacterium that comprises or expresses one or more genes associated with cell division (e.g., ftsZ) is an *Acinetobacter* species, for example, *Acinetobacter baumannii*. In specific embodiments, the bacterium that comprises or expresses one or more genes associated with cell division (e.g., ftsZ) is an *Escherichia* species, for example, *Escherichia coli*.

Examples of genes associated with DNA or chromosomal replication include topoisomerases and helicases (and their related proteins). In particular embodiments, the bacterium comprises or expresses the gyrA gene, which encodes a topoisomerase. In some embodiments, the bacterium comprises or expresses the dnaB gene, which encodes a helicase. In some embodiments, the bacterium comprises or expresses the polB gene, which encodes a DNA polymerase. In specific embodiments, the bacterium that comprises or expresses one or more genes associated with DNA or chromosomal replication (e.g., gyrA, dnaB, polB) is a *Klebsiella* species, for example, *Klebsiella pneumoniae*. In some embodiments, the bacterium that comprises or expresses one or more genes associated with DNA or chromosomal replication (e.g., gyrA, dnaB, polB) is a *Pseudomonas* species, for example, *Pseudomonas aeruginosa*. In some embodiments, the bacterium that comprises or expresses one or more genes associated with DNA or chromosomal replication (e.g., gyrA, dnaB, poIB) is an *Acinetobacter* species, for example, *Acinetobacter baumannii*. In specific embodiments, the bacterium that comprises or expresses one or more genes associated with DNA or chromosomal replication (e.g., gyrA, dnaB, poIB) is an *Escherichia* species, for example, *Escherichia coli*.

Examples of genes associated with lipopolysaccharide biosynthesis include deacetylases such as N-acetylglucosamine deacetylase. In particular embodiments, the bacterium comprises or expresses the IpxC gene, which encodes an N-acetylglucosamine deacetylase. In specific embodiments, the bacterium that comprises or expresses one or more genes associated with lipopolysaccharide biosynthesis (e.g., ipxC) is a *Klebsiella* species, for example, *Klebsiella pneumoniae*. In some embodiments, the bacterium that comprises or expresses one or more genes associated with lipopolysaccharide biosynthesis (e.g., ipxC) is a *Pseudomonas* species, for example, *Pseudomonas aeruginosa*. In some embodiments, the bacterium that comprises or expresses one or more genes associated with lipopolysaccharide biosynthesis (e.g., ipxC) is an *Acinetobacter* species, for example, *Acinetobacter baumannii*. In specific embodiments, the bacterium that comprises or expresses one or more genes associated with lipopolysaccharide biosynthesis (e.g., ipxC) is an *Escherichia* species, for example, *Escherichia coli*.

Examples of genes associated with biochemical pathways and/or cellular processes include RNA synthesis genes (and their related proteins). In particular embodiments, the bacterium comprises or expresses the rpoD gene, which encodes a sigma D factor of RNA polymerase. In specific embodiments, the bacterium that comprises or expresses one or more RNA synthesis genes (e.g., rpoD) is a *Klebsiella* species, for example, *Klebsiella pneumoniae*. In some embodiments, the bacterium that comprises or expresses one or more one or more RNA synthesis genes (e.g., rpoD) is a *Pseudomonas* species, for example, *Pseudomonas aeruginosa*. In some embodiments, the bacterium that comprises or expresses one or more one or more RNA synthesis genes (e.g., rpoD) is an *Acinetobacter* species, for example, *Acinetobacter baumannii*. In specific embodiments, the bacterium that comprises or expresses one or more RNA synthesis genes (e.g., rpoD) is an *Escherichia* species, for example, *Escherichia coli*.

Examples of genes associated with biochemical pathways and/or cellular processes include aromatic compound biosynthesis genes (and their related proteins). In particular embodiments, the bacterium comprises or expresses the aroC gene, which encodes a chorismate synthase (5-enolpyruvylshikimate-3-phosphate phospholyase).

In some embodiments, the bacteria or bacterium comprises (e.g., encodes) one or more antibiotic resistance genes. General examples of antibiotic resistance genes (and their related proteins) include beta-lactamases, which can enzymatically deactivate certain antimicrobial agents, and genes/proteins which increase the permeability or active efflux (pumping out) of an antimicrobial agent. Particular examples of antibiotic resistance genes include TEM beta-lactamase (blaT), chloramphenicol resistance gene cml and resistance-nodulation-cell division (RND)-type multidrug efflux pump subunit AdeA (adeA). In specific embodiments, the bacterium is *Klebsiella pneumonia, Pseudomonas aeruginosa, Acinetobacter* spp., or *Escherichia coli*, which comprises or expresses at least one antibiotic resistance gene selected from blaT, cm/and adeA.

In some embodiments, the antisense oligomer reduces expression of the gene(s) associated with biochemical pathways, cellular processes, and/or antibiotic resistance in the bacteria or bacterium. For instance, in some embodiments, the antisense oligomer reduces expression by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control (e.g., absence of the antisense oligomer, scrambled oligomer, prior to contacting with the oligomer), or by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to a control. In some embodiments, the antisense oligomer reduces expression of one or more of AcpP, FabB, AccA, MurA, RpmB, RpsJ, Adk, InfA, 16S rRNA, 30S rRNA, GyrA, DnaB, PolB, FtsZ, LpxC, RpoD, AroC, BlaT, CmI and/or AdeA and the bacterium is an *Klebsiella, Pseudomonas, Acinetobacter*, or *Escherichia* species which comprises or expresses one or more of AcpP, FabB, AccA, MurA, RpmB, RpsJ, Adk, InfA, 16S rRNA, 30S rRNA, GyrA, DnaB, PolB, FtsZ, LpxC, RpoD, AroC, BlaT, CmI and/or AdeA. Gene or protein expression can be measured in vitro (see, e.g., the Examples) or in vivo.

In some embodiments, the antisense oligomer reduces or inhibits the growth of the bacteria or bacterium. For instance, in some embodiments, the antisense oligomer reduces growth of the bacteria or bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control (e.g., absence of the antisense oligomer, scrambled oligomer, prior to contacting with the oligomer), or by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to a control. Bacterial growth can be measured in vitro (see, e.g., the Examples) or in vivo. In particular embodiments, the antisense oligomer that reduces growth of the bacterium is targeted against expression a protein associated with a biochemical pathway and/or cellular process selected from one or more of AcpP, FabB, AccA, MurA, RpmB, RpsJ, Adk, InfA, 16S rRNA, 30S rRNA, GyrA, DnaB, PolB, FtsZ, LpxC, RpoD, AroC, BlaT, CmI and/or AdeA and the bacterium is an *Klebsiella, Pseudomonas, Acinetobacter*, or *Escherichia* species which comprises or expresses one or more of AcpP, FabB, AccA, MurA, RpmB, RpsJ, Adk, InfA, 16S rRNA, 30S rRNA, GyrA, DnaB, PolB, FtsZ, LpxC, RpoD, AroC, BlaT, CmI and/or AdeA. In some embodiments, as described herein, the antisense oligomer is employed in combination with one or more antimicrobial agents, for example, to reduce (e.g., synergistically reduce) the growth of the bacteria or bacterium.

In some embodiments, the methods are practiced in vivo, and comprise administering the antisense oligomer to a subject in need thereof, for example, a subject in need thereof that is infected or at risk for being infected by one or more of the bacteria described herein. The antisense oligomers described herein can thus be administered to subjects to treat (prophylactically or therapeutically) an infection by any of the bacteria described herein. In conjunction with such treatment, pharmacogenomics (e.g., the study of the relationship between an individual's genotype/phenotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligomer to the target nucleic acid is one aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal, and topical delivery. The appropriate route may be determined by one of skill in the art, as appropriate to the condition of the subject under treatment. Vascular or extravascular circulation, the blood or lymph system, and the cerebrospinal fluid are some non-limiting sites where the antisense oligomers may be introduced. Direct CNS delivery may be employed, for instance, intracerebral, intraventricular, or intrathecal administration may be used as routes of administration.

In certain embodiments, the antisense oligomers can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025, the contents of which are incorporated in their entirety by reference herein.

The antisense oligomers described herein may also be delivered via an implantable device. Design of such a device is an art-recognized process, with, e.g., synthetic implant design described in, e.g., U.S. Pat. No. 6,969,400, the contents of which are incorporated by reference.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (see, e. g., Dokka and Rojanasakul, Advanced Drug Delivery Reviews 44:35-49, incorporated by reference in its entirety).

The antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically accept-able carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions The compounds (e.g., antisense oligomers, antimicrobial agents) described herein may generally be utilized as the free acid or free base. Alternatively, the compounds described herein may be used in the form of acid or base addition salts. Acid addition salts of the free amino compounds described herein may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligomers described herein. Further, in the case of a carboxylic acid (—COOH), esters may be employed, such as methyl esters, ethyl esters, and the like.

In some instances, liposomes may be employed to facilitate uptake of the antisense oligomer into cells (see, e.g., Williams, S. A., Leukemia 10(12):1980-1989, 1996; Lappalainen et al., Antiviral Res. 23:119, 1994; Uhlmann et al., antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In certain embodiments, the antisense oligomer is administered to a mammalian subject, e.g., human or domestic animal, exhibiting the symptoms of a bacterial infection (e.g., antibiotic resistance or MDR bacterial infection), in a suitable pharmaceutical carrier. In some aspects, the subject is a human subject, e.g., a patient diagnosed as having a bacterial infection. In particular embodiments, the antisense oligomer is contained in a pharmaceutically acceptable carrier, and is delivered orally. In some embodiments, the antisense oligomer is contained in a pharmaceutically acceptable carrier, and is delivered intravenously (i.v.).

In some embodiments, the antisense oligomer is administered in an amount and manner effective to result in a peak blood concentration of at least 200-400 nM antisense oligomer. Typically, one or more doses of antisense oligomer are administered, generally at regular intervals, for a period of about one to two weeks. Certain doses for oral administration are from about 1-1000 mg oligomer per 70 kg. In some cases, doses of greater than 1000 mg oligomer/patient may be necessary. For i.v. administration, some doses are from about 0.5 mg to 1000 mg oligomer per 70 kg. The antisense oligomer may be administered at regular intervals for a short time period, e.g., daily for two weeks or less. However, in some cases the antisense oligomer is administered intermittently over a longer period of time. Administration may be followed by, or concurrent with, administration of an antimicrobial (e.g., antibiotic) or other therapeutic treatment, as described herein. The treatment regimen may be adjusted (dose, frequency, route, etc.) as indicated, based on the results of immunoassays, other biochemical tests and physiological examination of the subject under treatment.

An effective in vivo treatment regimen using the antisense oligomers described herein may vary according to the duration, dose, frequency and route of administration, as well as the condition of the subject under treatment (i.e., prophylactic administration versus administration in response to localized or systemic infection). Accordingly, such in vivo therapy will often include monitoring by tests appropriate to the particular type of disorder or bacterial infection under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomer described herein may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

V. Combination Therapies

Certain embodiments include combination therapies, for example, the administration of antisense oligomers in combination with antimicrobial agents such as antibiotics. Combination therapies can be employed, for example, to increase the sensitivity or susceptibility of a given bacteria to one or more antimicrobial agents, and thereby improve the therapeutic outcome (e.g., resolution of the infection). Likewise, certain combination therapies can be employed, for example, to reduce or reverse the resistance of a given bacteria to one or more antimicrobial agents. In particular embodiments, the antisense oligomer reduces the minimum inhibitory concentration (MIC) of an antibiotic against a given bacterium. In certain embodiments, the antisense oligomer and the antimicrobial agent display synergy in reducing bacterial growth and/or increasing bacterial cell-killing. Also included are pharmaceutical compositions, as described herein, which comprise an antisense oligomer and an antimicrobial agent such as antibiotic.

In some embodiments, the antisense oligomer and the antimicrobial agent are administered separately. In certain embodiments, the antisense oligomer and the antimicrobial agent are administered sequentially. In some embodiments, the antisense oligomer and the antimicrobial agent are administered concurrently, for example, as part of the same or different pharmaceutical composition.

Examples of antimicrobial agents (e.g., antibiotics) that can be administered in combination with an antisense oligomer include beta-lactam antibiotics such as carbapenems, penicillin and penicillin derivatives (or penams), ampicillin, chloramphenicol, cephalosporins (e.g., Cefacetrile (cephacetrile), Cefadroxil (cefadroxyl; Duricef), Cephalexin (cefalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, loracarbef (Lorabid); Cephamycins: cefbuperazone, cefmetazole (Zefazone), cefminox, cefotetan (Cefotan), cefoxitin (Mefoxin), Cefotiam (Pansporin), Cefcapene, Cefdaloxime, Cefdinir (Sefdin, Zinir, Omnicef, Kefnir), Cefditoren, Cefetamet, Cefixime (Fixx, Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Meezat, Fortum, Fortaz), latamoxef (moxalactam), Cefclidine, cefepime (Maxipime), cefluprenam, cefoselis, Cefozopran, Cefpirome (Cefrom), Cefquinome, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime), and monobactams (e.g., aztreonam, tigemonam, nocardin A, tabtoxin); aminoglycosides such as tobramycin, gentamicin, kanamycin a, amikacin, dibekacin, sisomicin, netilmicin, neomycin B, neomycin C, neomycin E (paromomycin), and streptomycin; tetracyclines such as tetracycline, chlortetracycline, oxytetracycline, demeclocycline, lymecycline, meclocycline, methacycline, minocycline, rolitetracycline, and doxycyline; sulfonamides such as sulfacetamide, sulfadiazine, sulfadimidine, sulfafurazole, sulfisomidine, sulfadoxine, sulfamethoxazole, sulfamoxole, sulfadimethoxine, sulfamethoxypyridazine, sulfametoxydiazine, sulfadoxine, and sulfametopyrazine; quinolones such as cinoxacin, nalidixic acid, oxolinic acid (Uroxin), piromidic acid (Panacid), pipemidic acid (Dolcol) rosoxacin (Eradacil), ciprofloxacin (Alcipro,Ciprobay, Cipro, Ciproxin, ultracipro), enoxacin (Enroxil, Penetrex), fleroxacin (Megalone, Roquinol), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), balofloxacin (Baloxin), grepafloxacin (Raxar), levofloxacin (Cravit, Levaquin, Tavanic), pazufloxacin (Pasil, Pazucross), sparfloxacin (Zagam), temafloxacin (Omniflox), tosufloxacin (Ozex, Tosacin), clinafloxacin, gatifloxacin (Zigat, Tequin) (Zymar-opth.), gemifloxacin (Factive), moxifloxacin (Acflox Woodward, Avelox,Vigamox, sitafloxacin (Gracevit), trovafloxacin (Trovan), prulifloxacin (Quisnon); oxazolidinones such as eperezolid, linezolid, posizolid, radezolid, ranbezolid, sutezolid, and tedizolid; polymyxins such as polysporin, neosporin, polymyxin B, polymyxin E (colistin); rifamycins such as rifampicin or rifampin, rifabutin, rifapentine, and rifaximin; lipiarmycins such as fidaxomicin; macrolides such as azithromycin, clarithromycin, dirithromycin, erythromycin, roxithromycin, telithromycin, carbomycin A, josamycin, kitasamycin, midecamycin/midecamycin acetate, oleandomycin, solithromycin, spiramycin, and troleandomycin; lincosamides such as lincomycin, clindamycin, and pirlimycin; cyclic lipopeptides such as daptomycin; glycopeptides such as vancomycin and teichoplanin; glycylcyclines such as tigecycline. Thus, any one or more of the foregoing antibiotics can be combined with any of the antisense oligomers described herein, for the treatment of any of the bacterium or bacteria described herein.

In some embodiments, the antimicrobial agent is selected from one or more of aminoglycoside antibiotics, tetracycline antibiotics, and β-lactam antibiotics, as described herein. In some of these and related embodiments, the bacterium comprises or expresses a gene selected from one or more of acpP and fabB, and the antisense oligomer is targeted against expression of the fatty acid biosynthesis gene. In some of these and related embodiments, the bacterium comprises or expresses a gene selected from one or more of murA, and the antisense oligomer is targeted against expression of the peptidoglycan biosynthesis gene. In some of these and related embodiments, the bacterium comprises or expresses a gene selected from one or more of rpmB and rpsJ, and the antisense oligomer is targeted against expression of the ribosomal protein gene. In some of these and related embodiments, the bacterium comprises or expresses a gene selected from one or more of ftsZ, and the antisense oligomer is targeted against expression of the cell division gene. In some of these and related embodiments, the bacterium comprises or expresses a gene selected from one or more of gyrA, dnaB, and polB, and the antisense oligomer is targeted against expression of the DNA or chromosomal replication gene. In some of these and related embodiments, the bacterium comprises or expresses a gene selected from one or more of lpxC, and the antisense oligomer is targeted against expression of the lipopolysaccharide biosynthesis gene. In some of these and related embodiments, the bacterium comprises or expresses a ribosomal RNA selected from one or more of 5S rRNA, 16S rRNA, and 23s rRNA, and the antisense oligomer is targeted against the rRNA. In specific embodiments, the bacterium is *Klebsiella pneumoniae, Pseudomonas aeruginosa, Acinetobacter* spp., or *Escherichia coli*, including MDR strains thereof.

In some embodiments, the antimicrobial agent is a beta-lactam antibiotic, as described herein. In particular embodiments, the antimicrobial agent is a carbapenem. Examples of carbapenems include meropenem, imipenem, ertapenem, doripenem, panipenem, biapenem, razupenem, tebipenem, lenapenem, tomopenem, and ampicillin. In specific embodiments, the antimicrobial agent is meropenem. In particular embodiments, the antimicrobial agent is a cephalosporin (cephem), penicillin or penicillin derivative (penam). In particular embodiments, the antisense oligomer reduces the MIC of a carbapenem such as meropenem against a bacteria, for example, a strain or MDR strain of *Klebsiella pneumoniae, Pseudomonas aeruginosa, Acinetobacter baumannii,* or *E. coli*. In some embodiments, the combination of the antisense oligomer and the carbapenem such as meropenem reduces (e.g., synergistically reduces) bacterial cell growth or increase (e.g., synergistically increases) bacterial cell-killing, for example, of a strain or MDR strain of *Klebsiella pneumoniae, Pseudomonas aeruginosa, Acinetobacter baumannii*, or *E. coli*.

In some embodiments, the antimicrobial agent is an aminoglycoside, as described herein. Examples of aminoglycosides include tobramycin, gentamicin, kanamycin a, amikacin, dibekacin, sisomicin, netilmicin, neomycin B, neomycin C, neomycin E (paromomycin), and streptomycin. In specific embodiments, the antimicrobial agent is tobramycin. In particular embodiments, the antisense oligomer reduces the MIC of an aminoglycoside such as tobramycin against a bacteria, for example, a strain or MDR strain of *Klebsiella pneumoniae, Pseudomonas aeruginosa, Acinetobacter baumannii*, or *E. coli*. In some embodiments, the combination of the antisense oligomer and the aminoglycoside such as tobramycin reduces (e.g., synergistically reduces) bacterial cell growth or increases (e.g., synergistically increases) bacterial cell-killing, for example, of a strain or MDR strain of *Klebsiella pneumoniae, Pseudomonas aeruginosa, Acinetobacter baumannii*, or *E. coli*.

In certain embodiments, the antimicrobial agent is a polymyxin such as colistin (polymyxin E), polysporin, neosporin, or polymyxin B. In specific embodiments, the antimicrobial agent is colistin. In particular embodiments, the antisense oligomer reduces the MIC of a polymyxin such as colistin against a bacteria, for example, a strain or MDR strain of *Klebsiella* pneumoniae, *Pseudomonas aeruginosa, Acinetobacter baumannii*, or *E. coli*. In some embodiments, the combination of the antisense oligomer and the polymyxin such as colistin reduces (e.g., synergistically reduces) bacterial cell growth or increases (e.g., synergistically increases) bacterial cell-killing, for example, of a strain or MDR strain of *Klebsiella pneumoniae, Pseudomonas aeruginosa, Acinetobacter baumannii*, or *E. coli*.

In certain embodiments, the antimicrobial agent includes one or more of ceftazidime, doxycycline, piperacillin, meropenem, chloramphenicol, and/or co-trimoxazole (trimethoprim/sulfamethoxazole).

In some embodiments, the antisense oligomer increases the susceptibility or sensitivity of a given bacterium to the antimicrobial agent, relative to the antimicrobial agent alone. For example, in certain embodiments, the antisense oligomer increases the susceptibility or sensitivity of the bacteria or bacterium to the antimicrobial agent by increasing the bactericidal (cell-killing) and/or bacteriostatic (growth-slowing) activity of the antimicrobial agent against the bacteria or bacterium being targeted, relative to the antimicrobial agent alone. In particular embodiments, the antisense oligomer increases the susceptibility or sensitivity by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone, or by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to the antimicrobial agent alone. In some embodiments, the antisense oligomer synergistically increases the susceptibility or sensitivity of a given bacterium to the antimicrobial agent, relative to the antimicrobial agent alone. In some embodiments, the bacterium is *Klebsiella pneumoniae, Pseudomonas aeruginosa, Acinetobacter baumannii,* or *E. coli,* or an MDR strain thereof.

In some embodiments, the antisense oligomer reduces the minimum inhibitory concentration (MIC) of an antimicrobial agent against the bacteria or bacterium being targeted, relative to the antimicrobial agent alone. The "minimum inhibitory concentration" or "MIC" refers to the lowest concentration of an antimicrobial agent that will inhibit the visible growth of a microorganism after overnight (in vitro) incubation. Minimum inhibitory concentrations are important in diagnostic laboratories to confirm resistance of microorganisms to an antimicrobial agent and also to monitor the activity of new antimicrobial agents. The MIC is generally regarded as the most basic laboratory measurement of the activity of an antimicrobial agent against a bacterial organism. Thus, in certain embodiments, the oligomer reduces the minimum inhibitory concentration (MIC) of an antimicrobial agent against the bacteria or bacterium by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone. In certain embodiments, the oligomer reduces the minimum inhibitory concentration (MIC) of an antimicrobial agent against the bacteria or bacterium by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to the antimicrobial agent alone. In some embodiments, the antisense oligomer synergistically reduces the MIC of an antimicrobial agent against the bacteria or bacterium being targeted, relative to the antimicrobial agent alone. In some embodiments, the bacterium is *Klebsiella pneumoniae, Pseudomonas aeruginosa, Acinetobacter baumannii,* or *E. coli,* or an MDR strain thereof.

VI. Treatment Monitoring Methods

The efficacy of a given therapeutic regimen involving the methods described herein may be monitored, for example, by general indicators of bacterial infection, such as complete blood count (CBC), nucleic acid detection methods, immunodiagnostic tests, or bacterial culture.

In some aspects, identification and monitoring of bacterial infection involves one or more of (1) nucleic acid detection methods, (2) serological detection methods, i.e., conventional immunoassay, (3) culture methods, and (4) biochemical methods. Such methods may be qualitative or quantitative.

Nucleic acid probes may be designed based on publicly available bacterial nucleic acid sequences, and used to detect target genes or metabolites (i.e., toxins) indicative of bacterial infection, which may be specific to a particular bacterial type, e.g., a particular species or strain, or common to more than one species or type of bacteria (i.e., Gram positive or Gram negative bacteria). Nucleic amplification tests (e.g., PCR) may also be used in such detection methods.

Serological identification may be accomplished using a bacterial sample or culture isolated from a biological specimen, e.g., stool, urine, cerebrospinal fluid, blood, etc. Immunoassay for the detection of bacteria is generally carried out by methods routinely employed by those of skill in the art, e.g., ELISA or Western blot. In addition, monoclonal antibodies specific to particular bacterial strains or species are often commercially available.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses, and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

The PMO or PPMO treatment regimen may be adjusted (dose, frequency, route, etc.), as indicated, based on the results of immunoassays, other biochemical tests and physiological examination of the subject under treatment.

From the foregoing, it will be appreciated how various objects and features of the present disclosure are met. The method provides an improvement in therapy against bacterial infection, for example, multi-drug resistant (MDR) bacteria, using various PPMOs to achieve enhanced cell uptake and anti-bacterial action. As a result, drug therapy is more effective and less expensive, both in terms of cost and amount of compound required.

One exemplary aspect is that compounds effective against virtually any pathogenic bacterial can be readily designed and tested, e.g., for rapid response against new drug-resistant strains.

The following examples are intended to illustrate but not to limit the disclosure. Each of the patent and non-patent references referred to herein is incorporated by reference in its entirety.

EXAMPLES

Materials and Methods

Peptide-Conjugated Phosphorodiamidate Morpholino Oligomers. PPMOs were synthesized and purified at Sarepta Therapeutics Inc. (Cambridge, MA, USA) as previously described (Tilley et al., Antimicrob Agents Chemother 50:2789-2796, 2006). Lyophilized PPMOs were dissolved in ultrapure water and sterile-filtered. PPMO peptides were attached to either the 5' or 3' end of the oligomer sequence as indicated.

Bacteria. Bacterial strains were obtained through the clinical microbiology lab at UT Southwestern unless otherwise noted.

Minimal Inhibitory Concentration Assays. Minimal inhibitory concentration (MIC) assays were performed in Mueller Hinton II medium using the microdilution method as described by the Clinical and Laboratory Standards Institute (CLSI). Optical density (OD) of cultures was read in a microplate spectrophotometer at 595-600 nm. After 18-20 hours of aerobic growth (200-250 rpm) at 37° C., 100 µl cultures with an OD of <0.06 were scored as no growth.

Graphical Software. Standard deviation and graphical analysis was performed on GraphPad Prism®6 software (GraphPad Software, Inc., San Diego, CA, USA).

Example 1

Activity of PPMOs Targeted Against Expression of Essential Genes of K. pneumoniae PPMOs were designed, synthesized, and tested against the expression of essential genes representing a variety of biochemical pathways and cellular processes in Klebsiella pneumoniae. These included: murein biosynthesis, cell division, global gene regulatory mechanisms, fatty acid biosynthesis, ribosomal proteins, DNA replication, transcription, translation initiation, lipopolysaccharide biosynthesis, nucleic acid biosynthesis, and intermediary metabolism.

Each PPMO was tested by measuring the minimal inhibitory concentration (MIC) according to the method described above (CLSI microdilution assay). The MIC of each PPMO was tested using a panel of 38 strains of K. pneumoniae, shown in Table E1 below, including eight that express the KPC carbapenemase, five that express the NDM-1 carbapenemase, two that express the OXA-48 carbapenemase, and others that are multidrug resistant (MDR).

TABLE E1

| Strains of Klebsiella pneumoniae |
| --- |
| BAA 2146 |
| NDM1-A |
| NDM1-B |
| NDM1-C |
| NDM1-D |
| Hm 748 |
| Hm 749 |
| Hm 750 |
| Hm 751 |
| Pneu3426 |
| Pneu3427 |
| Pneu3190 |
| Pneu3290 |
| NR 15410 |
| NR 15411 |
| NR 15412 |
| NR 15416 |
| NR 15417 |
| OR-001 |
| OR-002 |
| OR-003 |
| OR-004 |
| OR-005 |
| OR-006 |
| OR-007 |
| OR-008 |

TABLE E1-continued

| Strains of Klebsiella pneumoniae |
| --- |
| OR-009 |
| OR-010 |
| OR-011 |
| OR-012 |
| OR-013 |
| OR-014 |
| OR-015 |
| OR-016 |
| OR-017 |
| OR-018 |
| OR-019 |
| OR-020 |

The results are shown in FIG. 2. At least four of the PPMOs inhibited growth of at least 75% of the strain panel (IC75) at a concentration of 8 µM or less.

These data show, inter alia, that PPMOs targeted against biochemical pathways and cellular processes of numerous strains of K. pneumoniae, including MDR strains and those that express antibiotic-resistance genes, are bactericidal at clinically-relevant concentrations (e.g., $IC_{75}$ of 8 µM or less).

Example 2

Activity of PPMOs Targeted Against Ribosomal RNA

PPMOs targeted against ribosomal RNA (rRNA) were designed by positioning them at highly conserved regions of the 5S, 16S and 23S rRNA. Each sequence was then aligned and compared with the equivalent rRNAs in Homo sapiens, and any PPMO sequence with a complementary match of 10 or more bases was eliminated.

Each PPMO was then tested by measuring the minimal inhibitory concentration (MIC) according to the method described above (CLSI microdilution assay).

As shown in FIG. 3, the results of MIC testing show that at least three of the PPMOs (PPMO #15, PPMO #17, and PPMO #18 targeted to 23S-858, 16S-1101, and 16S-1101, respectively) inhibited growth of at least two of the three targeted pathogens. The inhibitory concentration of 75% of the strains tested (IC75) was 8 µM or less for PPMO #15 in K. pneumoniae and P. aeruginosa, and for PPMO #18 in P. aeruginosa and Acinetobacter baumannii.

These data show, inter alia, that PPMOs targeted against bacterial rRNA of a variety of strains of K. pneumoniae, P. aeruginosa, and A. baumannii are bactericidal at clinically-relevant concentrations (e.g., $IC_{75}$ of 8 µM or less).

The invention claimed is:

1. An antisense morpholino oligomer of formula (I):

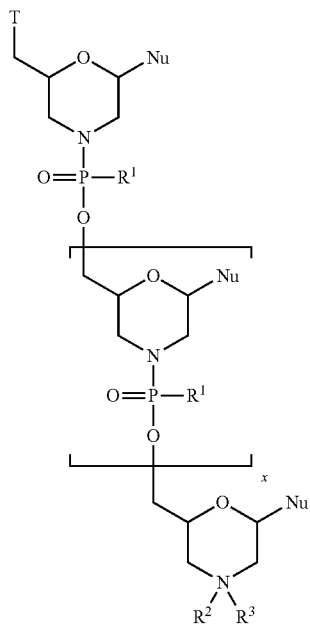

or a pharmaceutically acceptable salt thereof,
where each Nu is a nucleobase which taken together forms a targeting sequence, where the targeting sequence is SEQ ID NO: 1 (CTC ATACCTTG);

and where thymine bases (T) may be uracil bases (U) X is an integer from 9 to 38;

T is selected from OH and a moiety of the formula:

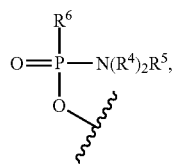

where each $R^4$ is independently C1-C6 alkyl, and $R^5$ is selected from an electron pair and H, and $R^6$ is selected from OH, —N($R^7$)CH$_2$C(O)NH$_2$, and a moiety of the formula:

where:
$R^7$ is selected from H and $C_1$-$C^6$ alkyl, and
$R^8$ is selected from G, —C(O)—$R^9$OH, acyl, trityl, and 4-methoxytrityl, where:
$R^9$ is of the formula —(O-alkyl)$_y$- where y is an integer from 3 to 10 and each of the y alkyl groups is independently selected from $C_2$-$C_6$ alkyl;
each instance of $R^1$ is —N($R^{10}$)$_2$$R^{11}$ where each $R^{10}$ is independently C2-C6 alkyl, and $R^{11}$ is selected from an electron pair and H;
$R^2$ is selected from H, G, acyl, trityl, 4-methoxytrityl, benzoyl, stearoyl, and a moiety of the formula:

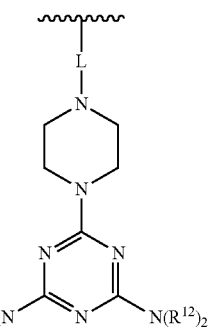

where L is selected from —C(O)(CH$_2$)$_6$C(O)— and —C(O)(CH$_2$)$_2$S$_2$(CH$_2$)$_2$C(O)— and each $R^{12}$ is of the formula —(CH$_2$)$_2$OC(O)N($R_{14}$)$_2$ where each $R^{14}$ is of the formula —(CH$_2$)$_6$NHC(=NH)NH$_2$; and
$R^3$ is selected from an electron pair, H, and C1-C6 alkyl,
where G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$N HC(O)(CH$_2$)$_5$NH—CPP, and —C(O)CH$_2$NH—CPP, or G is of the formula:

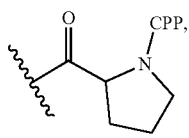

where the CPP is attached to the linker moiety by an amide bond at the CPP carboxy terminus, with the proviso that only one instance of G is present, where the targeting sequence specifically hybridizes to a bacterial nRNA target sequence that encodes a protein associated with a biochemical pathway and/or cellular process, or a ribosomal RNA (rRNA) target sequence.

2. The antisense morpholino oligomer of claim 1, where T is selected from:

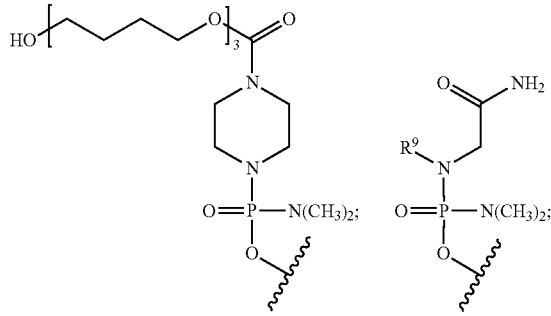

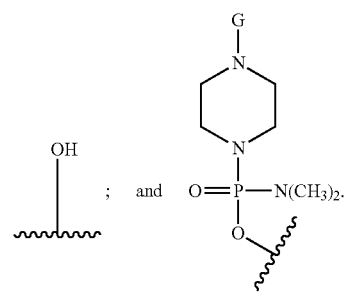

3. The antisense morpholino oligomer of claim 1, where $R^2$ is selected from H, G, acyl, trityl, 4-methoxytrityl, benzoyl, and stearoyl.

4. The antisense morpholino oligomer of claim 1, where T is selected from:

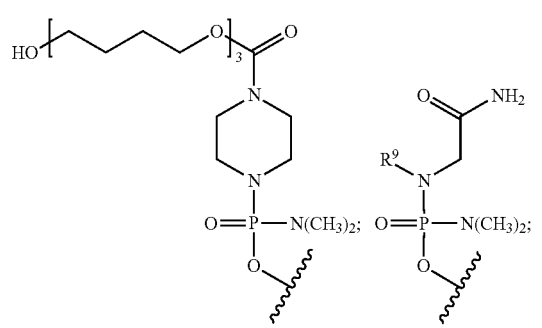

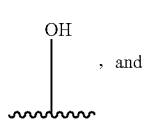

$R^2$ is G.

5. The antisense morpholino oligomer of claim 1, where T is of the formula:

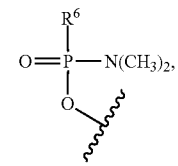

$R^6$ is of the formula:

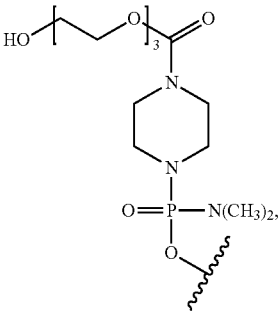

and $R^2$ is G.

6. The antisense morpholino oligomer of claim 1, where T is of the formula:

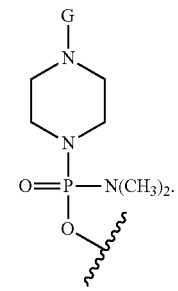

and $R^2$ is G.

7. The antisense morpholino oligomer of claim 1, where T is of the formula:

8. The antisense morpholino oligomer of claim 7, where $R^2$ is selected from H, acyl, trityl 4-methoxytrityl, benzoyl, and stearoyl.

9. The antisense morpholino oligomer of claim 1, where at least one instance of $R^1$ is —N(CH$_3$)$_2$.

10. The antisense morpholino oligomer of claim 9, where each $R^1$ is —N(CH$_3$)$_2$.

11. The antisense morpholino oligomer of claim 1, where the CPP is selected from:

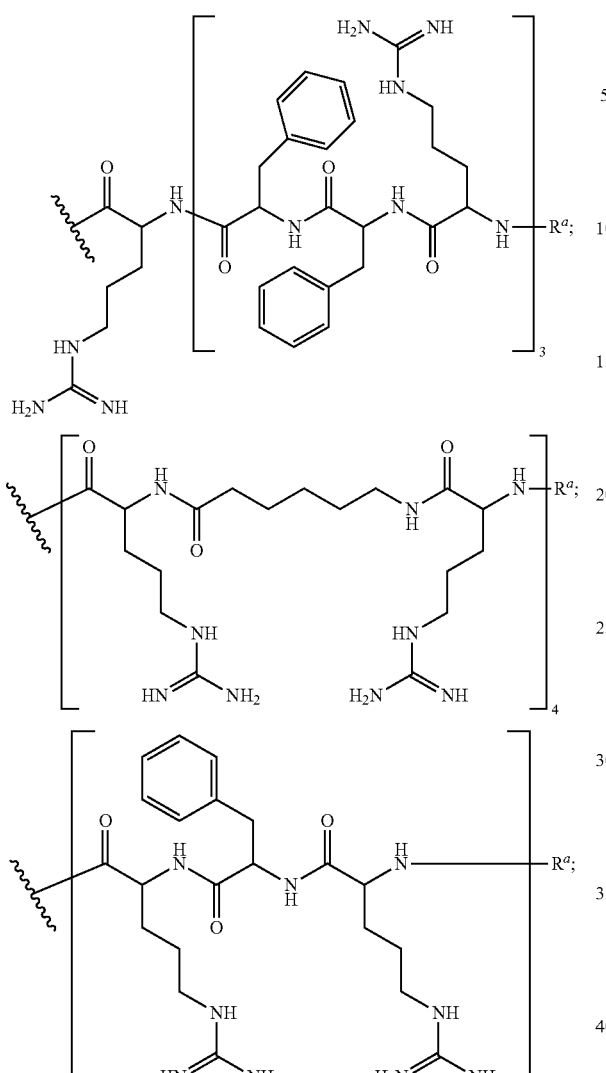
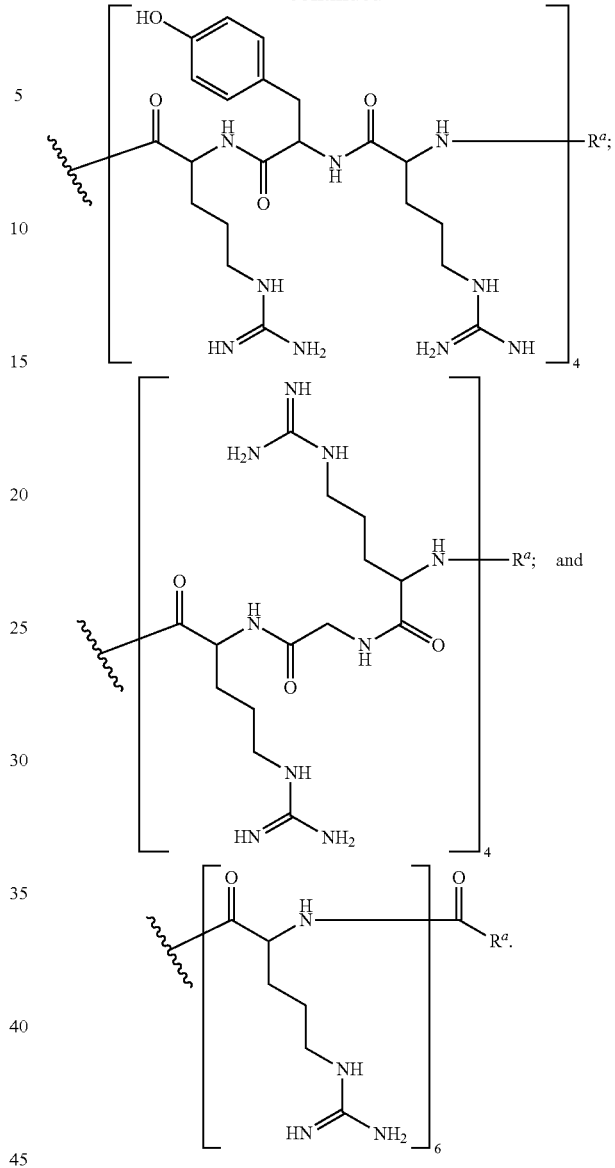
where $R^a$ is H.
12. The antisense morpholino oligomer of claim 1, where G is selected from:
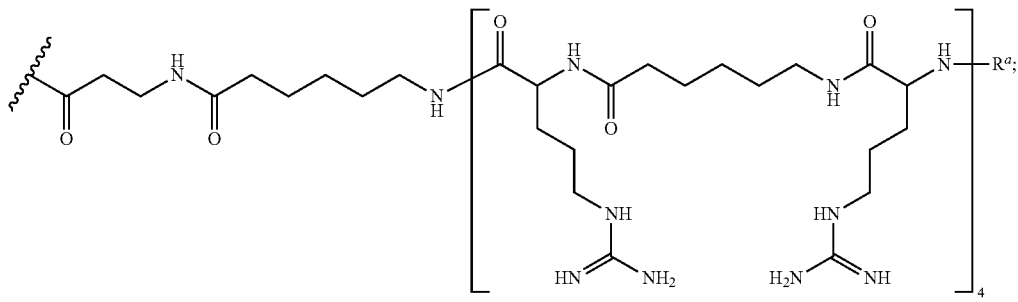

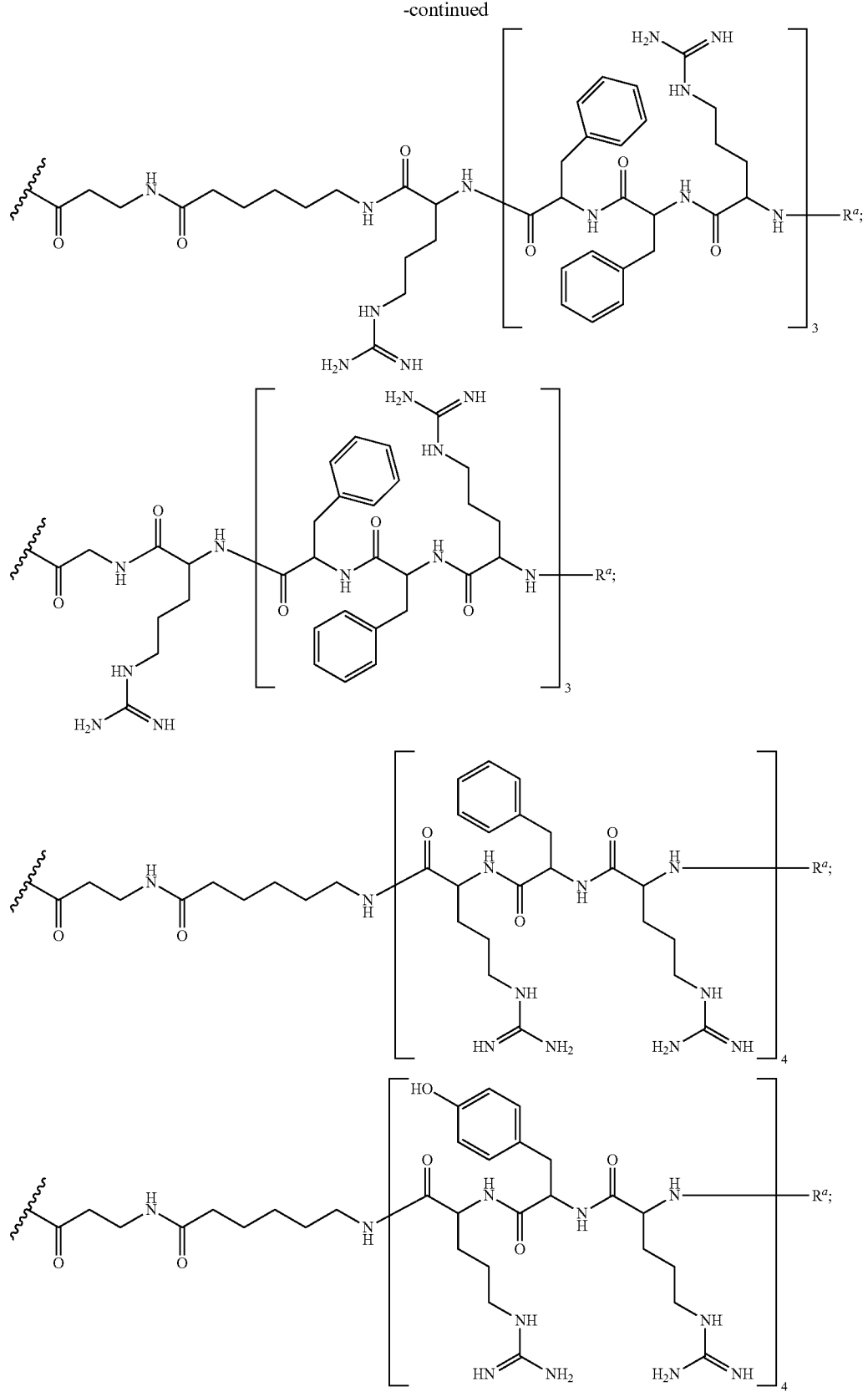

-continued
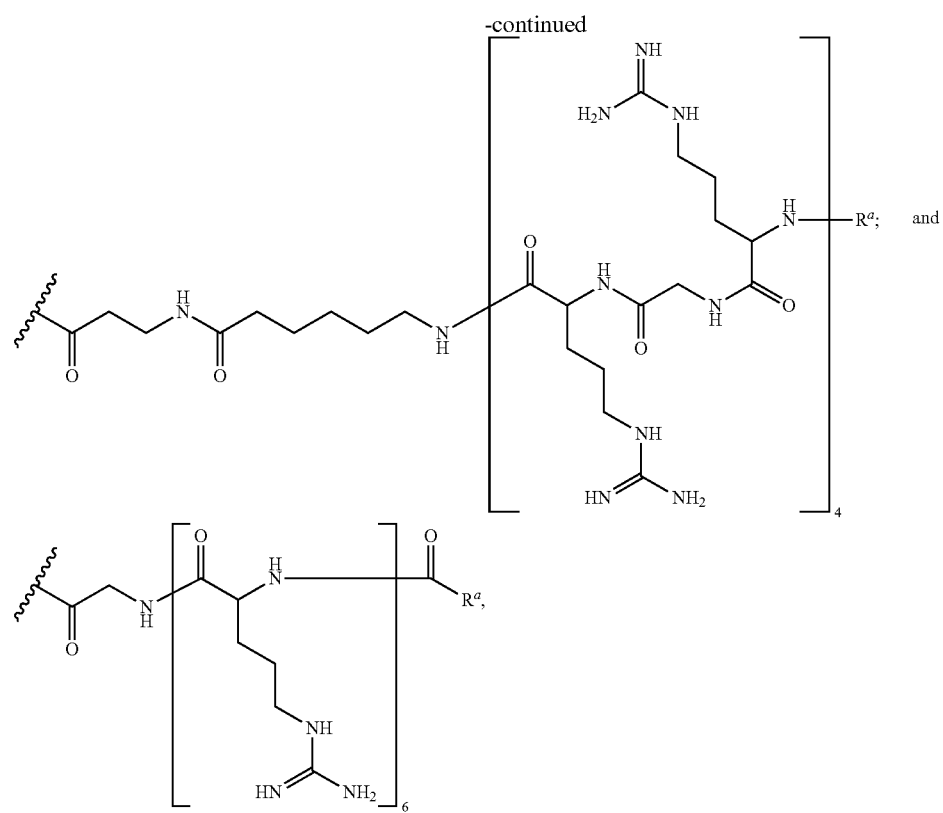
where $R^a$ is H.
13. The antisense morpholino oligomer of claim 1, where the antisense oligomer is of the formula (VII) selected from:

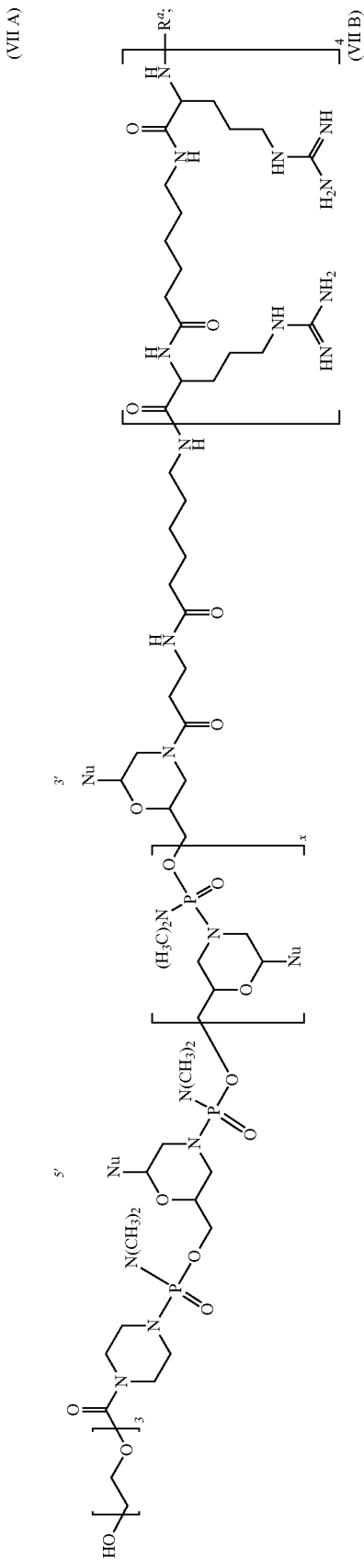
(VII A)
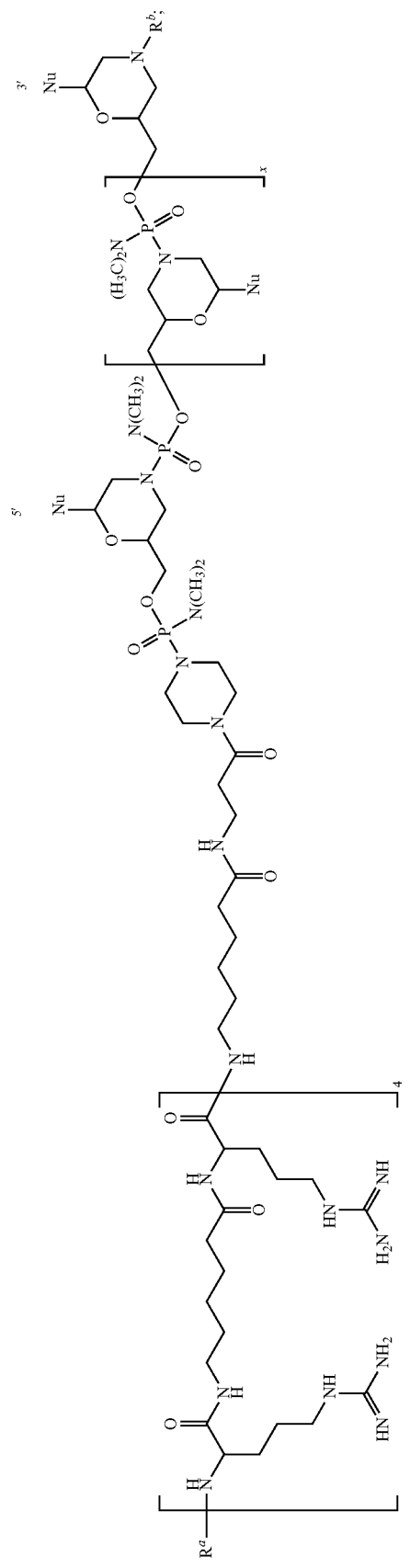
(VII B)

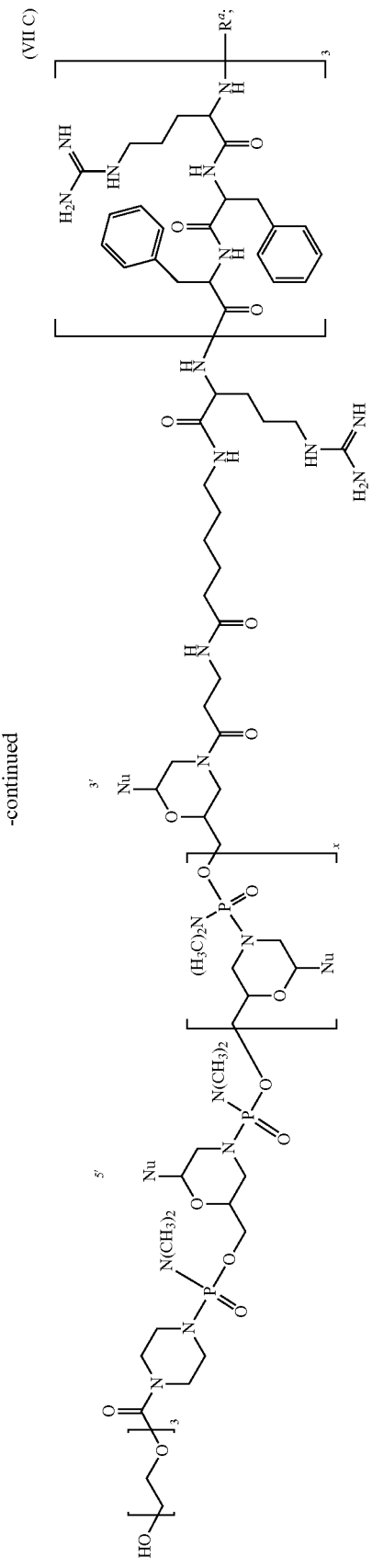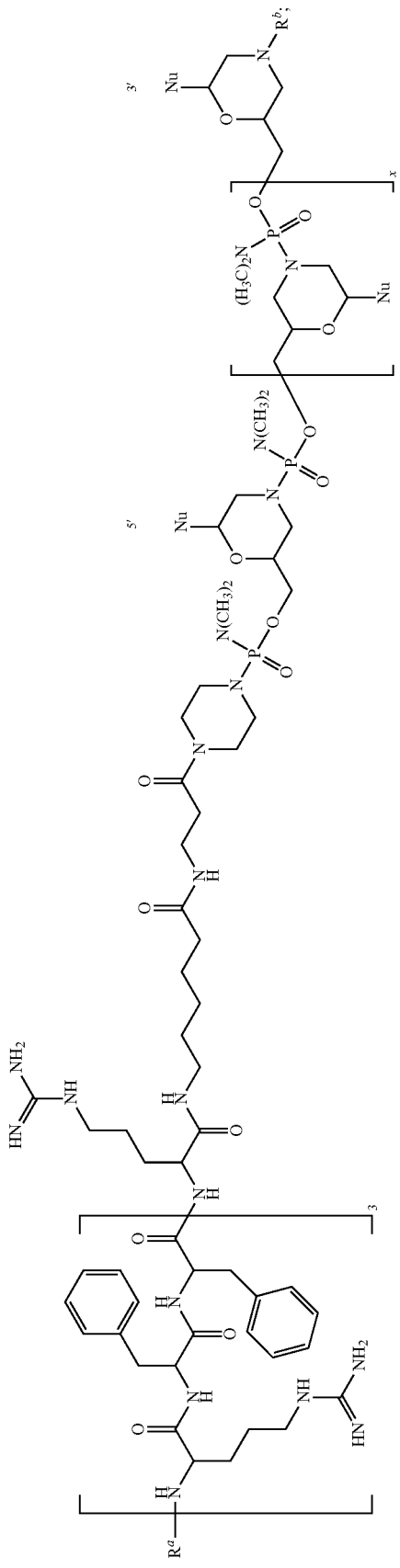

-continued
(VII E)
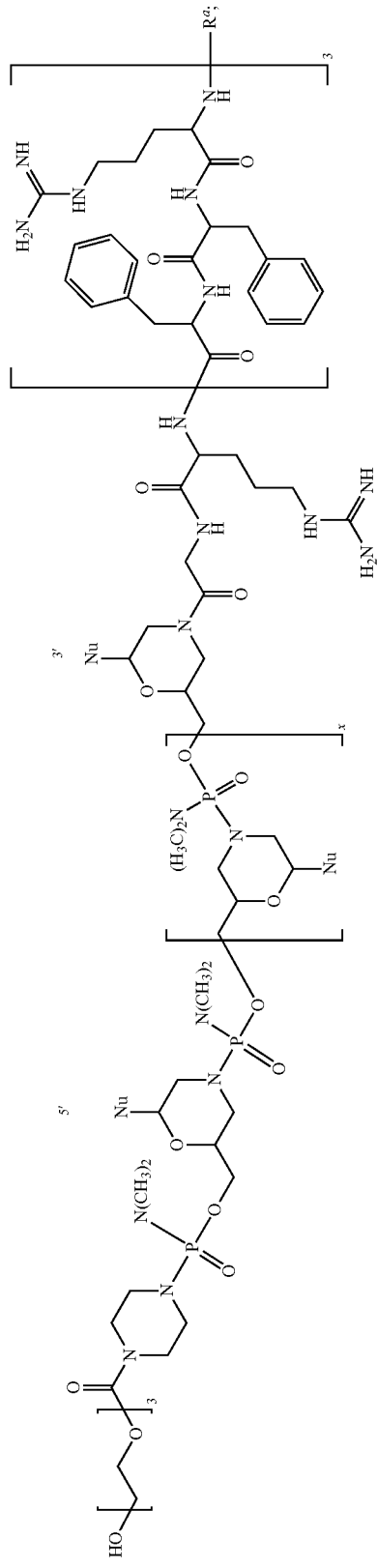
(VII F)
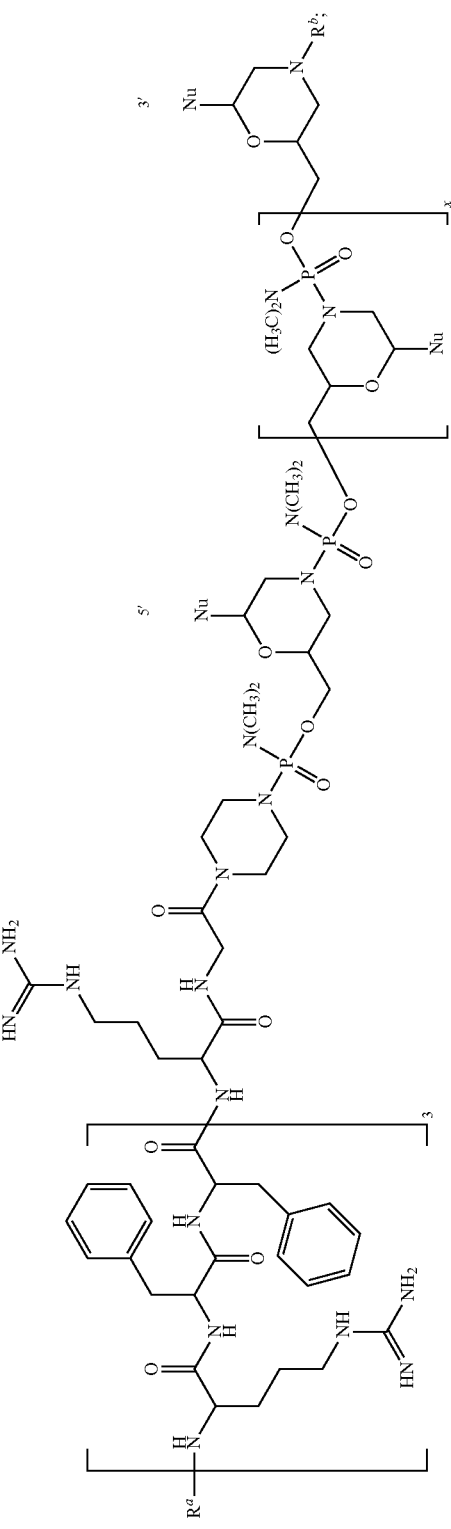

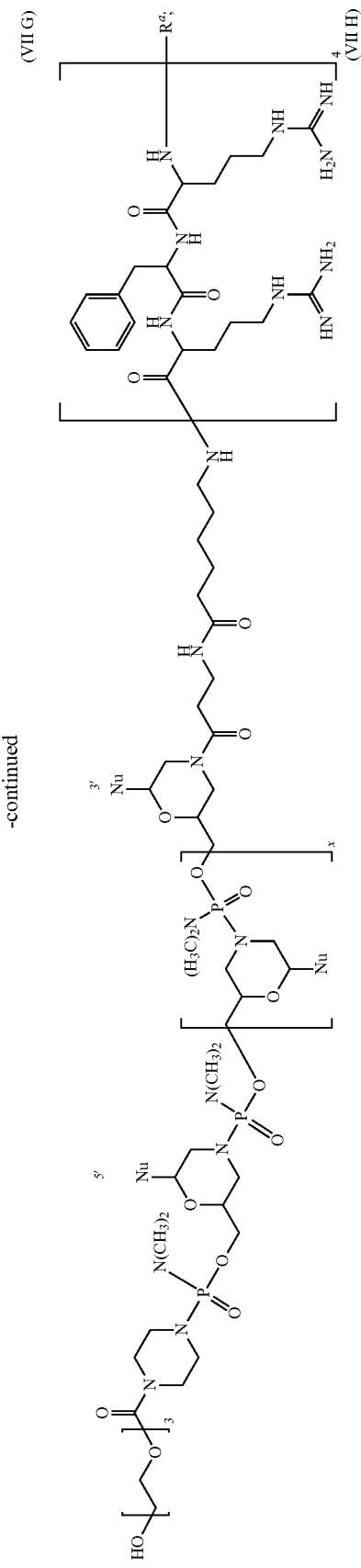
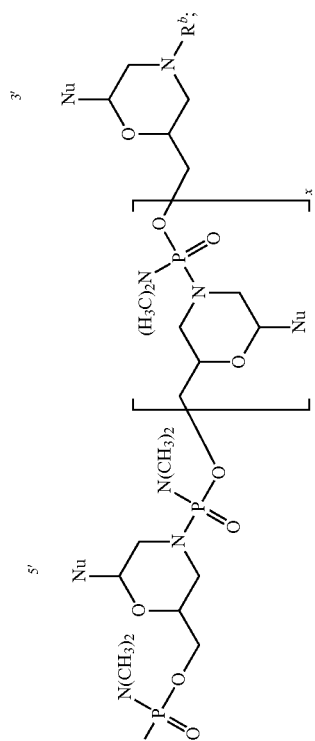
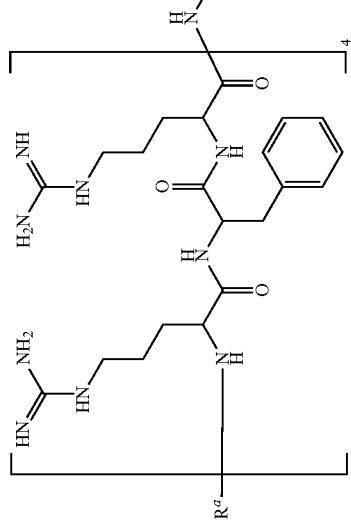
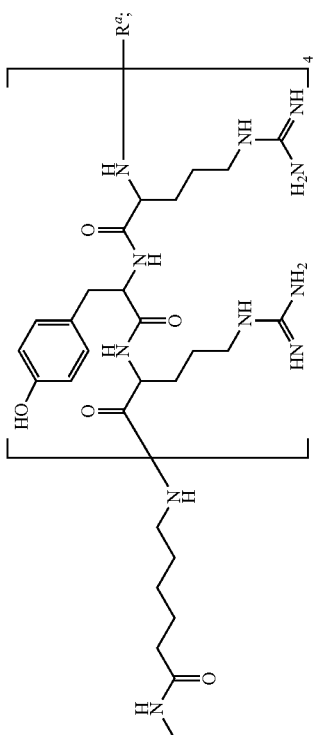
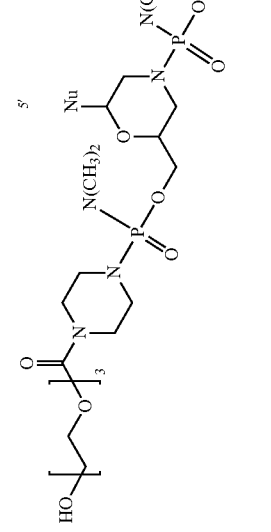

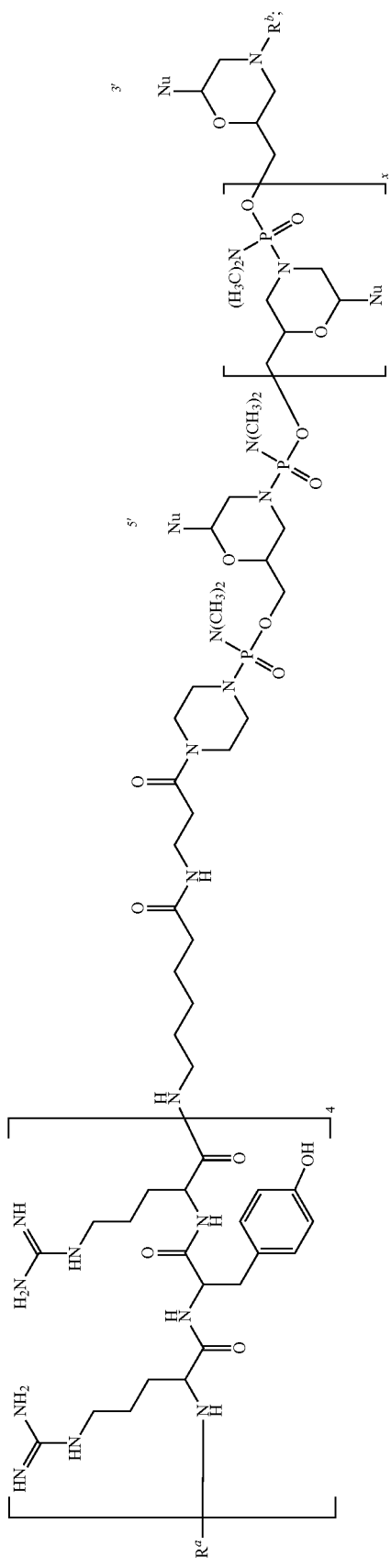
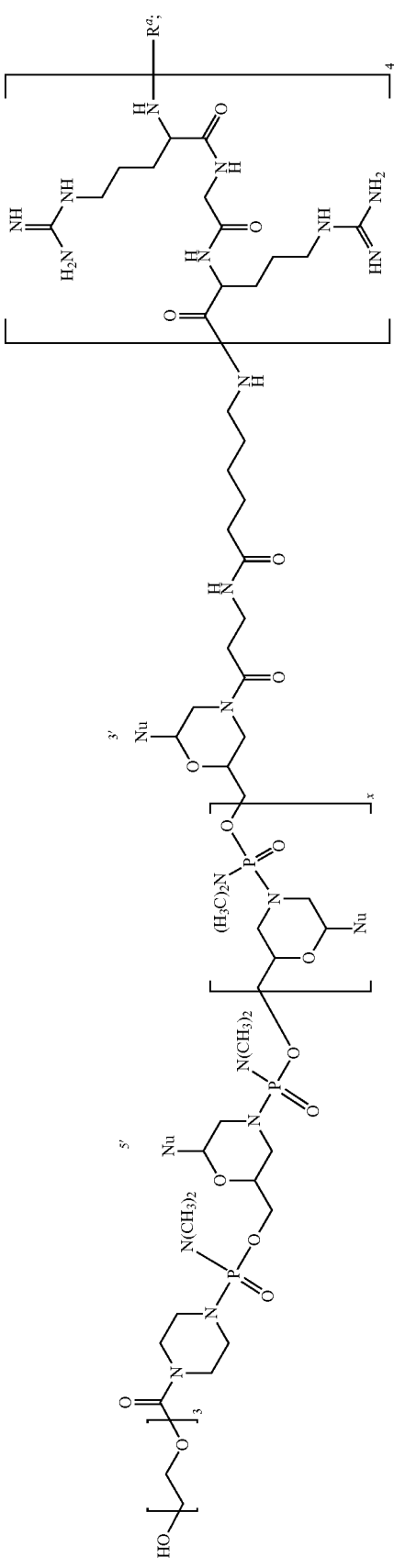

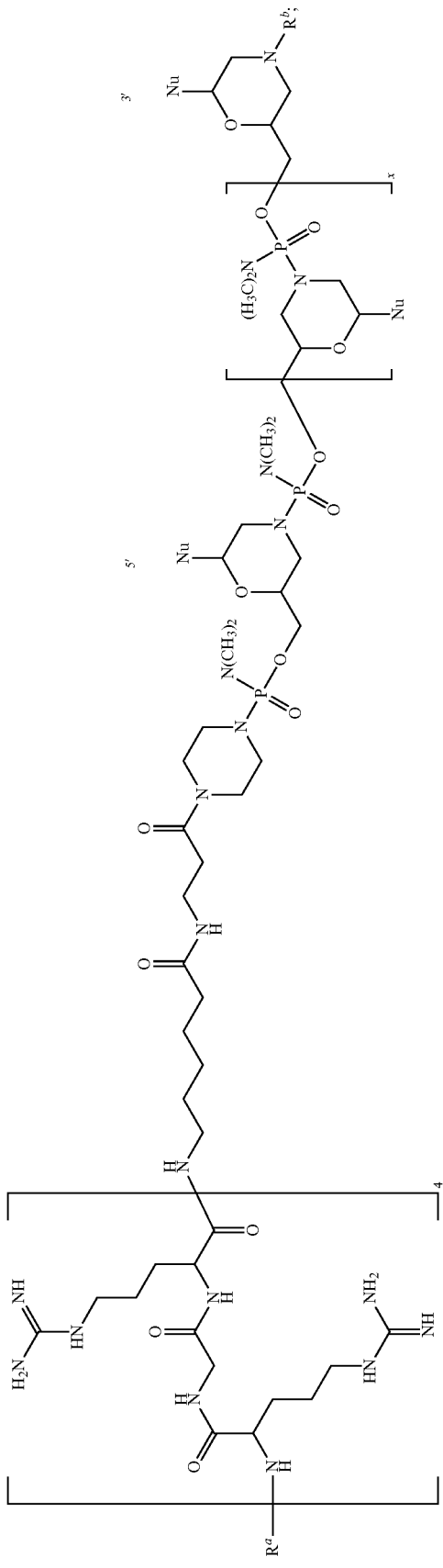
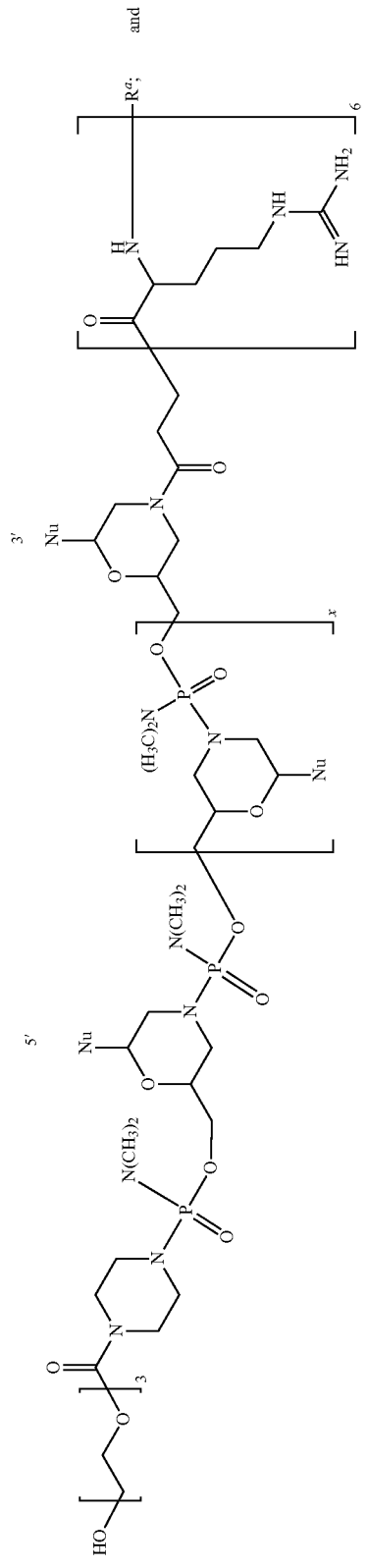

-continued
(VII N)
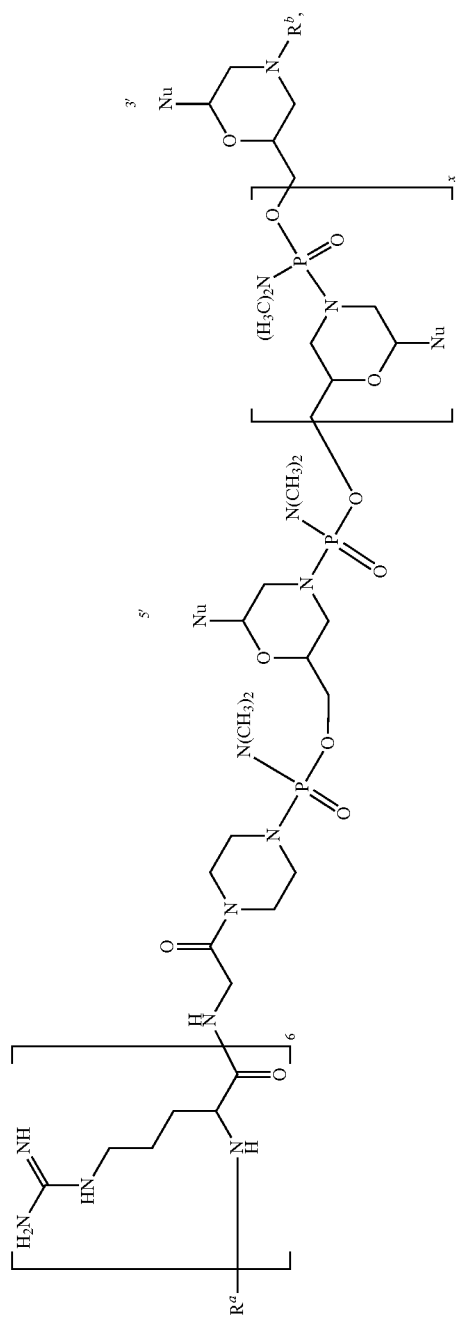

or a pharmaceutically acceptable salt of any of the foregoing,
where $R^a$ is H, and $R^b$ is selected from H, acetyl, benzoyl, stearoyl, trityl, and 4-methoxytrityl.

14. The antisense morpholino oligomer of claim 13, where $R^a$ and $R^b$ are H.

15. A pharmaceutical composition, comprising a pharmaceutically acceptable carrier and an antisense morpholino oligomer according to claim 1.

16. A method of reducing expression and activity of a protein associated with a biochemical pathway and/or cellular process in a bacterium, comprising contacting the bacterium with an antisense morpholino oligomer according to claim 1.

* * * * *